US008460931B2

(12) United States Patent
Reubinoff et al.

(10) Patent No.: US 8,460,931 B2
(45) Date of Patent: *Jun. 11, 2013

(54) NEURAL PROGENITOR CELLS DERIVED FROM EMBRYONIC STEM CELLS

(75) Inventors: Benjamin Eithan Reubinoff, Moshav Bar-Giora (IL); Martin Federick Pera, Los Angeles, CA (US); Tamir Ben-Hur, Jerusalem (IL)

(73) Assignee: ES Cell International PTE Ltd., Singapore (SG)

( * ) Notice: Subject to any disclaimer, the term of this patent is extended or adjusted under 35 U.S.C. 154(b) by 0 days.

This patent is subject to a terminal disclaimer.

(21) Appl. No.: 13/361,976

(22) Filed: Jan. 31, 2012

(65) Prior Publication Data

US 2012/0122109 A1    May 17, 2012

Related U.S. Application Data

(60) Division of application No. 12/157,864, filed on Jun. 13, 2008, now Pat. No. 8,137,969, which is a continuation of application No. 11/238,574, filed on Sep. 29, 2005, now abandoned, which is a continuation of application No. 09/970,543, filed on Oct. 4, 2001, now Pat. No. 7,011,828, which is a continuation-in-part of application No. 09/808,382, filed on Mar. 14, 2001, now Pat. No. 7,504,257.

(30) Foreign Application Priority Data

Mar. 14, 2000  (AU) ...................................... PQ6211
Nov. 6, 2000   (AU) ...................................... PR1279
Feb. 6, 2001   (AU) ...................................... PR2920

(51) Int. Cl.
    *C12N 5/00*    (2006.01)
    *C12N 5/02*    (2006.01)
    *C12N 5/071*   (2010.01)

(52) U.S. Cl.
    USPC ............ 435/377; 435/366; 435/368; 435/384

(58) Field of Classification Search
    USPC .................................... 435/377, 366, 368, 384
    See application file for complete search history.

(56) References Cited

U.S. PATENT DOCUMENTS

| 5,200,148 A | 4/1993 | Saito |
| 5,693,482 A | 12/1997 | Anderson et al. |
| 5,843,780 A | 12/1998 | Thomson |
| 6,200,806 B1 | 3/2001 | Thomson |
| 6,833,269 B2 | 12/2004 | Carpenter |
| 7,011,828 B2 | 3/2006 | Reubinoff et al. |
| 7,504,257 B2 | 3/2009 | Reubinoff et al. |
| 7,947,498 B2 | 5/2011 | Reubinoff et al. |
| 8,137,969 B2 | 3/2012 | Reubinoff et al. |
| 2002/0068045 A1 | 6/2002 | Reubinoff et al. |
| 2002/0164308 A1 | 11/2002 | Reubinoff et al. |
| 2005/0260747 A1 | 11/2005 | Reubinoff et al. |
| 2006/0078543 A1 | 4/2006 | Reubinoff et al. |
| 2009/0075373 A1 | 3/2009 | Reubinoff et al. |
| 2009/0258421 A1 | 10/2009 | Reubinoff et al. |
| 2012/0115229 A1 | 5/2012 | Reubinoff et al. |

FOREIGN PATENT DOCUMENTS

| AU | 2001263199 | 11/2001 |
| CA | 2315538 | 7/1999 |
| CA | 2403000 | 9/2001 |
| WO | WO 99/11758 | 3/1999 |
| WO | WO 99/32606 | 7/1999 |
| WO | WO 00/27995 | 5/2000 |
| WO | WO 00/55312 | 9/2000 |
| WO | WO 00/58359 | 10/2000 |
| WO | WO 00/68359 | 11/2000 |
| WO | WO 01/68815 | 9/2001 |
| WO | WO 01/88104 | 11/2001 |

OTHER PUBLICATIONS

Pleasure et al., J. Neurosci. Res, 35(6): 585-602, 1993, Abstract Only.*
Communication Pursuant to Article 94(3) EPC Dated Feb. 1, 2010 From the European Patent Office Re.: Application No. 01911277.0.
Communication Pursuant to Article 94(3) EPC Dated Nov. 10, 2010 From the European Patent Office Re.: Application No. 01911277.0.
Communication Pursuant to Article 96(2) Dated Apr. 26, 2006 From the European Patent Office Re. Application No. 02256974.3.
European Search Report Dated Feb. 6, 2004 From the European Patent Office Re. Application No. 02256974.3.
Examiner's Report Dated Oct. 17, 2007 From the Government of Australia, IP Australia Re.: Application No. 2002301347.
Examiner's Report Dated Aug. 24, 2006 From the Government of Australia, IP Australia Re.: Application No. 2002301347.
Examiner's Report Dated Jul. 31, 2006 From the Government of Australia, IP Australia Re.: Application No. 2005200148.
International Preliminary Examination Report Dated Apr. 8, 2002 From the International Preliminary Examining Authority Re.: Application No. PCT/AU01/00278.
International Search Report Dated May 10, 2001 From the International Searching Authority Re.: Application No. PCT/AU01/00278.
Invitation to Pay Additional Fees Dated Apr. 5, 2001 From the International Searching Authority Re.: Application No. PCT/AU01/00278.
Notice of Allowance Dated Jan. 18, 2011 From the US Patent and Trademark Office Re.: U.S. Appl. No. 12/367,075.
Notice of Allowance Dated Oct. 23, 2008 From the US Patent and Trademark Office Re.: U.S. Appl. No. 09/808,382.

(Continued)

Primary Examiner — Thaian N Ton

(57) ABSTRACT

The present invention relates to undifferentiated human embryonic stem cells, methods of cultivation and propagation and production of differentiated cells. In particular it relates to the production of human ES cells capable of yielding somatic differentiated cells in vitro, as well as committed progenitor cells such as neural progenitor cells capable of giving rise to mature somatic cells including neural cells and/or glial cells and uses thereof. This invention provides methods that generate in vitro and in vivo models of controlled differentiation of ES cells towards the neural lineage. The model, and cells that are generated along the pathway of neural differentiation may be used for: the study of the cellular and molecular biology of human neural development, discovery of genes, growth factors, and differentiation factors that play a role in neural differentiation and regeneration, drug discovery and the development of screening assays for teratogenic, toxic and neuroprotective effects.

15 Claims, 37 Drawing Sheets
(24 of 37 Drawing Sheet(s) Filed in Color)

OTHER PUBLICATIONS

Notice of Allowance Dated Oct. 26, 2011 From the US Patent and Trademark Office Re.: U.S. Appl. No. 12/157,864.
Office Action Dated Sep. 4, 2007 From the Israeli Patent Office Re.: Application No. 151170.
Office Action Dated Sep. 4, 2007 From the Israeli Patent Office Re.: Application No. 152106.
Office Action Dated Oct. 5, 2008 From the Israeli Patent Office Re.: Application No. 152106 and Its Translation Into English.
Office Action Dated Apr. 7, 2008 From the Israeli Patent Office Re.: Application No. 151170.
Office Action Dated Jun. 15, 2009 From the Israeli Patent Office Re.: Application No. 151170 and Its Translation Into English.
Office Action Dated Nov. 24, 2009 From the Israel Patent Office Re.: Application No. 152106 and Its Translation Into English.
Office Action Dated Jul. 25, 2010 From the Israeli Patent Office Re.: Application No. 152106 and Its Translation Into English.
Office Action Dated Nov. 30, 2010 From the Israel Patent Office Re. Application No. 204766 and Its Translation Into English.
Official Action Dated Jun. 1, 2006 From the US Patent and Trademark Office Re.: U.S. Appl. No. 09/808,382.
Official Action Dated May 3, 2004 From the US Patent and Trademark Office Re.: U.S. Appl. No. 09/970,543.
Official Action Dated Oct. 5, 2007 From the US Patent and Trademark Office Re.: U.S. Appl. No. 09/808,382.
Official Action Dated Jan. 11, 2010 From the US Patent and Trademark Office Re.: U.S. Appl. No. 12/157,864.
Official Action Dated Dec. 13, 2007 From the US Patent and Trademark Office Re.: U.S. Appl. No. 11/238,574.
Official Action Dated Jul. 14, 2011 From the US Patent and Trademark Office Re.: U.S. Appl. No. 12/157,864.
Official Action Dated May 15, 2009 From the US Patent and Trademark Office Re.: U.S. Appl. No. 12/157,864.
Official Action Dated Dec. 16, 2009 From the US Patent and Trademark Office Re.: U.S. Appl. No. 09/970,543.
Official Action Dated Jan. 16, 2003 From the US Patent and Trademark Office Re.: U.S. Appl. No. 09/808,382.
Official Action Dated May 16, 2007 From the US Patent and Trademark Office Re.: U.S. Appl. No. 11/049,830.
Official Action Dated Aug. 17, 2010 From the US Patent and Trademark Office Re.: U.S. Appl. No. 12/367,075.
Official Action Dated Nov. 17, 2008 From the US Patent and Trademark Office Re.: U.S. Appl. No. 11/049,830.
Official Action Dated Sep. 19, 2002 From the US Patent and Trademark Office Re.: U.S. Appl. No. 09/808,382.
Official Action Dated Jan. 20, 2010 From the US Patent and Trademark Office Re.: U.S. Appl. No. 12/367,075.
Official Action Dated Feb. 21, 2008 From the US Patent and Trademark Office Re.: U.S. Appl. No. 11/049,830.
Official Action Dated Nov. 21, 2005 From the US Patent and Trademark Office Re.: U.S. Appl. No. 09/808,382.
Official Action Dated Feb. 23, 2005 From the US Patent and Trademark Office Re.: U.S. Appl. No. 09/808,382.
Official Action Dated Jun. 26, 2008 From the US Patent and Trademark Office Re.: U.S. Appl. No. 09/808,382.
Official Action Dated Dec. 27, 2010 From the US Patent and Trademark Office Re.: U.S. Appl. No. 12/367,075.
Official Action Dated Dec. 29, 2006 From the US Patent and Trademark Office Re.: U.S. Appl. No. 09/808,382.
Official Action Dated Jul. 29, 2004 From the US Patent and Trademark Office Re.: U.S. Appl. No. 09/808,382.
Partial European Search Report Dated Nov. 20, 2003 From the European Patent Office Re. Application No. 02256974.3.
Requisition by the Examiner Dated Aug. 3, 2010 From the Canadian Intellectual Property Office Re.: Application No. 2,403,000.
Requisition by the Examiner Dated May 3, 2010 From the Canadian Intellectual Property Office Re. Application No. 2,406,610.
Requisition by the Examiner Dated Feb. 16, 2009 From the Canadian Intellectual Property Office Re.: Application No. 2,403,000.
Requisition by the Examiner Dated Jul. 29, 2011 From the Canadian Intellectual Property Office Re. Application No. 2,406,610.
Response Dated Feb. 1, 2011 to Requisition by the Examiner of Aug. 3, 2010 From the Canadian Intellectual Property Office Re.: Application No. 2,403,000.
Response Dated May 5, 2011 to Communication Pursuant to Article 94(3) EPC of Nov. 10, 2010 From the European Patent Office Re.: Application No. 01911277.0.
Response Dated Aug. 9, 2009 to Requisition by the Examiner of Feb. 16, 2009 From the Canadian Intellectual Property Office Re.: Application No. 2,403,000.
Response Dated May 10, 2010 to Official Action of Jan. 11, 2010 From the US Patent and Trademark Office Re.: Application No. 12/157,864.
Response Dated Oct. 10, 2011 to Official Action Dated Jul. 14, 2011 From the US Patent and Trademark Office Re.: U.S. Appl. No. 12/157,864.
Response Dated May 11, 2010 to Office Action Dated Nov. 24, 2009 From the Israel Patent Office Re.: Application No. 152106.
Response Dated May 11, 2010 to Office Action of Nov. 24, 2009 From the Israel Patent Office Re.: Application No. 152106.
Response Dated Jul. 15, 2010 to Communication Pursuant to Article 94(3) EPC of Feb. 1, 2010 From the European Patent Office Re. Application No. 01911277.0.
Response Dated Oct. 15, 2009 to Office Action of Jun. 15, 2009 From the Israeli Patent Office Re.: Application No. 151170.
Response Dated Dec. 16, 2010 to Official Action of Aug. 17, 2010 From the US Patent and Trademark Office Re.: U.S. Appl. No. 12/367,075.
Response Dated Feb. 16, 2011 to Office Action of Dec. 3, 2010 From the Japanese Patent Office Re. Application No. 2001-567299.
Response Dated Aug. 18, 2008 to Official Action of Feb. 21, 2008 From the US Patent and Trademark Office Re.: U.S. Appl. No. 11/049,830.
Response Dated Jun. 18, 2010 to Official Action of Jan. 20, 2010 From the US Patent and Trademark Office Re.: U.S. Appl. No. 12/367,075.
Response Dated Nov. 22, 2010 to Office Action of Jul. 21, 2010 From the Japanese Patent Office Re. Application No. 2008-101883.
Response Dated Oct. 26, 2010 to Requisition by the Examiner of May 3, 2010 From the Canadian Intellectual Property Office Re. Application No. 2,406,610.
Response Dated Mar. 29, 2011 to Office Action of Nov. 30, 2010 From the Israel Patent Office Re. Application No. 204766.
Response Under 37 C.F.R. §1.111 Dated May 10, 2010 to Official Action of Jan. 11, 2010 From the US Patent and Trademark Office Re.: U.S. Appl. No. 12/157,864.
Response Under 37 C.F.R. §1.111 Dated Jun. 18, 2010 to Official Action of Jan. 20, 2010 From the US Patent and Trademark Office Re.: U.S. Appl. No. 12/367,075.
Search Report and Written Opinion Dated Feb. 2, 2007 From the Intellectual Property Office of Singapore Issued by the Austrian Patent Office Re.: Application No. 200206039-0.
Second Written Opinion Dated Nov. 16, 2007 From the Intellectual Property Office of Singpore Issued by the Austrian Patent Office Re.: Application No. 200206039-0.
Supplementary Partial European Search Report Dated May 7, 2004 From the European Patent Office Re.: Application No. 01911277.0.
Translation of Decision of Rejection Dated Apr. 5, 2011 From the Japanese Patent Office Re. Application No. 2008-101883.
Translation of Office Action Dated Dec. 3, 2010 From the Japanese Patent Office Re. Application No. 2001-567299.
Translation of Office Action Dated Jul. 21, 2010 From the Japanese Patent Office Re. Application No. 2008-101883.
Translation of the Office Action Dated Jun. 1, 2007 From the Japanese Patent Office Re.: Application No. 2002-292682.
Translation of the Office Action Dated Jun. 24, 2003 From the Japanese Patent Office Re.: Application No. 2002-292682.
Written Opinon Dated Oct. 25, 2001 From the International Preliminary Examining Authority Re.: Application No. PCT/AU01/00278.
Anderson et al. "Can Stem Cells Cross Lineage Boundaries?", Nature Medicine, 7(4): 393-395, 2001.
Assady et al. "Insulin Production by Human Embryonic Stem Cells", Diabetes, 50: 1691-1697, 2001.

Bäumer et al. "Pax6 Is Required for Establishing Naso-Temporal and Dorsal Characteristics of the Optic Vesicle", Development, 129: 4535-4545, 2002.
Beddington et al. "An Assessment of the Developmental Potential of Embryonic Stem Cells in the Midgestation Mouse Embryo", Development, 105: 733-737, 1989.
Ben-Hur et al. "Growth and Fate of PSA-NCAM+ Precursors of the Postnatal Brain", The Journal of Neuroscience, 18(15) 5777-5788, 1998.
Ben-Hur et al. "Transplantation of Human Embryonic Stem Cell-Derived Neural Progenitors Improves Behavioral Deficit in Parkinsonian Rats", Stem Cells, 22: 1246-1255, 2004.
Bhattacharya et al. "Gene Expression in Human Embryonic Stem Cell Lines: Unique Molecular Signature", Blood, 103(8): 2956-2964, 2004.
Bhattacharyya et al. "Human Neural Stem Cells: A New Tool for Studying Cortical Development in Down's Syndrome", Gene Brain Behavior, 2(3): 179-186, 2003. Abstract.
Brüstle et al. "Embryonic Stem Cell-Derived Glial Precursors: A Source of Myelinating Transplants", Science, XP002907880, 285: 754-756, 1999.
Carpenter et al. "In Vitro Expansion of a Multipotent Population of human Neural Progenitor Cells", Experimental Neurology, 158: 265-278, 1999.
Cattaneo et al. "Signalling Through the JAK-STAT Pathway in the Developing Brain", Trends in Neuroscience, 22(8): 365-369, 1999.
Centre for Cancer Education "Trophoblast", Dictionary of Cell and Molecular Biology, Centre for Cancer Education, University of Newcastle Upon Tyne, Retrieved From the Internet, 2006.
Clarke et al. "Generalized Potential of Adult Neural Stem Cells", Science, 288(5471): 1660-1663, 2000.
Cremer et al. "NCAM Is Essential for Axonal Growth and Fasciculation in the Hippocampus", Molecular and Cellular Neuroscience, 8: 323-335, 1997.
D'Amour et al. "Genetic and Functional Differences Between Multipotent Neural and Pluripotent Embryonic Stem Cells", Proc. Natl. Acad. Sci. USA, Early Ed., 7 P., 2002.
De la Maza et al. "Inhibition of Adenovirus Oncogenicity in Hamsters by Adeno-Associated Virus DNA", Journal of the National Cancer Institut, JNCI, 67(6): 1323-1326, 1981.
Doetschman et al. "The In Vitro Development of Blastocyst-Derived Embryonic Stem Cell Lines: Formation of Visceral Yolk Sac, Blood Islands and Myocardium", Journal of Embryology and Experimental Morphology, 87: 27-45, 1985.
Flax et al. "Engraftable Human Neural Stem Cells Respond to Developmental Cues, Replace Neurons, and Express Foreign Genes", Nature Biotechnology, 16: 1033-1039, 1998.
Fricker et al. "Site-Specific Migration and Neuronal Differentiation of Human Neural Progenitor Cells After Transplantation in the Adult Rat Brain", The Journal of Neuroscience, 19(14): 5990-6005, Jul. 15, 1999.
Gardner "Pluripotent Stem Cells From Vertebrate Embryos: Present Perspective and Future Challenges", Handbook of Stem Cells (Embryonic Stem Cells), Academic Press, 1: 15-22, 2004.
Ginis et al. "Differences Between Human and Mouse Embryonic Stem Cells", Developmental Biology, 269: 360-380, 2004.
Heng et al. "The Cryopreservation of Human Embryonic Stem Cells", Biotechnology and Applied Biochemistry, 41: 97-104, 2005.
Itskovitz-Eldor et al. "Differentiation of Human Embryonic Stem Cells Into Embryoid Bodies Comprising the Three Embryonic Germ Layers", Molecular Medicine, 6(2): 88-95, 2000.
Johansson et al. "Neural Stem Cells in the Adult Human Brain", Experimental Cell Research, 253: 733-736, 1999.
Keller "In Vitro Differentiation of Embryonic Stem Cells", Current Opinion in Cell Biology, 7: 862-869, 1995.
Kennea et al. "Neural Stem Cells", Journal of Pathology, 197: 536-550, 2002.
Kennea et al. "Transdifferentiation of Neural Stem Cells, or Not?", Pediatry Research, 52(3): 320-321, 2002.
Kettani et al. "Solution Structure of A Na Cation Stabilized DNA Quadruplex Containing G . G . G and G . C . G . C Tetrads Formed by G—G—G—C Repeats Observed in Adeno-Associated Viral DNA", Journal of Molecular Biology, 282: 619-636, 1998.

Kim et al. "Dopamine Neurons Derived From Embryonic Stem Cells Function in an Animal Model of Parkinson's Disease", Nature, 418: 50-56, 2002.
Lake et al. "Reversible Programming of Pluripotent Cell Differentiation", Journal of Cell Science, 113: 555-566, 2000.
Lanza et al. "Identification and Maintenance of Neural Prescursors From Human Embryonic Stem Cells: Other Potential Renewable Sources of Human Neural Precursors", Handbook of Stem Cells (Embryonic Stem Cells), Academic Press, 1: 513, 2004.
Lee et al. "Efficient Generation of Midbrain and Hindbrain Neurons From Mouse Embryonic Stem Cells", Nature Biotechnology, 18: 675-679, 2000.
Li et al. "Generation of Purified Neural Precursors From Embryonic Stem Cells by Lineage Selection", Current Biology, XP002112127, 8(17): 971-974, Aug. 27, 1998.
Li et al. "Specification of Motoneurons From Human Embryonic Stem Cells", Nature Biotechnology, Advanced Online Publication, 7 P., 2005.
Liu et al. "Glial Progenitors in the CNS and Possible Lineage Relationship Among Them", Biology of the Cell, 12 P., 2004.
Ma et al. "Cell-Extracellular Matrix Interactions Regulate Neural Differentiation of Human Embryonic Stem Cells", BMC Developmental Biology, 8(90): 1-13, Sep. 22, 2008.
Martinez-Serrano et al. "CNS-Derived Neural Progenitor Cells for Gene Transfer of Nerve Growth Factor to the Adult Rat Brain: Complete Rescue of Axotomized Cholinergic Neurons After Transplantation Into the Septum", The Journal of Neuroscience, 15(8): 5668-5680, 1995.
Mizuseki et al. "Generation of Neural Crest-Derived Peripheral Neurons and Floor Plate Cells From Mouse and Primate Embryonic Stem Cells", Proc. Natl. Acad. Sci. USA, 100(10): 5828-5833, 2003.
Moreadith et al. "Gene Targeting in Embryonic Stem Cells: The New Physiology and Metabolism", Journal of Molecular Medicine, 75:208-216, 1997.
Mujtaba et al. "Lineage-Restricted Neural Precursors Can Be Isolated From Both the Mouse Neural Tube and Cultured ES Cells", Developmental Biology, XP002216609, 214(1): 113-127, Oct. 1, 1999. P.115, 1-h Col., Paragraph 5, p. 121-127.
Mullins et al. "Molecular Medicine in Genetically Engineered Animals. Transgenesis in the Rat and Larger Mammals", Journal of Clinical Investigation, 97(7): 1557-1560, 1996.
Nakagawa et al. "Roles of Cell-Autonomous Mechanisms for Differential Expression of Region-Specific Transcription Factors in Neuroepithelial Cells", Development, 122: 2449-2464, 1996.
NIH "Glossary and Terms", NIH's Stem Cells Scientific Progress and Future Research Directions, Appendix F, P.F-1-F-12, 2001.
Niwa et al. "Self-Renewal of Pluripotent Embryonic Stem Cells Is Mediated Via Activation of STAT3", Genes & Development, 12: 2048-2060, 1998.
Okabe et al. "Development of Neuronal Precursor Cells and Functional Postmitotic Neurons From Embryonic Stem Cells In Vitro", Mechanisms of Development, 59(1): 89-102, 1996.
Ostenfeld et al. "Recent Advances in Stem Cell Neurobiology", Advanced Technology in Standard Neurosurgery, 28: 3-89, 2003. Abstract.
Ostenfeld et al. "Regional Specification of Rodent and Human Neurospheres", Developmental Brain Research, 134: 43-55, 2002.
Pedersen "Studies of In Vitro Differentiation With Embryonic Stem Cells", Reproduction, Fertility and Development, XP000197830, 6(5): 543-552, 1994.
Pera et al. "Human Embryonic Stem Cells", Journal of Cell Science, 113: 5-10, 2000.
Rao "Stem and Precursor Cells in the Nervous System", Journal of Neurotrauma, 21(4): 415-427, 2004.
Rao et al. "Gene Expression Profiling of Embryonic Stem Cells Leads to Greater Understanding of Pluripotent and Early Developmental Events", Biology of Reproduction, 71: 1772-1778, 2004.
Rathjen et al. "Properties and Uses of Embryonic Stem Cells: Prospects for Application to Human Biology and Gene Therepy", Reproduction, Fertility and Development, XP000916997, 10(1): 31-47, 1998.

Reubinoff et al. "Embryonic Stem Cell Lines From Human Blastocytes: Somatic Differentiation In Vitro", Nature Biotechnology, XP002195338, 18(4): 399-404, 2000. p. 403, col. 2.
Reubinoff et al. "Neural Progenitors From Human Embryonic Stem Cells", Nature Biotechnology, 19: 1134-1140, 2001.
Reynolds et al. "Generation of Neurons and Astrocytes From Isolated Cells of the Adult Mammalian Central Nervous System", Science, 255(5052): 1707-1710, 1992.
Robertson "NIC Sacrifices Commercial Rights in WiCell Deal", Nature Biotechnology, 19: 1001, Nov. 2001.
Rossi et al. "Neurologic Diseases: Sources of Stem Cells for Brain Repair", Handbook of Stem Cells (Adult and Fetal Stem Cells), Academic Press, 2: 696-697, 2004.
Sato et al. "Molecular Signature of Human Embryonic Stem Cells and Its Comparison With the Mouse", Developmental Biology, 260: 404-413, 2003.
Satoh et al. "Ganglioside Markers GD3, GD2, and A2B5 in Fetal Human Neurons and Glial Cells in Culture", Developmental Neuroscience, 17(3): 137-148, 1995.
Schuldiner et al. "Effects of Eight Growth Factors on the Differentiation of Cells Derived From Human Embryonic Stem Cells", Proc. Natl. Acad. Sci. USA, 97(21): 11307-11312, 2000.
Shamblott et al. "Derivation of Pluripotent Stem Cells From Cultured Human Primordial Germ Cells", Proc. Natl. Acad. Sci. USA, 95: 13726-13731, 1998.
Stemple et al. "Isolation of a Stem Cell for Neurons and Glia From the Mammalian Neural Crest", Cell, 71(6): 973-985, 1992.
Studer "Nervous System: Neural Stem Cells", Handbook of Stem Cells (Embryonic Stem Cells), 1: 238-239, 2004.
Svendsen "Stem Cells", In: A Companion to Genethics, Blackwell Press, Prepublished Version, 16 P., 2002.
Svendsen et al. "Human Neural Stem Cells: Isolation, Expansion and Transplantation", Brain Pathology, 9: 499-513, 1999.
Svendsen et al. "Increased Survival of Rat EGF-Generated CNS Precursor Cells Using B27 Supplemented Medium", Experimental Brain Research, 102: 407-414, 1995.
Svendsen et al. "New Prospects for Human Stem-Cell Therapy in the Nervous System", Trends in Neuroscience, XP001030096, 22(8):357-364, 1999.
Temple "The Development of Neural Stem Cells", Nature, 414: 112-117, 2001.
Thomson et al. "Embryonic Stem Cell Lines Derived From Human Blastocytes", Science, XP002933311, 282: 1145-1147, Nov. 6, 1998.
Thomson et al. "Neural Differentiation of Rhesus Embryonic Stem Cells", Acta Pathologica, Microbiologica et Immunologica Scandinavica, APMIS, XP002933310, 106(1): 149-157, 1998. Abstract.
Thomson et al. "Primate Embryonic Stem Cells", Current Topics in Development Biology, 38: 133-165, 1998.
Tropepe et al. "Direct Neural Fate Specification From Embryonic Stem Cells: A Primitive Mammalian Neural Stem Cell Stage Acquired Through a Default Mechanism", Neuron, 30: 65-78, 2001.
Uchida et al. "Direct Isolation of Human Central Nervous System Stem Cells", Proc. Natl. Acad. Sci. USA, 97(26): 14720-14725, 2000.
Van Inzen et al. "Neuronal Differentiation of Embryonic Stem Cells", Biochimica et Biophysica Acta, 1312: 21-26, 1996.
Verfaillie et al. "Stem Cells: Hype and Reality", Hematology, p. 369-391, 2002.
Vescovi et al. "Isolation and Cloning of Multipotential Stem Cells From the Embryonic Human CNS and Establishment of Transplantable Human Neural Stem Cell Lines by Epigenetic Stimulation", Experimental Neurology, 156: 71-78, 1999.
Vogel "NIH Guidelines: Researchers Get Green Light Light for Work on Stem Cells", Science, 289(5484): 1442-1443, Sep. 1, 2000.
Vogel "Stem Cells: Wisconsin to Distribute Embryonic Cell Lines", Science, 287(5455): 948-949, Feb. 11, 2000.
Wang et al. "Nestin Expression and Clonal Analysis of Islet-Derived Epithelial Monolayers: Insight Into Nestin-Expressing Cell Heterogeneity and Differentiation Potential", Journal of Endocrinology, 184: 329-339, 2005.
Wolf et al. "Progress With Nonhuman Primate Embryonic Stem Cells", Biology of Reproduction, 71: 1766-1771, 2004.
Wright et al. "Gene Expression in Human Neural Stem Cells: Effects of Leukemia Inhibitory Factor", Journal of Neurochemistry, 86: 179-195, 2003.
Xu et al. "BMP4 Initiates Human Embryonic Stem Cell Differentiation to Trophoblast", Nature Biotechnology, 20: 1261-1264, 2002.
Xu et al. "Characterization and Enrichment of Cardiomyocytes Derived From Human Embryonic Stem Cells", Circulation Research, 91: 501-508, 2002.
Zwaka et al. "A Germ Cell Origin of Embryonic Stem Cells?", Development, 132: 227-233, 2005.
Requisition by the Examiner Dated Jan. 18, 2012 From the Canadian Intellectual Property Office Re.: Application No. 2,403,000.
Official Action Dated Apr. 6, 2012 From the US Patent and Trademark Office Re. U.S. Appl. No. 13/095,961.
King "Growth Factors and Cytokines", The Medical Biochemistry Page, p. 1-9, Mar. 10, 2012.
European Search Report and the European Search Opinion Dated Mar. 28, 2012 From the European Patent Office Re. Application No. 12154239.3.
Communication Pursuant to Rules 70(2) and 70a(2) EPC and Reference to Rule 39(1) EPC Dated May 22, 2012 From the European Patent Office Re. Application No. 12154239.3.
Communication Pursuant to Article 94(3) EPC Dated Sep. 27, 2012 From the European Patent Office Re. Application No. 01911277.0.

* cited by examiner

Figure 1
Fig. 1A 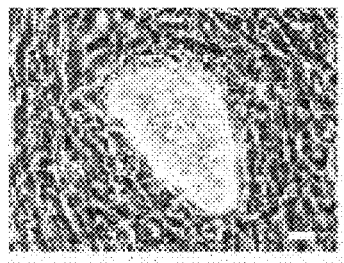 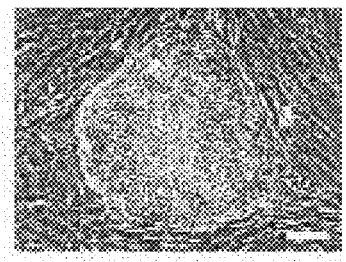 Fig. 1B
Fig. 1C 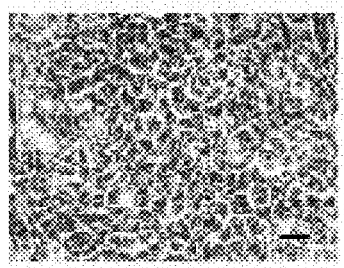 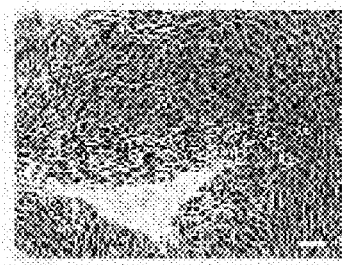 Fig. 1D
Fig. 1E 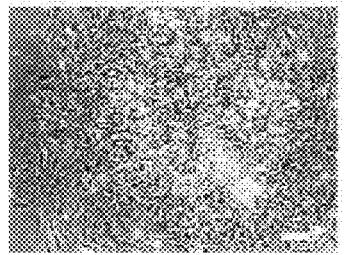 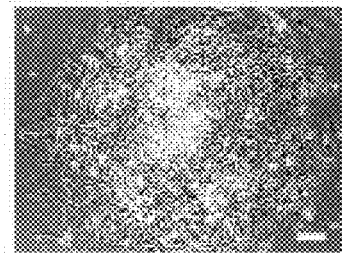 Fig. 1F Figure 2
Fig. 2A
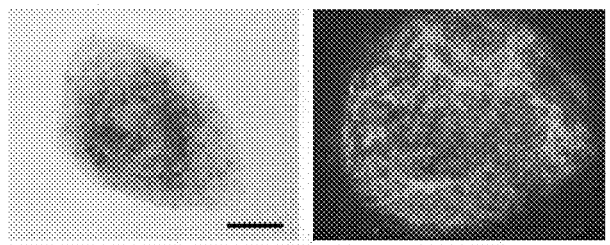
Fig. 2B
Fig. 2C
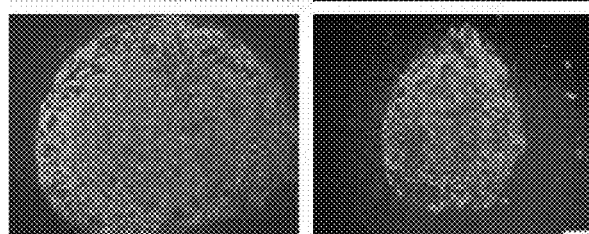
Fig. 2D
Fig. 2E
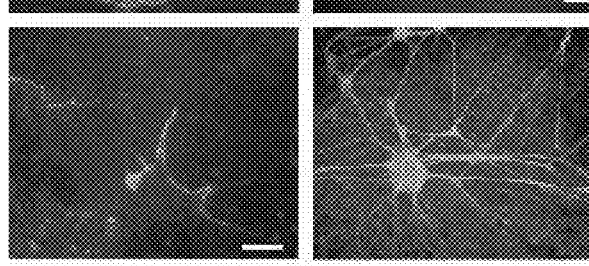
Fig. 2F
Fig. 2G
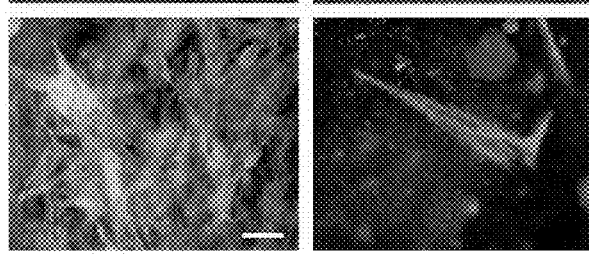
Fig. 2H FIGURE 3
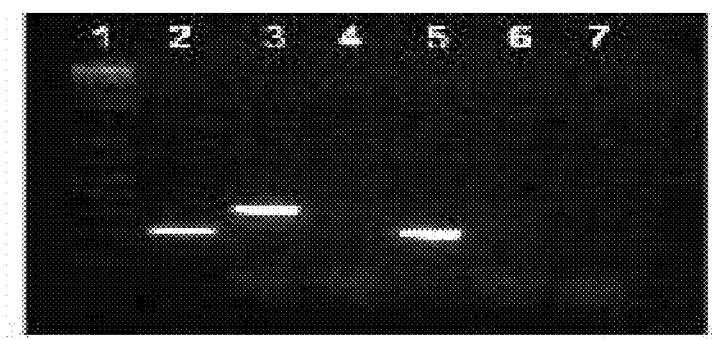
Fig. 3A
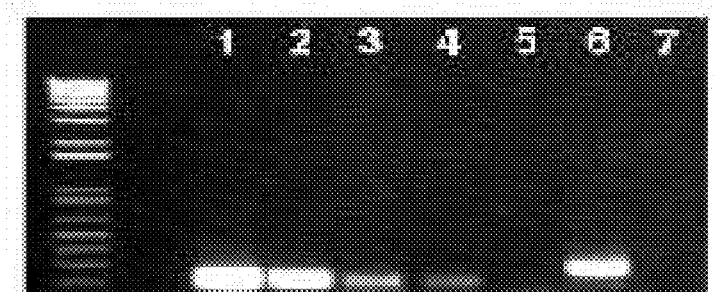
Fig. 3B
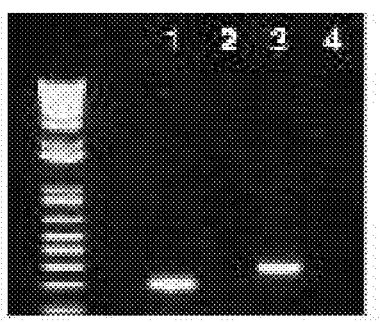
Fig. 3C
Fig. 3D Figure 4
Fig. 4A 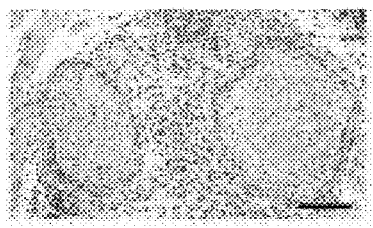 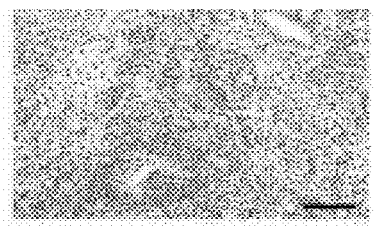 Fig. 4B
Fig. 4C 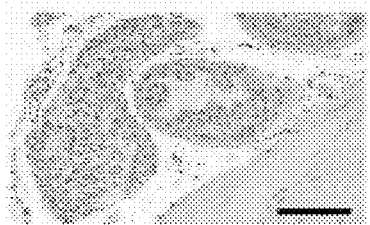  Fig. 4D
Fig. 4E  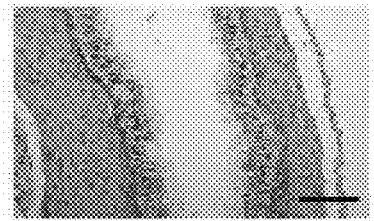 Fig. 4F

Figure 5

V – lateral ventricle; RMS – Rostral migratory stream

Figure 29
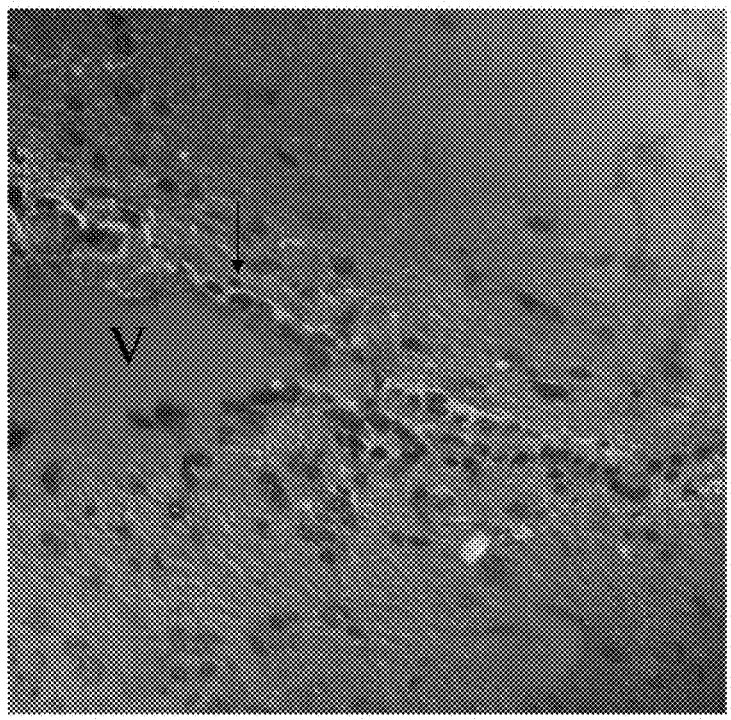
Fig. 29A
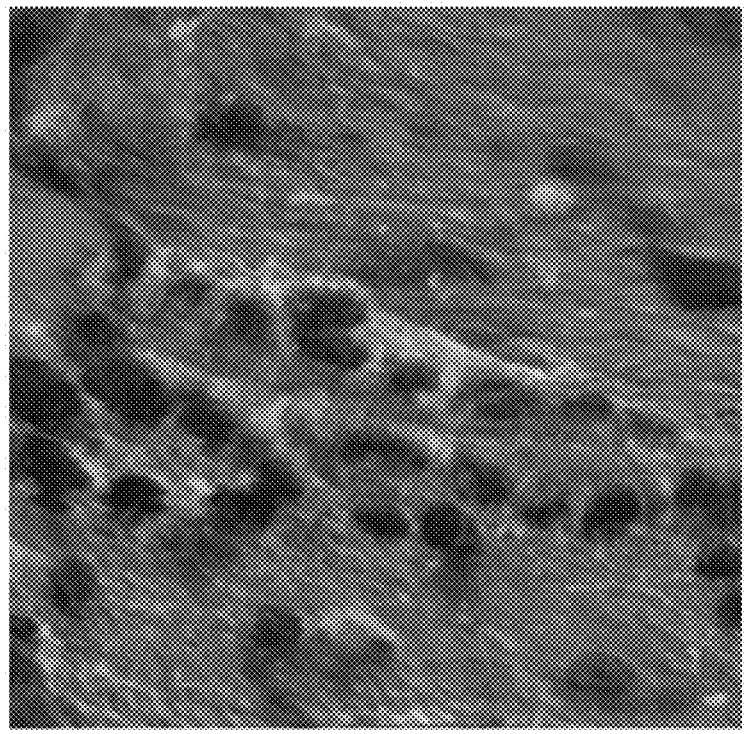
Fig. 29B

A.

B.

SEQUENCE LISTING

<160> NUMBER OF SEQ ID NOS: 32

<210> SEQ ID NO 1
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 1
aacagacaca gccctcacaa aca                                            23

<210> SEQ ID NO 2
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 2
cgggaacttg aactggaact gac                                            23

<210> SEQ ID NO 3
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 3
cagctggcgc acctcaagat g                                              21

<210> SEQ ID NO 4
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 4
agggaagttg ggctcaggac tgg                                            23

<210> SEQ ID NO 5
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 5
cgttctcttt ggaaaggtgt tc                                             22

<210> SEQ ID NO 6
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 6
acactcggac cacgtctttc                                                20

<210> SEQ ID NO 7
<211> LENGTH: 20
<212> TYPE: DNA

```
<213> ORGANISM: Artificial Sequence
<220> FEATURE:
<223> OTHER INFORMATION: synthetic oligonucleotide

<400> SEQUENCE: 7
cgcaccactg gcattgtcat                                                    20

<210> SEQ ID NO 8
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 8
ttctccttga tgtcacgcac                                                    20

<210> SEQ ID NO 9
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 9
tcaccaccac ggccgagcg                                                     19

<210> SEQ ID NO 10
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 10
tctccttctg catcctgtcg                                                    20

<210> SEQ ID NO 11
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 11
tgaagcctag cctgtcacct                                                    20

<210> SEQ ID NO 12
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 12
cgcacagctg gaggtcttat                                                    20

<210> SEQ ID NO 13
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 13
ggtattggca gttggaggaa                                                    20
```

-continued

<210> SEQ ID NO 14
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 14
acatttgccg cttggataac                                              20

<210> SEQ ID NO 15
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 15
cagtctgacc agcgtgaaaa                                              20

<210> SEQ ID NO 16
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 16
ggccatccaa atctgtccta                                              20

<210> SEQ ID NO 17
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 17
gagtttacag gcttgtggca                                              20

<210> SEQ ID NO 18
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 18
gagggcaatt cctgaggatt                                              20

<210> SEQ ID NO 19
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 19
ccatgtacat gagcactgtt g                                            21

<210> SEQ ID NO 20
<211> LENGTH: 21
<212> TYPE: DNA
<213> ORGANISM: Artificial Sequence
<220> FEATURE:
<223> OTHER INFORMATION: synthetic oligonucleotide

```
<400> SEQUENCE: 20
ctccaataac tcctgctatc c                                        21

<210> SEQ ID NO 21
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 21
ctgacctcac ctgggacaat                                          20

<210> SEQ ID NO 22
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 22
ccatcaaggc acagcaactc                                          20

<210> SEQ ID NO 23
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 23
gctgggctca gtattcccca aatac                                    25

<210> SEQ ID NO 24
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 24
gacgacaatc tctgacctga gtagc                                    25

<210> SEQ ID NO 25
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 25 agacccttg aagtcaagga caccg                                     25

<210> SEQ ID NO 26
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 26
ccattgctga agaccttagt gatgc                                    25

<210> SEQ ID NO 27
<211> LENGTH: 25
<212> TYPE: DNA
```

<213> ORGANISM: Artificial Sequence
<220> FEATURE:
<223> OTHER INFORMATION: synthetic oligonucleotide

<400> SEQUENCE: 27
aggaaatcat ctcaggagga agggc                                      25

<210> SEQ ID NO 28
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 28
aaagcacaga tcttcgggag ctacc                                      25

<210> SEQ ID NO 29
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 29
tcatcgctca ggaggtcctt                                            20

<210> SEQ ID NO 30
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 30
ctgttgccag agatggaggt t                                          21

<210> SEQ ID NO 31
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 31
ccatgccttc cagtatgtca tc                                         22

<210> SEQ ID NO 32
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 32
gtggtccagg tgttgaagta aatgt                                      25

NEURAL PROGENITOR CELLS DERIVED FROM EMBRYONIC STEM CELLS

CROSS-REFERENCE TO RELATED APPLICATIONS

This application is a divisional of U.S. patent application Ser. No. 12/157,864 filed on Jun. 13, 2008, now U.S. Pat. No. 8,137,969, which is a continuation of U.S. patent application Ser. No. 11/238,574 filed on Sep. 29, 2005, now abandoned, which is a continuation of U.S. patent application Ser. No. 09/970,543 filed on Oct. 4, 2001, now U.S. Pat. No. 7,011,828, which is a continuation-in-part of U.S. patent application Ser. No. 09/808,382 filed on Mar. 14, 2001, now U.S. Pat. No. 7,504,257, which claims the benefit of priority from Australia Patent Application Nos. PR2920 filed on Feb. 6, 2001, PR1279 filed on Nov. 6, 2000 and PQ6211 filed on Mar. 14, 2000. The contents of all of the above applications are incorporated by reference as if fully set forth herein.

The present invention relates to undifferentiated human embryonic stem cells, methods of cultivation and propagation and production of differentiated cells. In particular it relates to the production of human ES cells capable of yielding somatic differentiated cells in vitro, as well as committed progenitor cells such as neural progenitor cells capable of giving rise to mature somatic cells including neural cells and/or glial cells and uses thereof.

INTRODUCTION

The production of human embryonic stem cells which can be either maintained in an undifferentiated state or directed to undergo differentiation into extraembryonic or somatic lineages in vitro allows for the study of the cellular and molecular biology of early human development, functional genomics, generation of differentiated cells from the stem cells for use in transplantation or drug screening and drug discovery in vitro.

In general, stem cells are undifferentiated cells which can give rise to a succession of mature functional cells. For example, a haematopoietic stem cell may give rise to any of the different types of terminally differentiated blood cells. Embryonic stem (ES) cells are derived from the embryo and are pluripotent, thus possessing the capability of developing into any organ, cell type or tissue type or, at least potentially, into a complete embryo.

The development of mouse ES cells in 1981 (Evans and Kaufman, 1981; Martin, 1981) provided the paradigm, and, much of the technology, for the development of human ES cells. Development of ES cells evolved out of work on mouse teratocarcinomas, (tumours arising in the gonads of a few inbred strains), which consist of a remarkable array of somatic tissues juxtaposed together in a disorganised fashion. Classical work on teratocarcinomas established their origins from germ cells in mice, and provided the concept of a stem cell (the embryonal carcinoma or EC cell) which could give rise to the multiple types of tissue found in the tumours (Kleinsmith and Pierce, 1964; review, Stevens, 1983). The field of teratocarcinoma research (review, Martin, 1980) expanded considerably in the 70's, as the remarkable developmental capacity of the EC stem cell became apparent following the generation of chimaeric mice by blastocyst injection of EC cells, and investigators began to realise the potential value of cultured cell lines from the tumours as models for mammalian development. EC cells however had limitations. They often contained chromosomal abnormalities, and their ability to differentiate into multiple tissue types was often limited.

Since teratocarcinomas could also be induced by grafting blastocysts to ectopic sites, it was reasoned that it might be possible to derive pluripotential cell lines directly from blastocysts rather than from tumours, as performed in 1981 by Gail Martin and Martin Evans independently. The result was a stable diploid cell line which could generate every tissue of the adult body, including germ cells. Teratocarcinomas also develop spontaneously from primordial germ cells in some mouse strains, or following transplantation of primordial germ cells to ectopic sites, and in 1992 Brigid Hogan and her colleagues reported the direct derivation of EG cells from mouse primordial germ cells (Matsui et al., 1992). These EG cells have a developmental capacity very similar to ES cells.

Testicular teratocarcinomas occur spontaneously in humans, and pluripotential cell lines were also developed from these (review, Andrews, 1988). Two groups reported the derivation of cloned cell lines from human teratocarcinoma which could differentiate in vitro into neurons and other cell types (Andrews et al., 1984, Thompson et al., 1984). Subsequently, cell lines were developed which could differentiate into tissues representative of all three embryonic germ layers (Pera et al., 1989). As analysis of the properties of human EC cells proceeded, it became clear that they were always aneuploid, usually (though not always) quite limited in their capacity for spontaneous differentiation into somatic tissue, and different in phenotype from mouse ES or EC cells.

The properties of the pluripotent cell lines developed by Pera et al. (1989) are as follows:
- Express SSEA-3, SSEA-4, TRA 1-60, GCTM-2, alkaline phosphatase, Oct-4
- Grow as flat colonies with distinct cell borders Differentiate into derivatives of all three embryonic germ layers Feeder cell dependent (feeder cell effect on growth not reconstituted by conditioned medium from feeder cells or by feeder cell extracellular matrix)
- Highly sensitive to dissociation to single cells, poor cloning efficiency even on a feeder cell layer
- Do not respond to Leukemia Inhibitory Factor These studies of human EC cells essentially defined the phenotype of primate pluripotential stem cells.

Derivation of primate ES cells from the rhesus monkey blastocyst and later from that of the marmoset (Thomson et al., 1995, 1996) has been described. These primate cell lines were diploid, but otherwise they closely resembled their nearest counterpart, the human EC cell. The implication of the monkey work and the work on human EC cells was that a pluripotent stem cell, which would be rather different in phenotype from a mouse ES cell, could likely be derived from a human blastocyst.

Bongso and coworkers (1994) reported the short term culture and maintenance of cells from human embryos fertilised in vitro. The cells isolated by Bongso and coworkers had the morphology expected of pluripotent stem cells, but these early studies did not employ feeder cell support, and it was impossible to achieve long term maintenance of the cultures.

James Thomson and coworkers (1998) derived ES cells from surplus blastocysts donated by couples undergoing treatment for infertility. The methodology used was not very different from that used 17 years earlier to derive mouse ES stem cells. The trophectoderm, thought to be inhibitory to ES cell establishment, was removed by immunosurgery, the inner cell mass was plated on to a mouse embryonic fibroblast feeder cell layer, and following a brief period of attachment and expansion, the resulting outgrowth was disaggregated and replated onto another feeder cell layer. There were no significant departures from mouse ES protocols in the media or other aspects of the culture system and a relatively high success rate was achieved. The phenotype of the cells was similar to that outlined above in the human EC studies of Pera et al.

In the studies of Thomson et al. on monkey and human ES cells, there was no evidence that the cells showed the capacity for somatic differentiation in vitro. Evidence for in vitro differentiation was limited to expression of markers characteristic of trophoblast and endoderm formation (production of human chorionic gonadotrophin and alphafetoprotein). It is not possible to state whether the cells found producing alphafetoprotein represent extraembryonic (yolk sac) endoderm or definitive (embryonic) endoderm though the former is far more likely. Thus an essential feature for any human ES cell line to be of practical use, namely the production of differentiated somatic cells in vitro as seen in previous studies of human EC cells, was not demonstrated in the monkey or human ES cell studies.

Much attention recently has been devoted to the potential applications of stem cells in biology and medicine, the properties of pluripotentiality and immortality are unique to ES cells and enable investigators to approach many issues in human biology and medicine for the first time. ES cells potentially can address the shortage of donor tissue for use in transplantation procedures, particularly where no alternative culture system can support growth of the required committed stem cell. However, it must be noted that almost all of the wide ranging potential applications of ES cell technology in human medicine-basic embryological research, functional genomics, growth factor and drug discovery, toxicology, and cell transplantation are based on the assumption that it will be possible to grow ES cells on a large scale, to introduce genetic modifications into them, and to direct their differentiation. Present systems fall short of these goals, but there are indications of progress to come. The identification of novel factors driving pluripotential stem cell growth or stem cell selection protocols to eliminate the inhibitory influence of differentiated cells, both offer a way forward for expansion and cloning of human ES cells.

The mammalian nervous system is a derivative of the ectodermal germ layer of the postimplantation embryo. During the process of axis formation, it is thought that inductive signals elaborated by several regions of the embryo (the anterior visceral endoderm and the early gastrula organiser) induce the pluripotent cells of the epiblast to assume an anterior neural fate (Beddington and Robertson, 1999). The molecular identity of the factors elaborated by these tissues which direct neurogenesis is unknown, but there is strong evidence from lower vertebrates that antagonists of the Wnt and BMP families of signalling molecules may be involved.

Embryonic stem cells are pluripotent cells which are thought to correspond to the epiblast of the periimplantation embryo. Mouse ES cells are able to give rise to neural tissue in vitro either spontaneously or during embryoid body formation. The neural tissue often forms in these circumstances in amongst a mixture of a range of cell types. Alteration of the conditions of culture, or subsequent selection of neural cells from this mixture, has been used to produce relatively pure populations of neuronal cells from differentiating cultures of ES cells (eg Li et al., 1998). These neuronal cells have been used in experimental models to correct various deficits in animal model systems (review, Svendsen and Smith, 1999). The same has not yet been achieved with human ES cell derived neurons, though neuronal cells have been derived from human embryonal carcinoma cells which were induced to differentiate using retinoic acid. These EC cells were subsequently shown to correct deficits in experimental models of CNS disease.

A suitable source of human ES derived neurons would be desirable since their availability would provide real advantages for basic and applied studies of CNS development and disease. Controlled differentiation of human ES cells into the neural lineage will allow experimental dissection of the events during early development of the nervous system, and the identification of new genes and polypeptide factors which may have a therapeutic potential such as induction of regenerative processes. Additional pharmaceutical applications may include the creation of new assays for toxicology and drug discovery, such as high-throughput screens for neuroprotective compounds. Generation of neural progenitors from ES cells in vitro may serve as an unlimited source of cells for tissue reconstruction and for the delivery and expression of genes in the nervous system.

It is an object of the invention to overcome or at least alleviate some of the problems of the prior art.

SUMMARY OF THE INVENTION

In one aspect of the present invention, there is provided an enriched preparation of undifferentiated human embryonic stem cells capable of proliferation in vitro and differentiation to neural progenitor cells, neuron cells and/or glial cells.

Preferably the undifferentiated ES cells have the potential to differentiate into neural progenitor cells, neuron cells and/or glial cells when subjected to differentiating conditions.

More preferably, the undifferentiated ES cells are capable of maintaining an undifferentiated state when cultured on a fibroblast feeder layer.

In another aspect of the present invention there is provided an undifferentiated human embryonic stem cell wherein the cell is immunoreactive with markers for human pluripotent stem cells including SSEA-4, GCTM-2 antigen, TRA 1-60 and wherein said cell may differentiate under differentiating conditions to neural cells. Preferably, the cells express the transcription factor Oct-4 as demonstrated by RT-PCR. More preferably, the cells maintain a diploid karyotype during prolonged cultivation in vitro.

In another aspect there is provided an undifferentiated cell line capable of differentiation into neural progenitor cells, neurone cells and glial cells and preferably produced by a method of the present invention.

In another aspect there is provided a differentiated committed progenitor cell line that may be cultivated for prolonged periods and give rise to large quantities of progenitor cells.

In another aspect there is provided a differentiated committed progenitor cell line capable of differentiation into mature neurons and/or glial cells.

In another aspect, there is provided a neural progenitor cell, neuron cell and/or a glial cell differentiated in vitro from an undifferentiated embryonic stem cell. There is also provided a committed neural progenitor cell capable of giving rise to mature neuron cells and glial cells.

In another aspect there is provided a differentiated committed progenitor cell line capable of establishing a graft in a recipient brain, to participate in histogenesis of the nervous system and to constitute the neuronal, astrocyte and oligodendrocyte lineages in vivo.

Preferably, the undifferentiated cell line is preserved by preservation methods such as cryopreservation. Preferably the method of cryopreservation is a method highly efficient for use with embryos such as vitrification. Most preferably, the method includes the Open Pulled Straw (OPS) vitrification method.

In another aspect the neural progenitor cell line is preserved by preservation methods such as cryopreservation.

In another aspect, there is provided a neural progenitor cell capable of differentiating into glial cells, including astrocytes and oligodendrocytes.

In another aspect, there is provided a neural progenitor cell capable of transdifferentiation into other cell lineages, to generate stem cells and differentiated cells of non-neuronal phenotype, such as hemangioblast, hematopoietic stem cells, endothelial stem cells, embryonic endoderm and ectodermal cells.

In a further aspect of the present invention, there is provided a method of preparing undifferentiated human embryonic stem cells for differentiation into neural progenitor cells, said method including:
  obtaining an in vitro fertilised human embryo and growing the embryo to a blastocyst stage of development;
  removing inner cells mass (ICM) cells from the embryo;
  culturing ICM cells under conditions which do not induce extraembryonic differentiation and cell death and promote proliferation of undifferentiated cells; and
  recovering the stem cells.

In a further preferred embodiment of the present invention there is provided a method of preparing undifferentiated human embryonic stem cells for differentiation into neural progenitor cells, said method including:
  obtaining an in vitro fertilised human embryo;
  removing inner cell mass (ICM) cells from the embryo;
  culturing ICM cells on a fibroblast feeder layer to promote proliferation of embryonic stem cells; and
  recovering stem cells from the feeder layer.

In a further embodiment of the invention, the method further includes:
  replacing the stem cells from the fibroblast feeder layer onto another fibroblast feeder layer; and
  culturing the stem cells for a period sufficient to promote proliferation of morphologically undifferentiated stem cells.

In another aspect of the invention the method further includes propagating the undifferentiated stem cells.

In another aspect of the invention there is provided a method of inducing somatic differentiation of stem cells in vitro into progenitor cells said method comprising:
  obtaining undifferentiated stem cells; and
  providing a differentiating signal under conditions which are non-permissive for stem cell renewal, do not kill cells and induces unidirectional differentiation toward extraembryonic lineages.

In a preferred embodiment of the present invention, there is provided a method of inducing somatic differentiation of stem cells in vitro into progenitor cells, said method comprising:
  obtaining undifferentiated stem cells; and
  culturing said cells for a prolonged period and at high density on a fibroblast feeder cell layer to induce differentiation.

In another preferred embodiment of the present invention, there is provided a method of inducing somatic differentiation of stem cells in vitro into progenitor cells, said method comprising:
  obtaining undifferentiated stem cells; and
  transferring said cells into serum free media to induce differentiation.

In an additional aspect of the invention method may be used for directing stem cells to differentiate toward a somatic lineage. Furthermore, the method allows the establishment of a pure preparation of progenitor cells from a desired lineage and facilitate the establishment of a pure somatic progenitor cell line.

In another preferred embodiment of the present invention, there is provided a method of inducing the differentiation of ES derived neural progenitor cells into differentiated mature neuronal cells, and glial cells including oligodendrocyte and astrocyte cells.

This invention provides a method that generates an in vitro and in vivo model of controlled differentiation of ES cells towards the neural lineage. The model, and the cells that are generated along the pathway of neural differentiation may be used for the study of the cellular and molecular biology of human neural development, for the discovery of genes, growth factors, and differentiation factors that play a role in neural differentiation and regeneration, for drug discovery and for the development of screening assays for teratogenic, toxic and neuroprotective effects.

In a further aspect of the invention there is provided a neural progenitor cell, a neuronal cell and a glial cell that may be used for cell therapy and gene therapy.

FIGURES

The file of this patent contains at least one drawing executed in color. Copies of this patent with color drawing(s) will be provided by the Patent and Trademark Office upon request and payment of the necessary fee.

FIG. 1 shows phase contrast micrographs of ES cells and their differentiated progeny. A, inner cell mass three days after plating. B, colony of ES cells. C, higher magnification of an area of an ES cell colony. D, an area of an ES cell colony undergoing spontaneous differentiation during routine passage. E, a colony four days after plating in the absence of a feeder cell layer but in the presence of 2000 units/ml human LIF undergoing differentiation in its periphery. F, neuronal cells in a high density culture. Scale bars: A and C, 25 microns; B and E, 100 microns; D and F, 50 microns.

FIG. 2 shows marker expression in ES cells and their differentiated somatic progeny. A, ES cell colony showing histochemical staining for alkaline phosphatase. B, ES cell colony stained with antibody MC-813-70 recognising the SSEA-4 epitope. C, ES cell colony stained with antibody TRA1-60. D, ES cell colony stained with antibody GCTM-2. E, high density culture, cell body and processes of a cell stained with anti-neurofilament 68 kDa protein. F, high density culture, cluster of cells and network of processes emanating from them stained with antibody against neural cell adhesion molecule. G, high density culture, cells showing cytoplasmic filaments stained with antibody to muscle actin. H, high density culture, cell showing cytoplasmic filaments stained with antibody to desmin. Scale bars: A, 100 microns; B-D, and F, 200 microns; E, G and H, 50 microns.

FIG. 3 shows RT-PCR analysis of gene expression in ES cells and their differentiated derivatives. All panels show 1.5% agarose gels stained with ethidium bromide. A, expression of Oct-4 and b-actin in ES stem cells and high density cultures. Lane 1, 100 bp DNA ladder. Lane 2, stem cell culture, b-actin. Lane 3, stem cell culture, Oct-4. Lane 4, stem cell culture, PCR for Oct-4 carried out with omission of reverse transcriptase. Lane 5, high density culture, b-actin. Lane 6, high density culture, Oct-4. Lane 7, high density culture, PCR for Oct-4 carried out with omission of reverse transcriptase. b-actin band is 200 bp and Oct-4 band is 320 bp.

B, expression of nestin and Pax-6 in neural progenitor cells that were derived from differentiating ES colonies. Left lane, 100 bp DNA ladder; lane 1, b-actin in HX 142 neuroblastoma cell line (positive control for nestin PCR); lane 2, b-actin in neural progenitor cells; lane 3, nestin in HX 142 neuroblastoma cell line; lane 4, nestin in neural progenitor cells; lane 5, nestin PCR on same sample as lane 4 without addition of reverse transcriptase; lane 6, Pax-6; lane 7, Pax-6 PCR on same sample as line 6 without addition of reverse transcriptase. Nestin band is 208 bp, Pax-6 is 274 bp. C, expression of glutamic acid decarboxylase in cultures of neurons. Left lane, 100 bp DNA ladder; lane 1, b-actin; lane 2, b-actin PCR on same sample as lane 1 without addition of reverse transcriptase; lane 3, glutamic acid decarboxylase; lane 4 glutamic acid decarboxylase on same sample as lane 3 without addition of reverse transcriptase. Glutamic acid decarboxylase band is 284 bp. D, expression of GABA Aα2 receptor. Left lane, 100 bp DNA ladder; lane 1, b-actin; lane 2, GABA Aα2 receptor; lane 3, PCR without addition of reverse transcriptase. GABA Aα2 receptor subunit band is 471 bp.

FIG. 4 shows histology of differentiated elements found in teratomas formed in the testis of SCID mice following inoculation of HES-1 or HES-2 colonies. A, cartilage and squamous epithelium, HES-2. B, neural rosettes, HES-2. C, ganglion, gland and striated muscle, HES-1. D, bone and cartilage, HES-1. E, glandular epithelium, HES-1. F, ciliated columnar epithelium, HES-1. Scale bars: A-E, 100 microns; F, 50 microns.

FIG. 5 shows phase contrast microscopy and immunochemical analysis of marker expression in neural progenitor cells isolated from differentiating ES cultures. A, phase contrast image of a sphere formed in serum-free medium. B-D, indirect immunofluorescence staining of spheres, 4 hours after plating on adhesive substrate, for N-CAM, nestin, and vimentin respectively. In C and D, cells at the base of the sphere were placed in plane of focus to illustrate filamentous staining; confocal examination revealed that cells throughout the sphere were decorated by both antibodies. Scale bar is 100 microns in all panels.

FIG. 6 shows phase contrast appearance and marker expression in cultures of neurons derived from progenitor cells shown in FIG. 5. A, phase contrast micrograph of differentiated cells emanating from a sphere plated onto adhesive surface. B-H, indirect immunofluorescence microscopy of differentiated cells decorated with antibodies against 200 kDa neruofilament protein (B), 160 kDa neurofilament protein (C), MAP2a+b (D), glutamate (E), synaptophysin (F), glutamic acid decarboxylase (G) and β-tubulin (H). Scale bars: A, B, 100 microns; C, 200 mircons; D, 20 microns; E and F, 10 microns; G, 20 microns; H, 25 microns.

Figure 12:
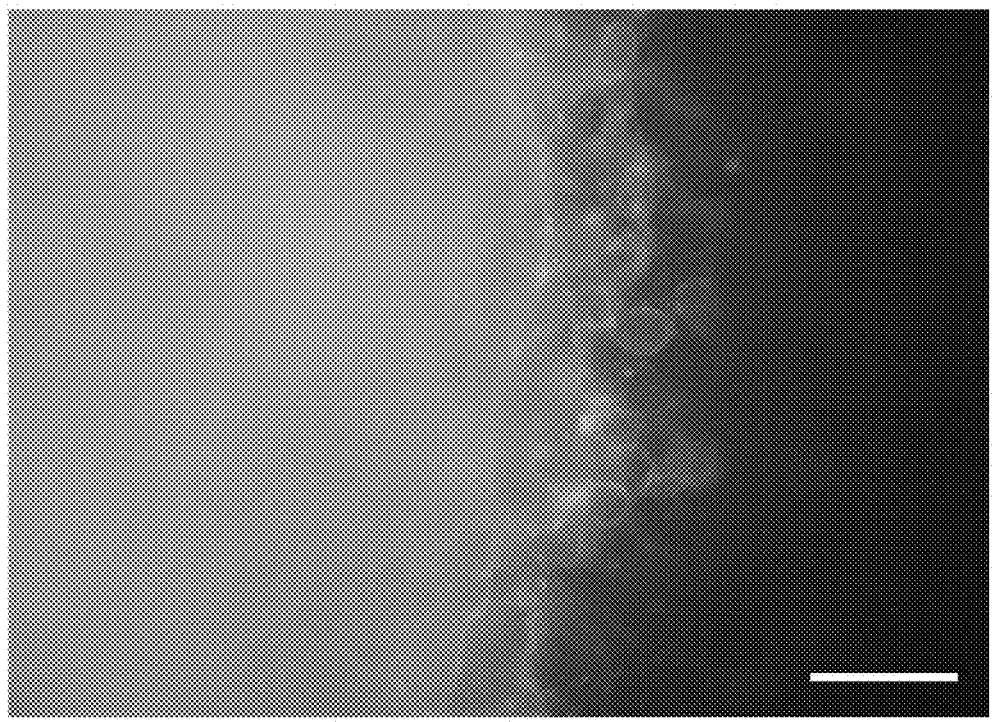

FIG. 12 shows indirect immunofluorescence membraneous staining for N-CAM of single cells at the periphery of a sphere 4 hours after plating on adhesive substrate. The sphere was generated by direct transfer of undifferentiated ES cells into serum free medium and propagation of the resulting spheres for 5 passages. (Scale bar 25 microns).

Figure 13:
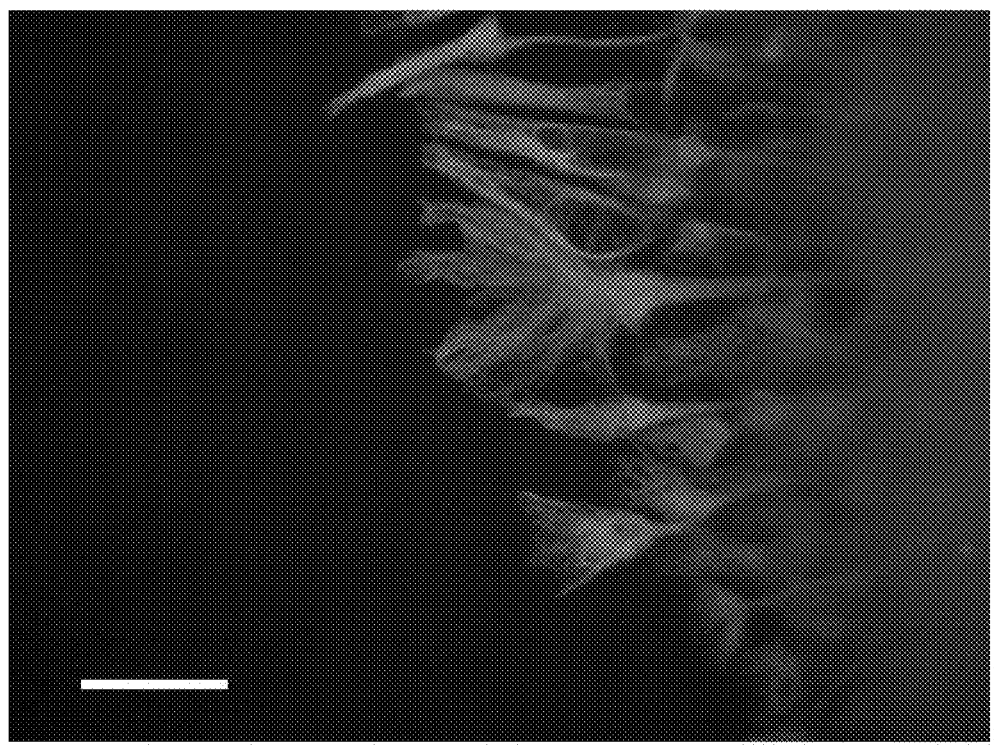

FIG. 13 shows indirect immunofluorescence staining of a spheres 4 hours after plating on adhesive substrate for the intermediate filament nestin. Cells at the base of the sphere were placed in plane of focus to illustrate filamentous staining. The sphere was generated by direct transfer of undifferentiated ES cells into serum free medium and propagation of resulting spheres for 5 passages. (Scale bar 25 microns).

Figure 14:
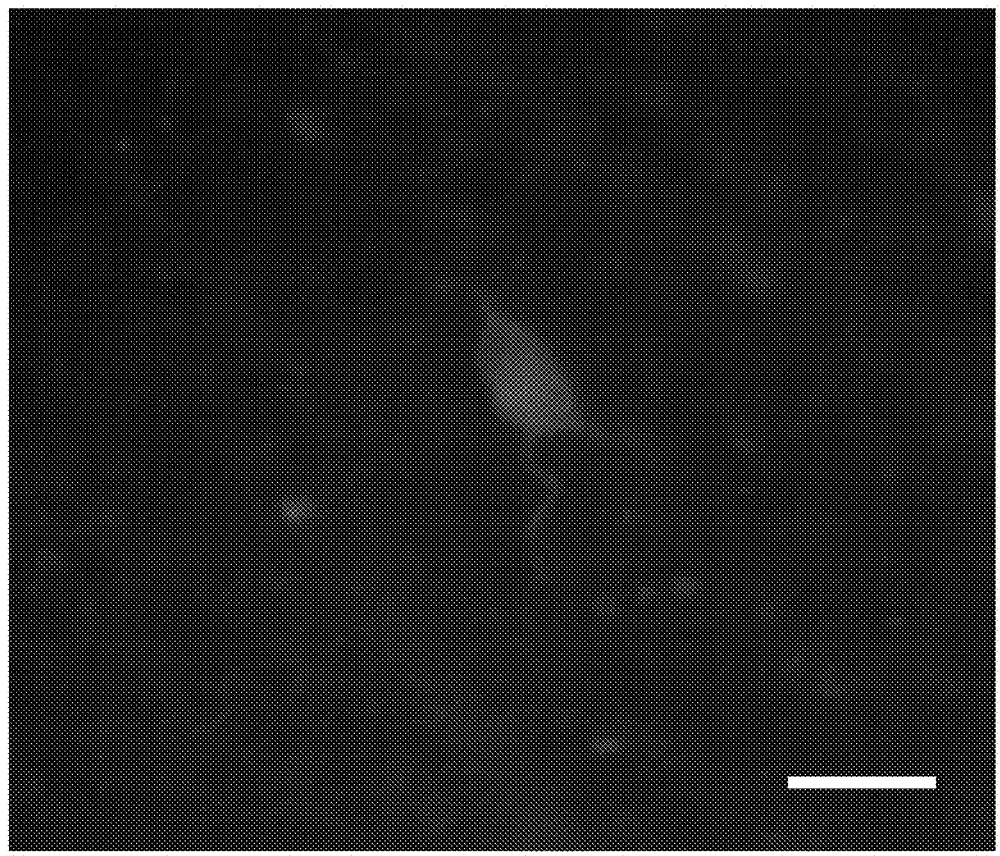

FIG. 14 shows indirect immunofluorescence microscopy of a differentiated cell decorated with antibodies against the oligodendrocyte progenitor marker O4. (Scale bar 12.5 microns).

Figure 15:
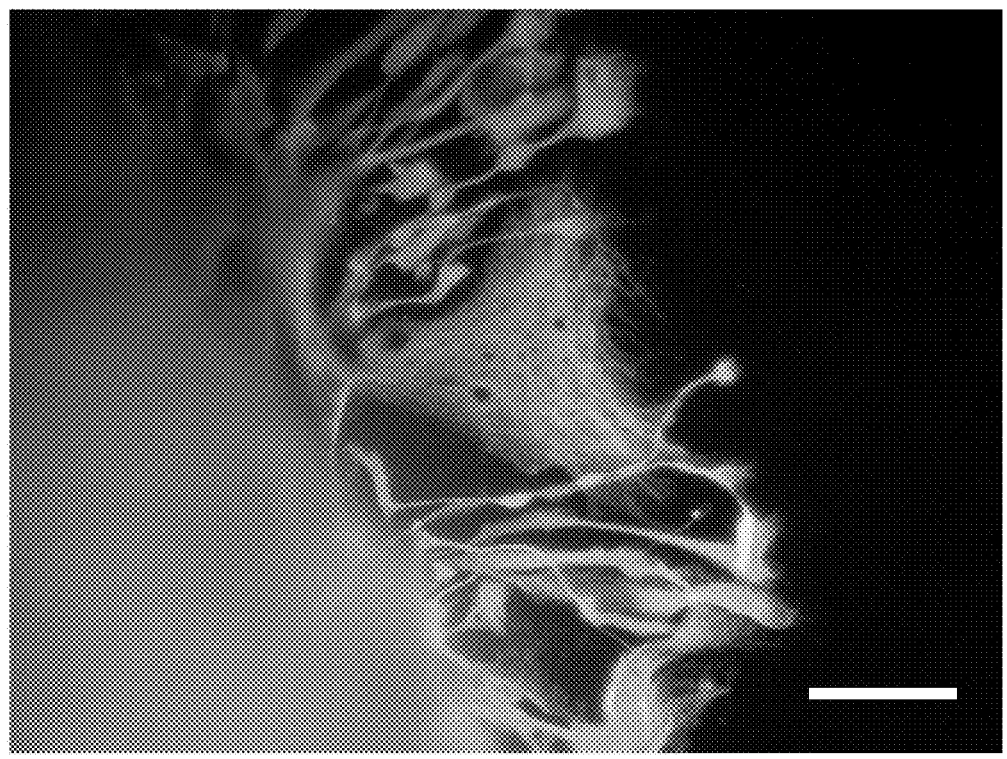

FIG. 15 shows indirect immunofluorescence staining of a sphere 4 hours after plating on adhesive substrate for the intermediate filament vimentin. Cells at the base of the sphere were placed in plane of focus to illustrate filamentous staining. The sphere was generated by direct transfer of undifferentiated ES cells into serum free medium and propagation of resulting spheres for 7 passages. (Scale bar 25 microns).

Figure 16:
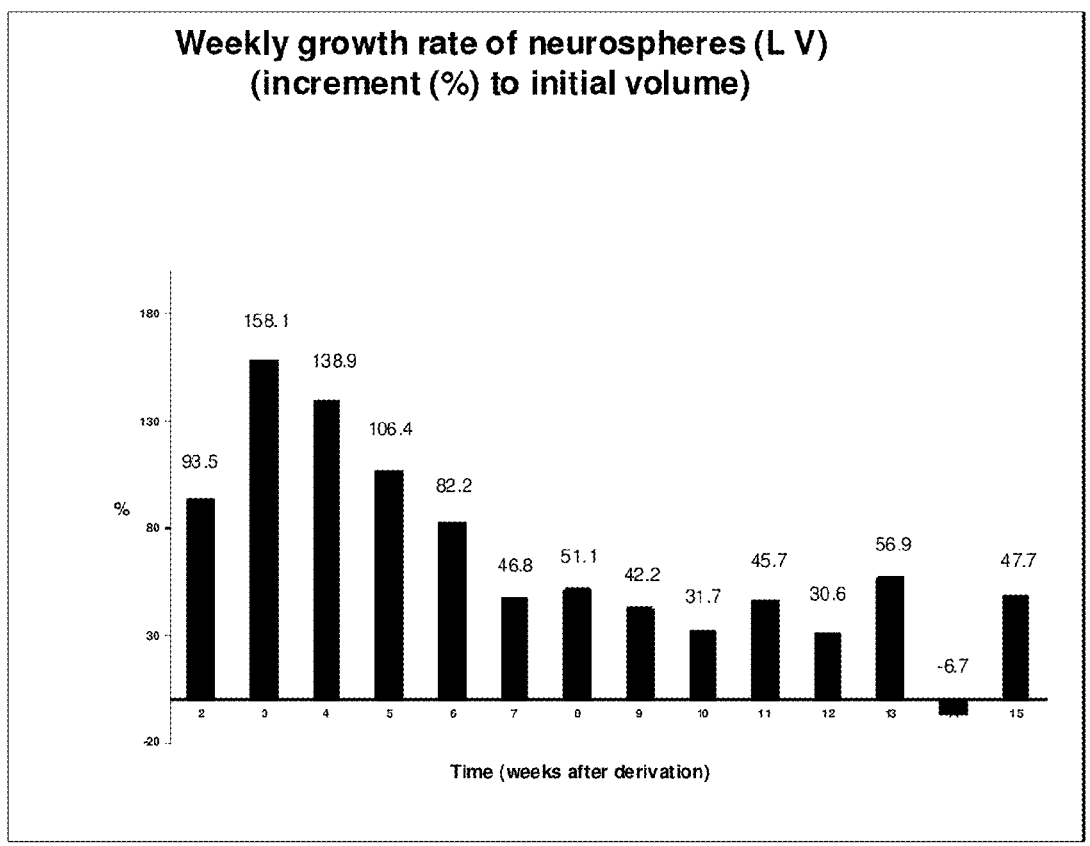

FIG. 16 shows the growth pattern of spheres that were generated directly from undifferentiated ES cells. Each bar represents the mean(±SD) increment in volume per week of 24 spheres at first to sixteen weeks after derivation. A more excessive growth rate is evident during the first 5 weeks.

Figure 17:
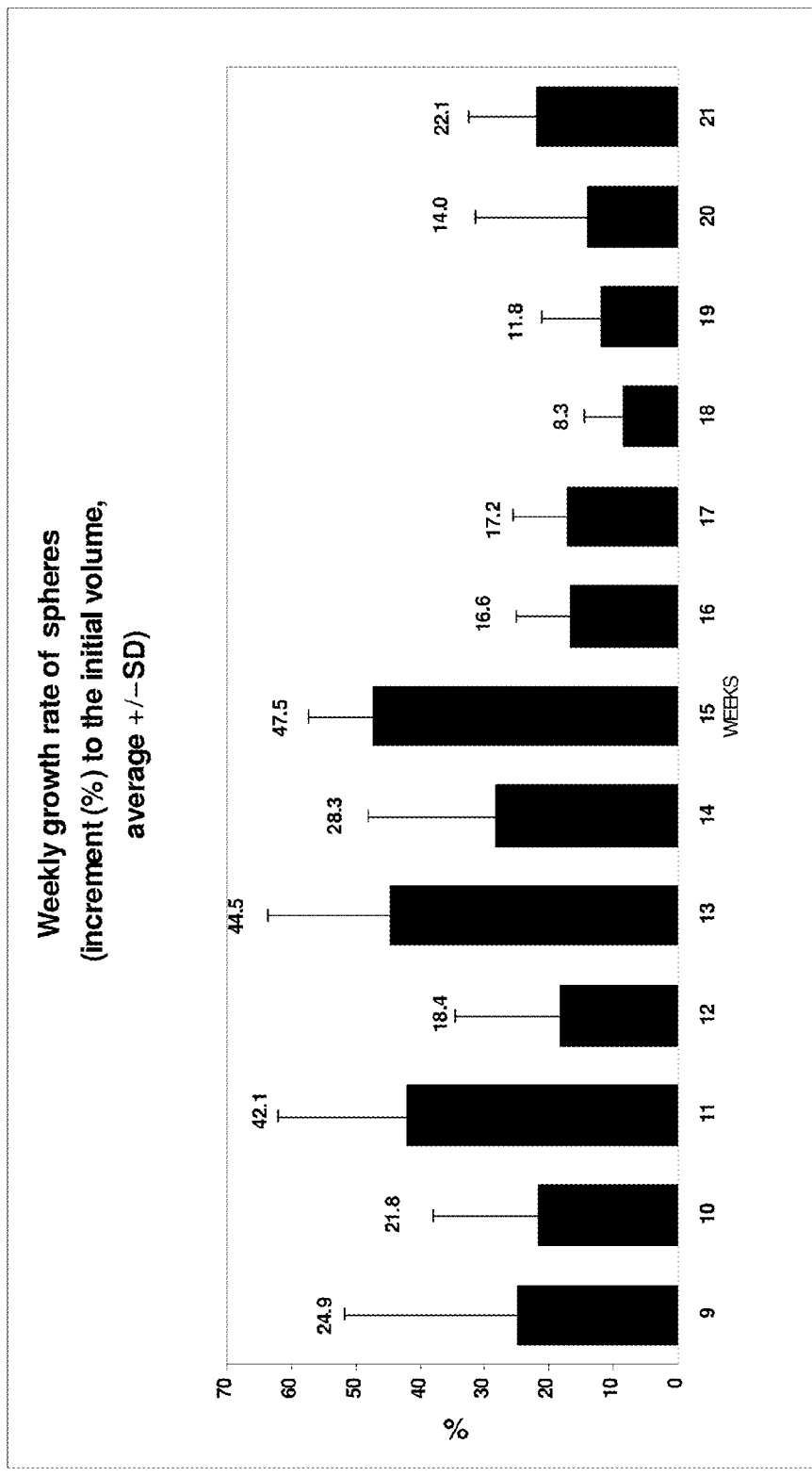

FIG. 17 shows persistent growth in the volume of spheres along time. Each bar represents the mean(±SD) increment in volume per week of 24 spheres at nine to twenty one weeks after derivation. The spheres were generated from differentiating ES colonies.

Figure 18:
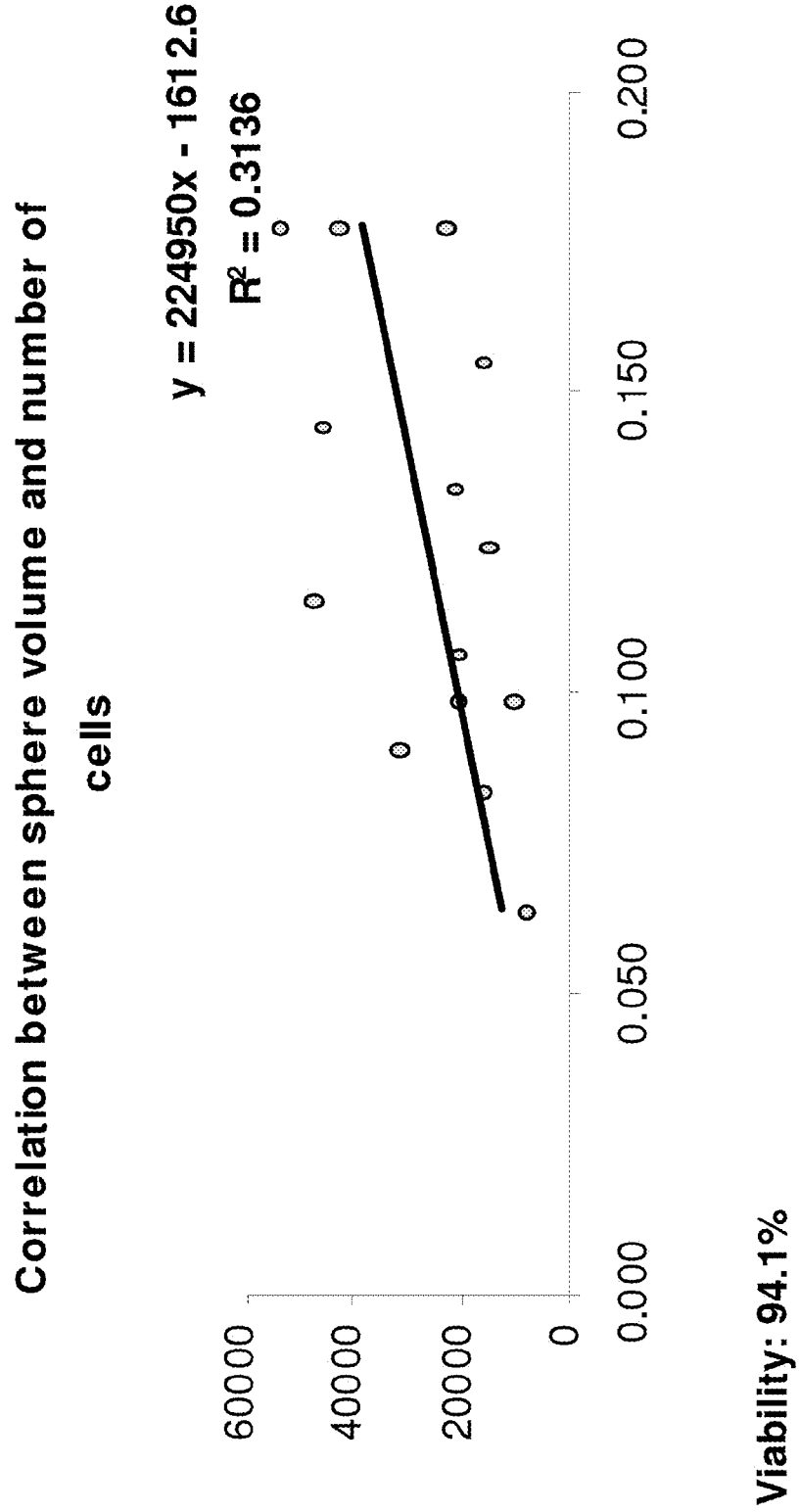

FIG. 18 shows linear correlation between the volume of spheres and the number of progenitor cells within a sphere. Spheres of various diameters, that were generated directly from undifferentiated ES cells and were propagated 5-7 weeks, were dissaggregated into single cell suspension and the number of cells per sphere was counted.

Figure 19:
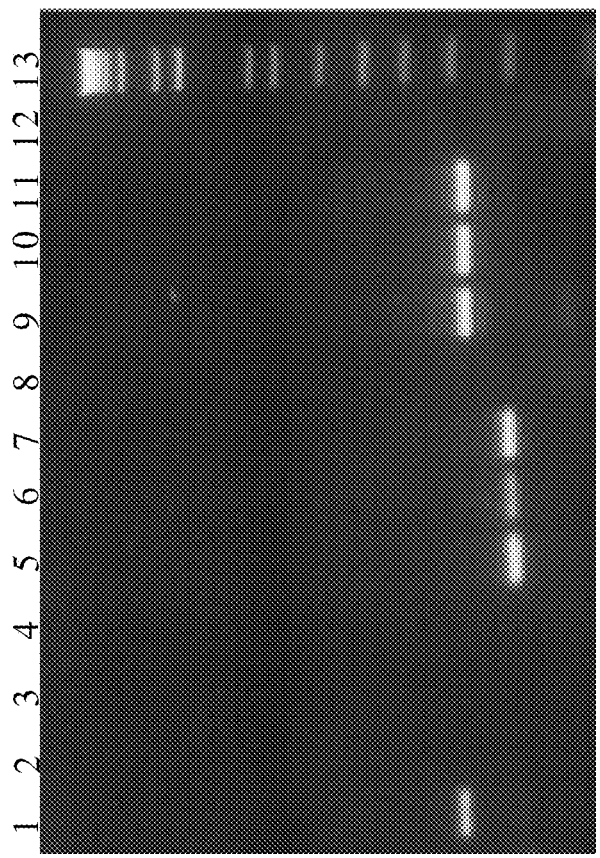

FIG. 19 shows RT-PCR analysis of gene expression in ES cells (a week after passage) and neural spheres derived from differentiating colonies and directly from undifferentiated ES cell. All panels show 2% agarose gels stained with ethidium bromide. Lanes 1, 2 and 3, Oct-4 in ES cell culture, neural spheres derived from differentiating colonies, neural spheres derived from undifferentiated ES cells. Lane 4, stem cell culture, PCR for Oct-4 carried out with omission of reverse transcriptase. Lanes 5, 6, and 7, nestin in ES cell culture, neural spheres derived from differentiating colonies, neural spheres derived from undifferentiated ES cells. Lane 8, stem cell culture, PCR for nestin carried out with omission of reverse transcriptase. Lanes 9, 10 and 11, Pax-6 in ES cell culture, neural spheres derived from differentiating colonies, neural spheres derived from undifferentiated ES cells. Lane 12, stem cell culture, PCR for Pax-6 carried out with omission of reverse transcriptase. Lane 13, 100 bp DNA ladder. Oct-4 band is 320 bp, nestin is 208 bp and Pax-6 is 274 bp.

Figure 20:
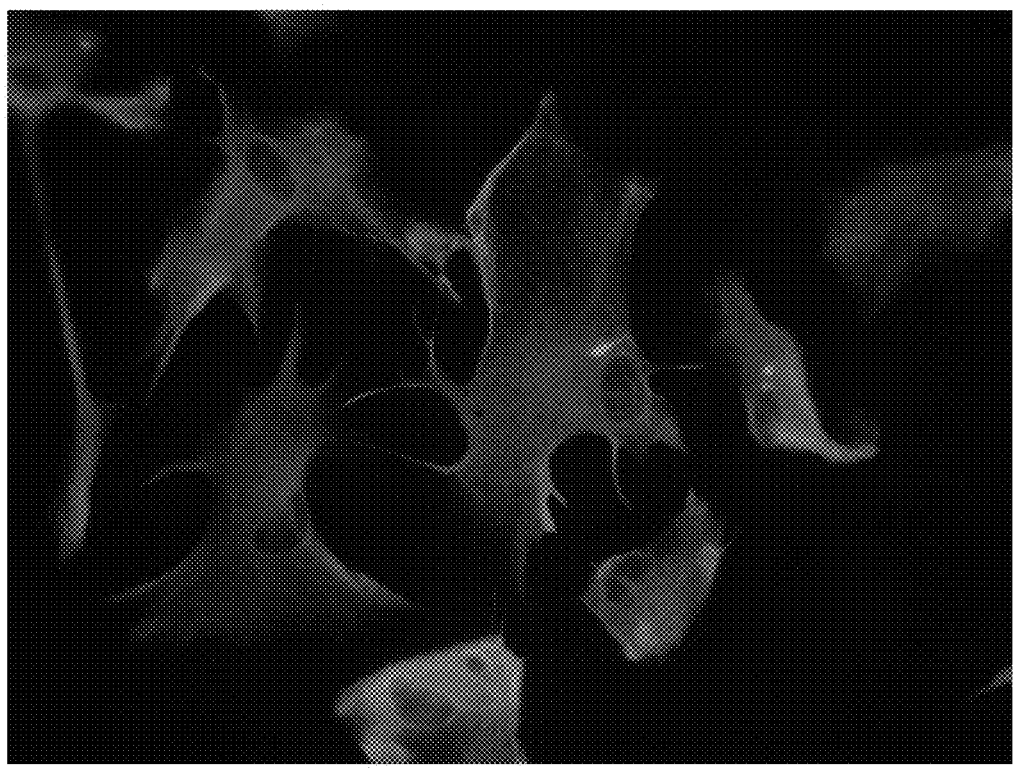

FIG. 20 shows indirect immunofluorescence microscopy of differentiated astrocyte cells decorated with antibody against GFAP. (Scale bar 25 microns).

Figure 21:
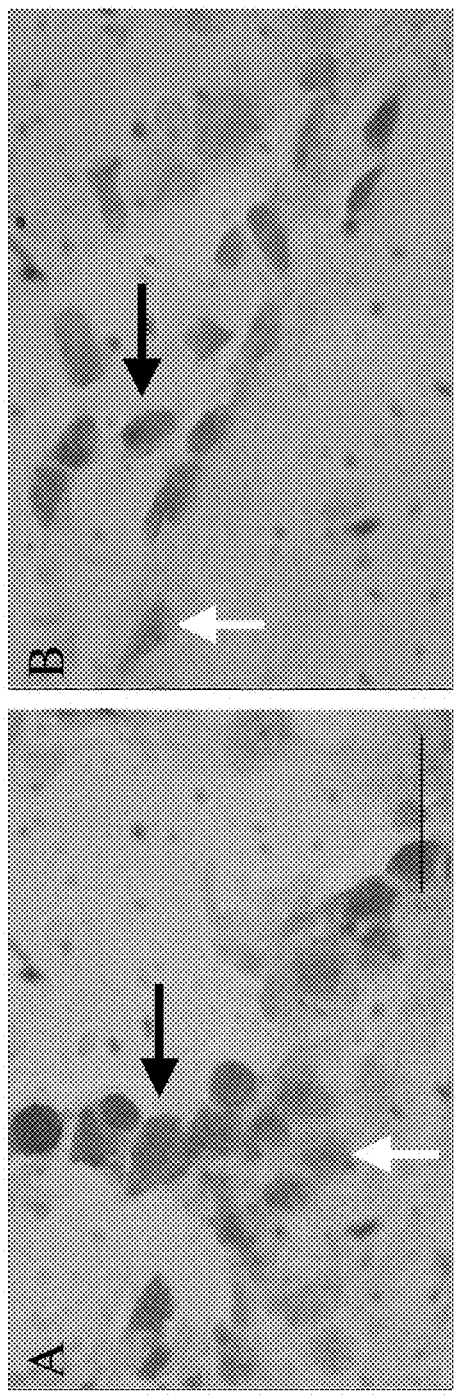

FIG. 21 shows indirect immunofluorescence microscopy of brain sections of two mice (A and B) 4 weeks after transplantation of human neural precursors prelabeled with BrDU. Cells with a nucleus decorated with anti BrDU (brown stain, black arrow) are evident near the ventricular surface (white arrow indicate mouse unstained nuclei, bar=20 microns).

Figure 22:
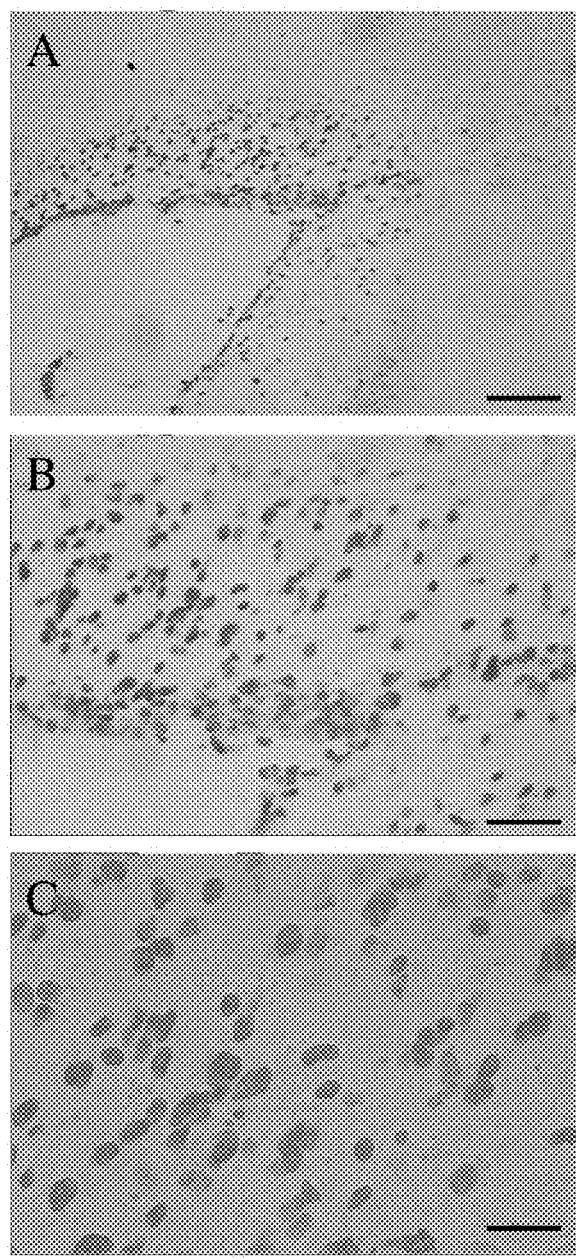

FIG. 22 shows indirect immunofluorescence microscopy of brain sections of a mice 4 weeks after transplantation of human neural precursors prelabeled with BrDU. Wide spread distribution of transplanted human cells decorated by anti BrDU antibodies is evident in the periventricular areas. The periventricular area in A is demonstrated at a higher magnification in B and C. (Bars=150, 60 and 30 microns in A, B and C).

Figure 23:
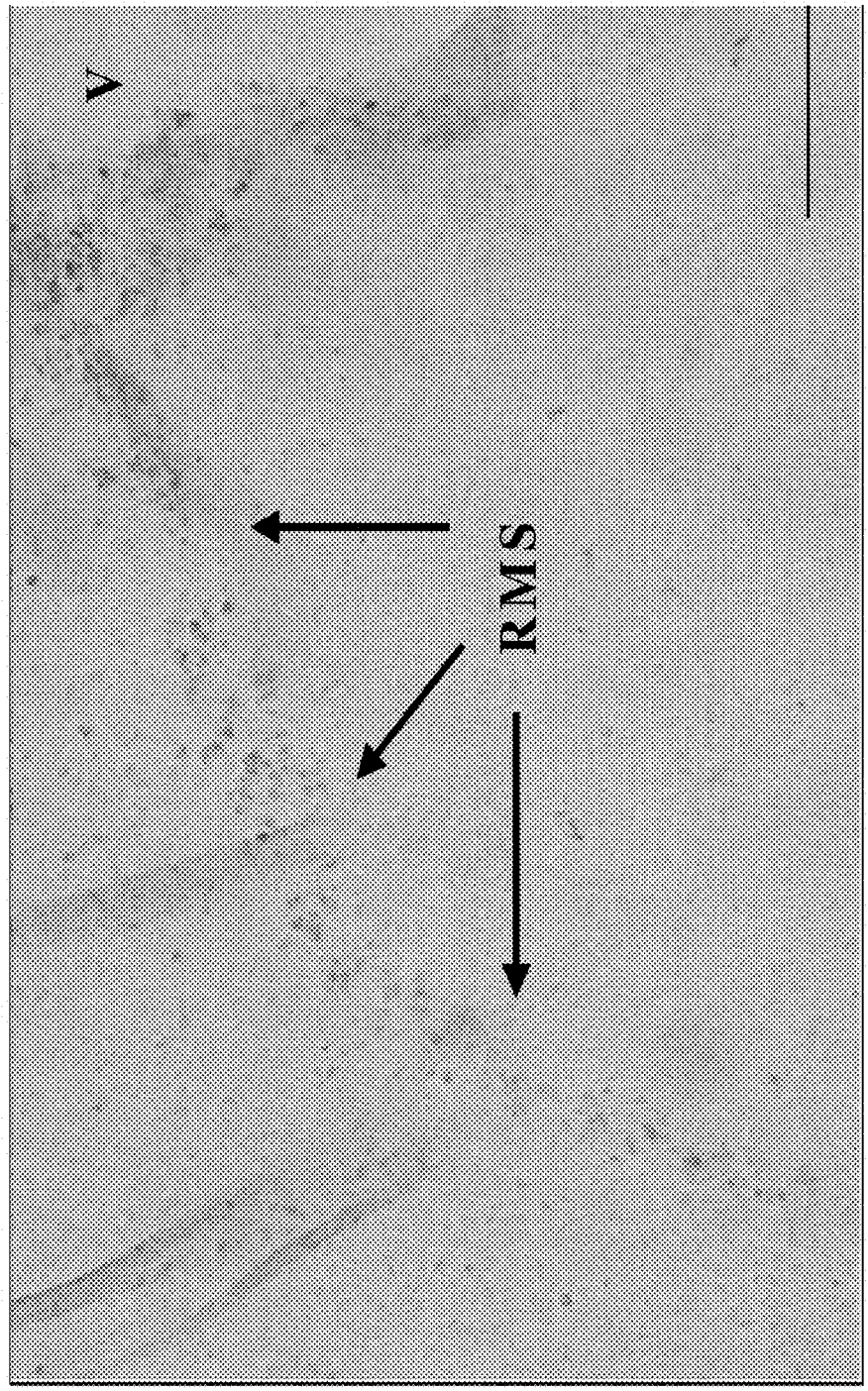

FIG. 23 shows indirect immunocytochemical microscopy of brain sections of a mice 4 weeks after transplantation of human neural precursors prelabeled with BrDU. The transplanted human cells are migrating along the rostral migratory stream (bar=150 microns).

Figure 24:
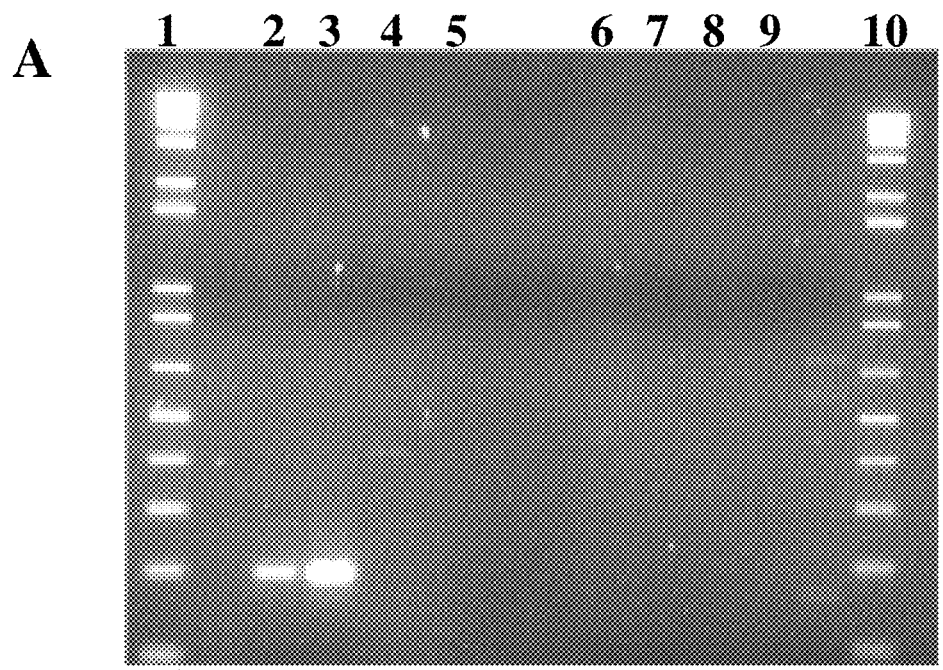
Figure 24:
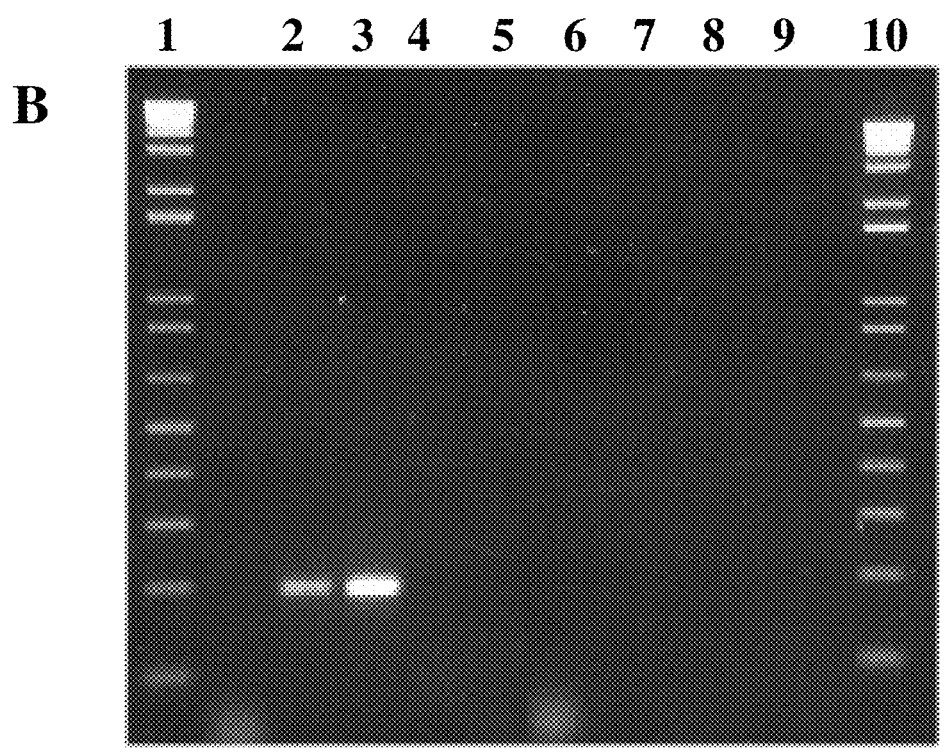

FIG. 24 shows RT-PCR analysis of gene expression in neural spheres derived from differentiating (A) and undifferentiated (B) ES cells. All panels show 2% agarose gels stained with ethidium bromide. Lanes 1 and 10, 100 bpDNA ladder; Lane 2, CD-34; Lane 3, Flk-1; lane4, HNF-3; lane 5, alfafetoprotein. Lanes 6-9 PCR reaction on the same samples as lanes 2-5 carried out with the omission of reverse transcriptase. CD-34 band is 200 bp, Flk-1 is 199, HNF-3 is 390, AFP is 340 bp.

Figure 25:
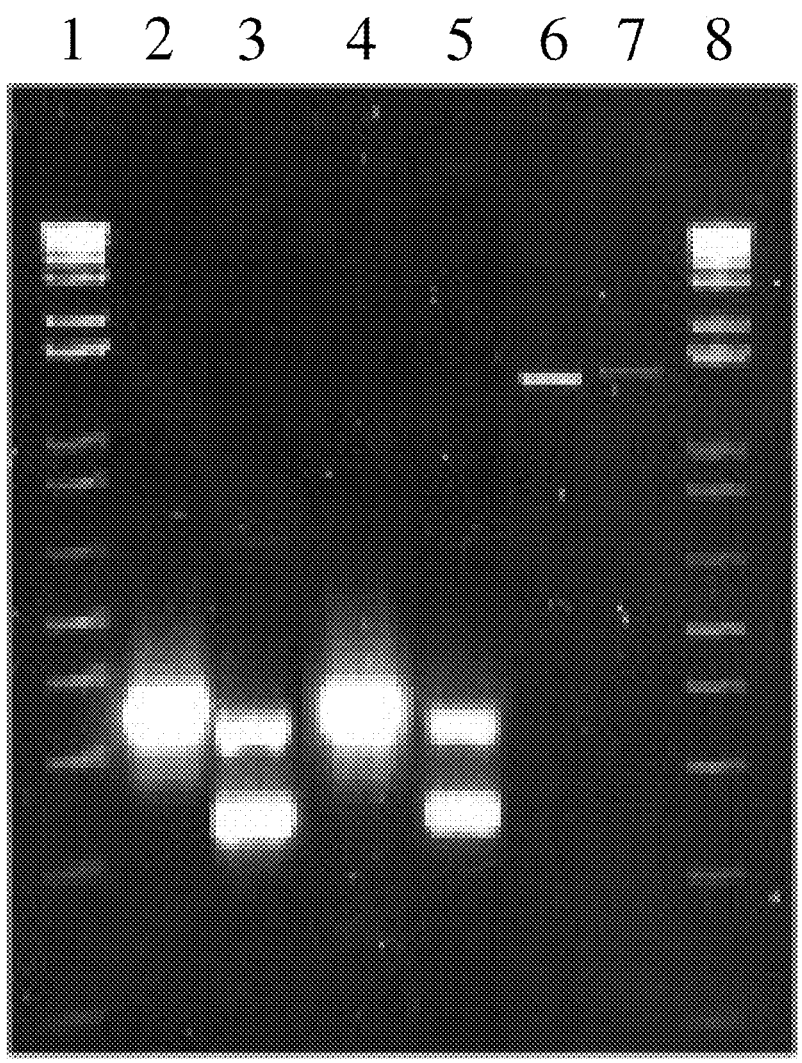

FIG. 25 shows by RT-PCR analysis the expression of GFAP and the plp gene in differentiated cells from neural spheres derived from differentiating ES cell colonies. The expression of GFAP indicates differentiation into astrocytes while
the presence of both dm-20 and plp transcripts indicate that differentiation into oligodendrocyte cells has occurred. Lanes 2, 4, 6 and lanes 3, 5, 7 are from two separate RNA samples from differentiated spheres that were independently derived from ES cells. Lane 1 and 8, 100 bp DNA ladder; Lanes 2 and 4, GFAP; lanes 3 and 5, plp and dm-20; lanes 6 and 7, PCR reaction on the same samples as lanes 3 and 5 carried out with the omission of reverse transcriptase. GFAP band is 383, plp band is 354 bp and dm-20 is 249 bp.

Figure 26:
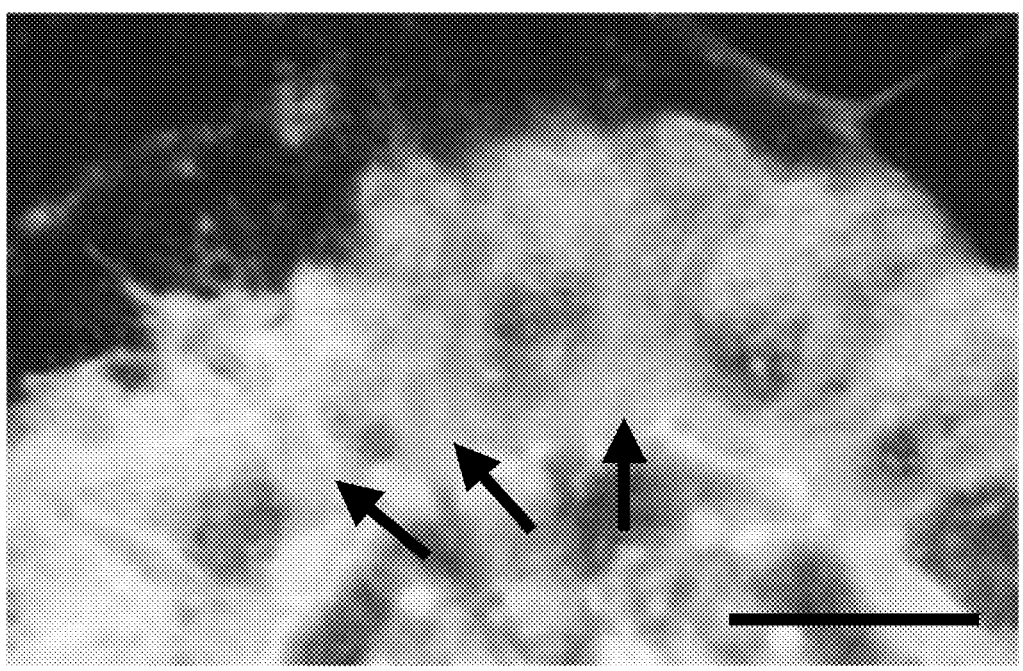

FIG. 26 shows a dark field stereomicroscopic photograph of areas (arrows) destined to give rise to neural precursors in a differentiating ES cell colony 3 weeks after passage (bar=1.6 mm).

Figure 27:
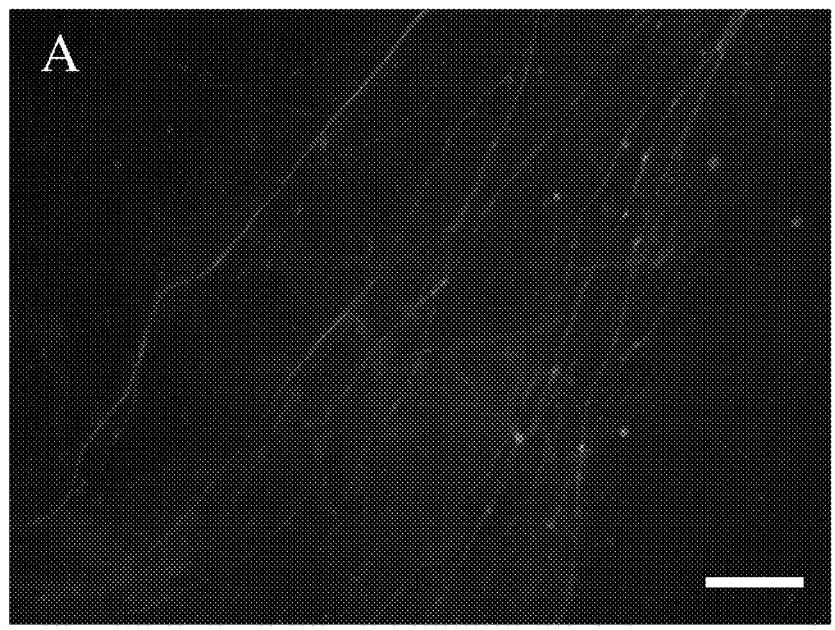
Figure 27:
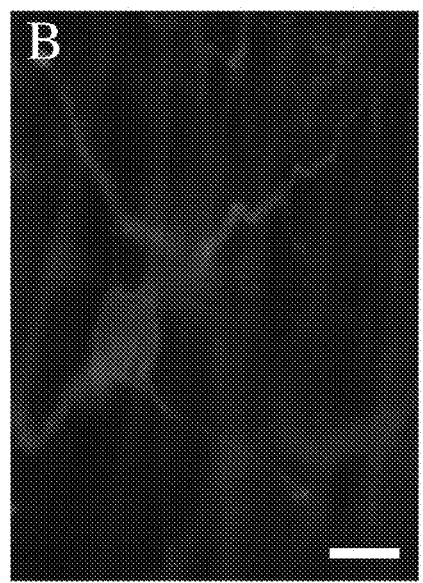
Figure 27:
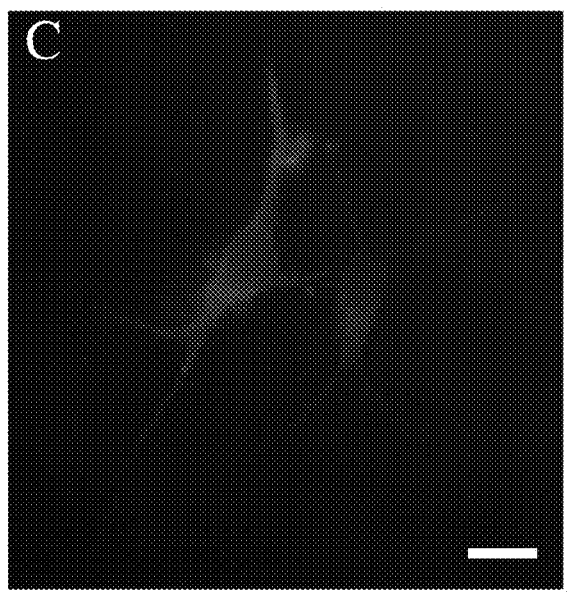

FIG. 27 shows indirect immunochemical analysis of marker expression in cultures of neurons derived from progenitor cells that were derived directly from undifferentiated ES cells: A, indirect immunofluorescence microscopy of neurits decorated with antibody against 160 kDa neurofilament protein. B and C, indirect immunofluorescence staining of differentiated cells for MAP2a+b and β-tubulin III. Scale bars: A 100 microns, B and C 10 microns.

Figure 28:
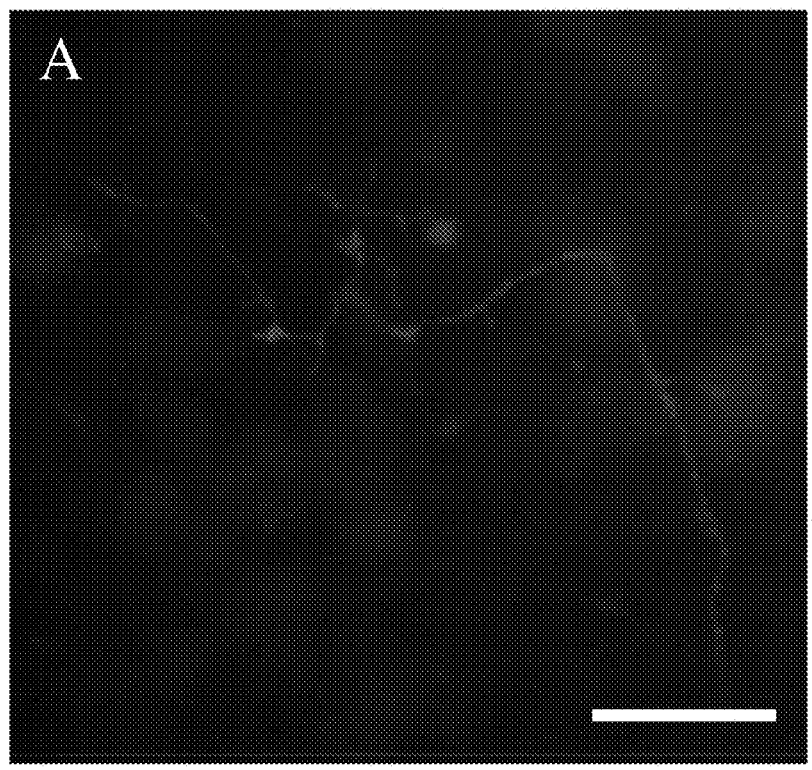
Figure 28:
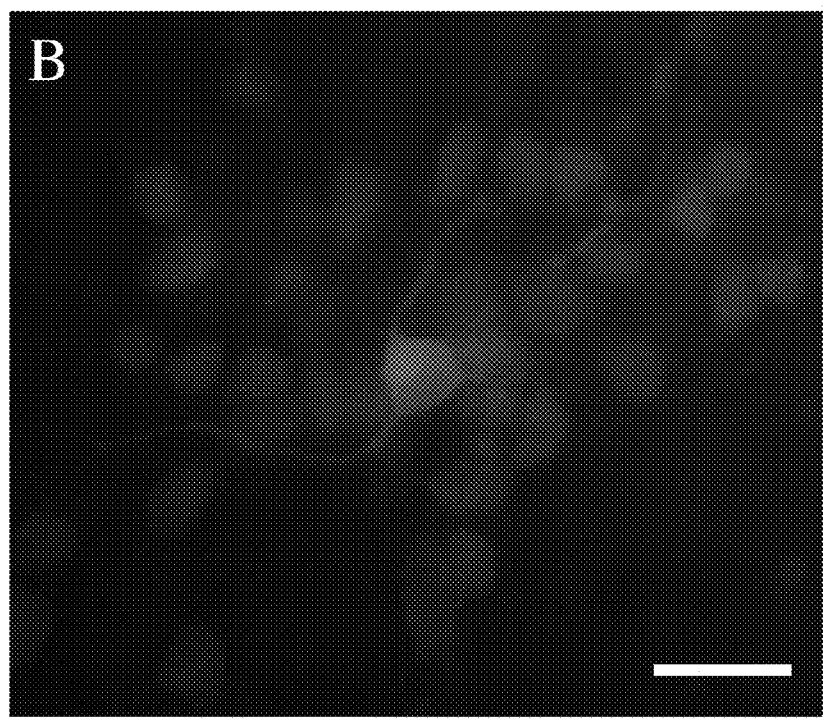

FIG. 28 shows indirect immunochemical analysis of the expression of tyrosine hydroxylase. Neurits (A) and a differentiated cell (B) are decorated with antibodies against tyrosine hydroxylase. Scale bars: 30 microns.

FIG. 29 shows in vivo differentiation into astrocyte cells of transplanted human neural progenitors prelabeled with BrDU. Donor cells are identified by indirect immunochemical detection of BrDU (dark nuclei, arrows). Duel staining demonstrates donor cells decorated by anti GFAP (orange). Transplanted cells are migrating into the brain parenchyma (white arrow) and are also found in the periventricular zone (dark arrow) (A), A higher magnification of cells that have differentiated into astrocytes and migrated into the host brain (B).

Figure 30:
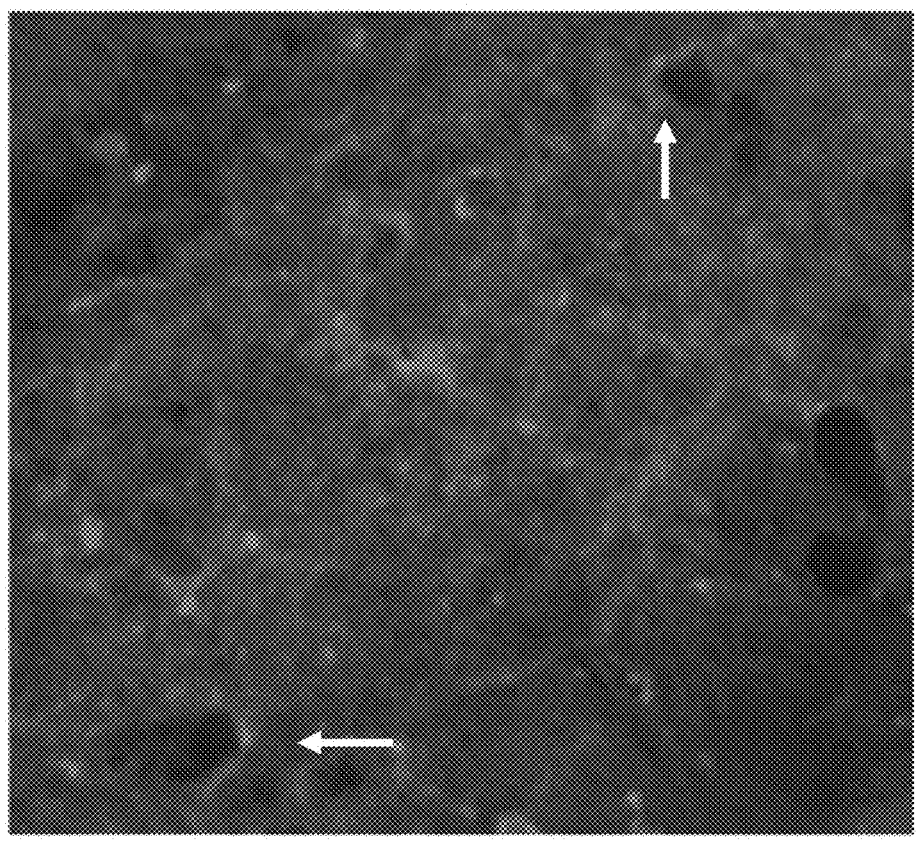

FIG. 30 shows in vivo differentiation into oligodendrocyte cells of transplanted human neural progenitors prelabeled with BrDU. Donor cells are identified by indirect immunochemical detection of BrDU (dark nuclei, arrows). Duel staining demonstrates donor cells decorated by anti CNPase (orange).

Figure 31:
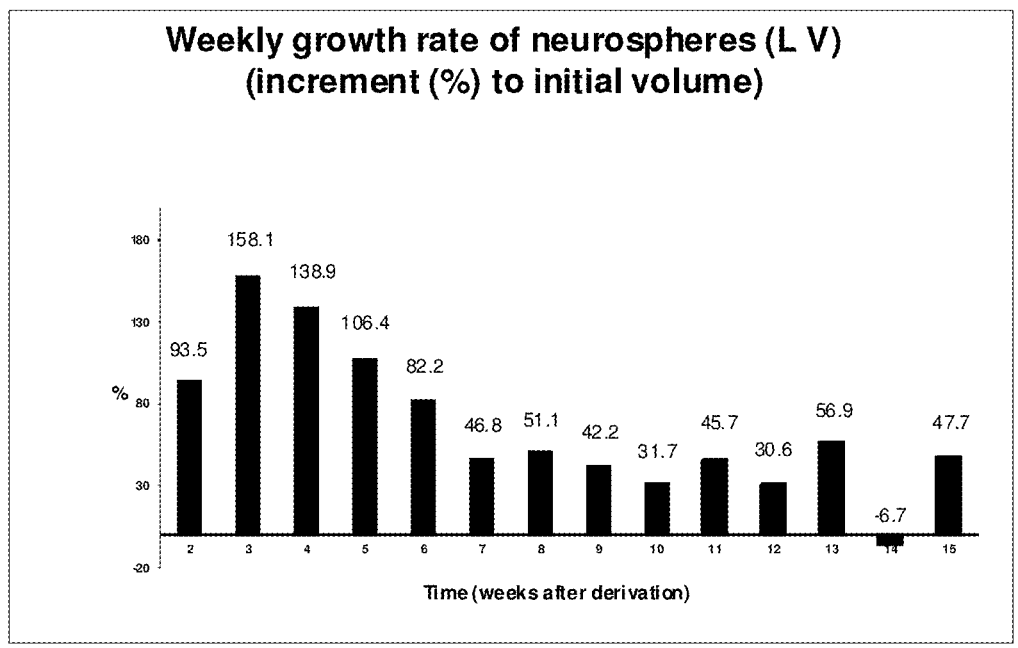

FIG. 31 shows cumulative growth curve for human neural progenitors derived from differentiating colonies. (A) Continuous growth is evident during an 18-22 week period. The increment in the volume of the spheres was continuously monitored as an indirect measure of the increase in cell numbers. A linear positive correlation between the volume of the spheres and the number of cells within the spheres (B, insert) was maintained along cultivation. It supported the validity of monitoring the increment of sphere volume as an indirect indicator of cell proliferation.

Figure 32:
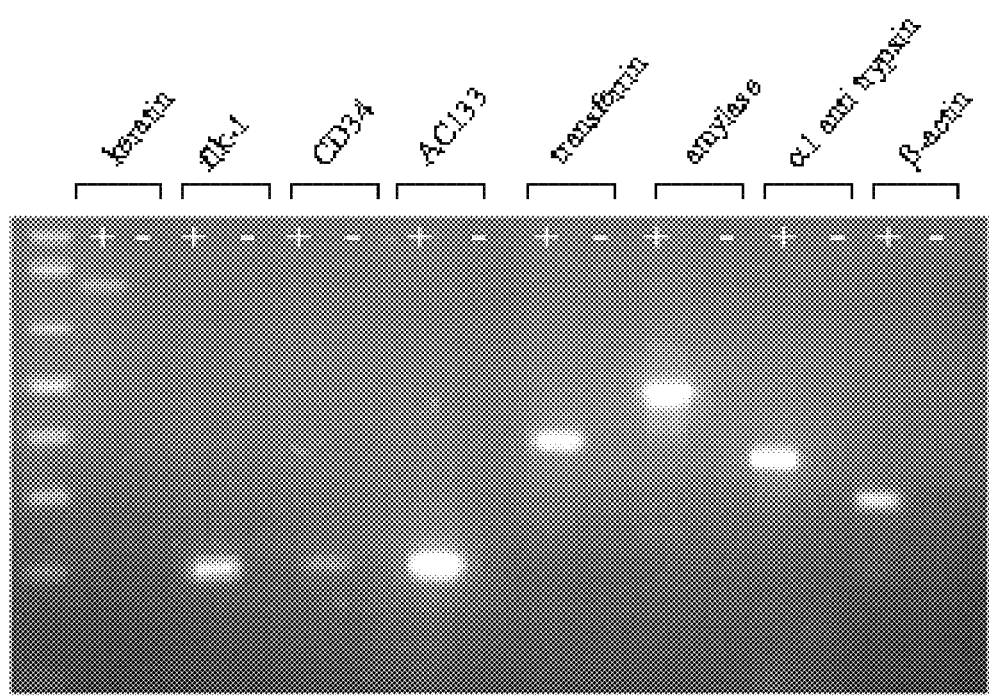

FIG. 32 shows RT-PCR analysis of the expression of non-neural markers in human ES derived spheres. All panels show 2% agarose gels stained with ethidium bromide. The symbols + and − indicate whether the PCR reaction was performed with or without the addition of reverse transcriptase. A 1 Kb plus DNA ladder was used in all panels. β-actin band is 291 bp, keratin is 780 bp, Flk-1 is 199 bp, CD34 is 200 bp, AC-133 is 200 bp, transferin is 367 bp, amylase is 490 bp and α1 anti trypsin is 360 bp.

Figure 33:
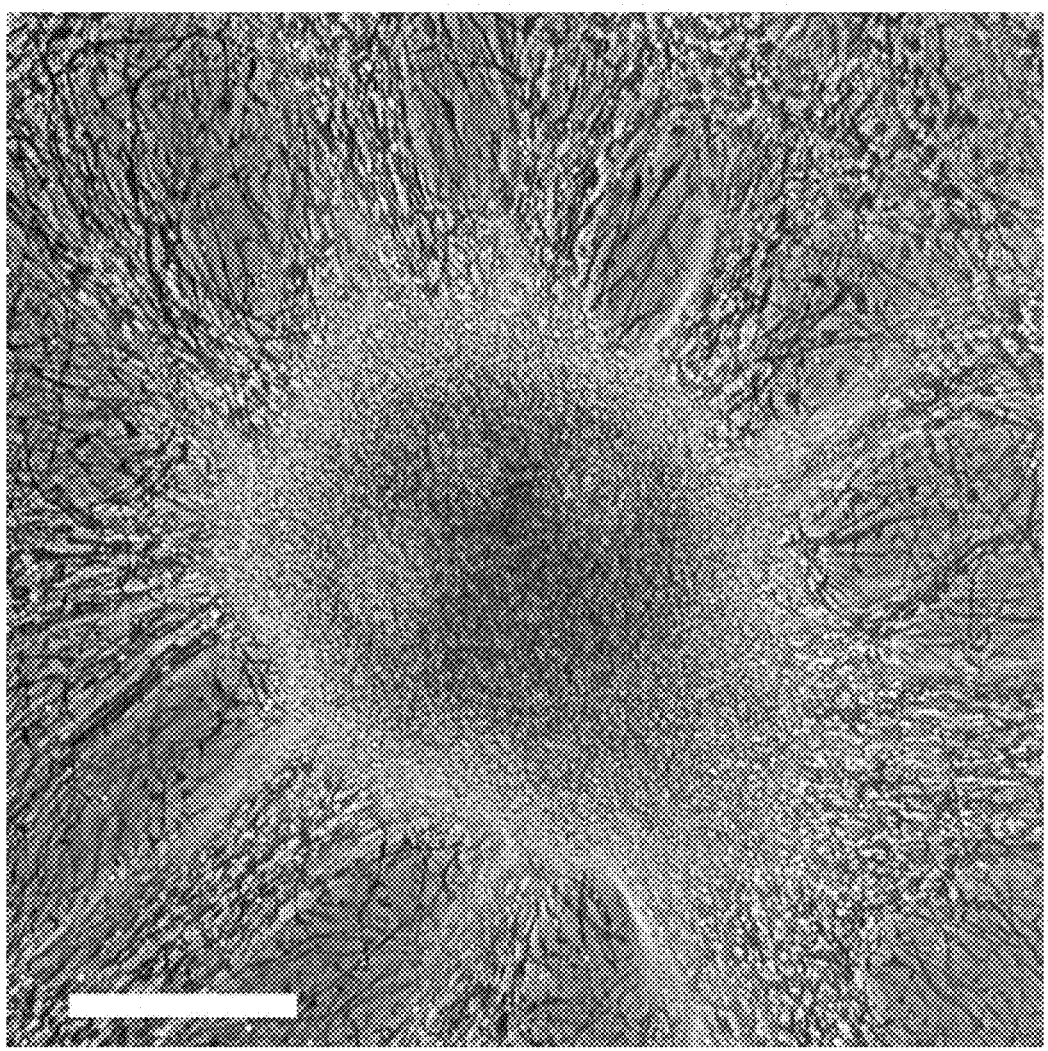

FIG. 33 shows a phase contrast micrograph of differentiated cells growing out from a sphere 2 weeks after plating onto an adhesive surface and culture in the absence of growth factors. Scale bar is 200 μm.

Figure 34:
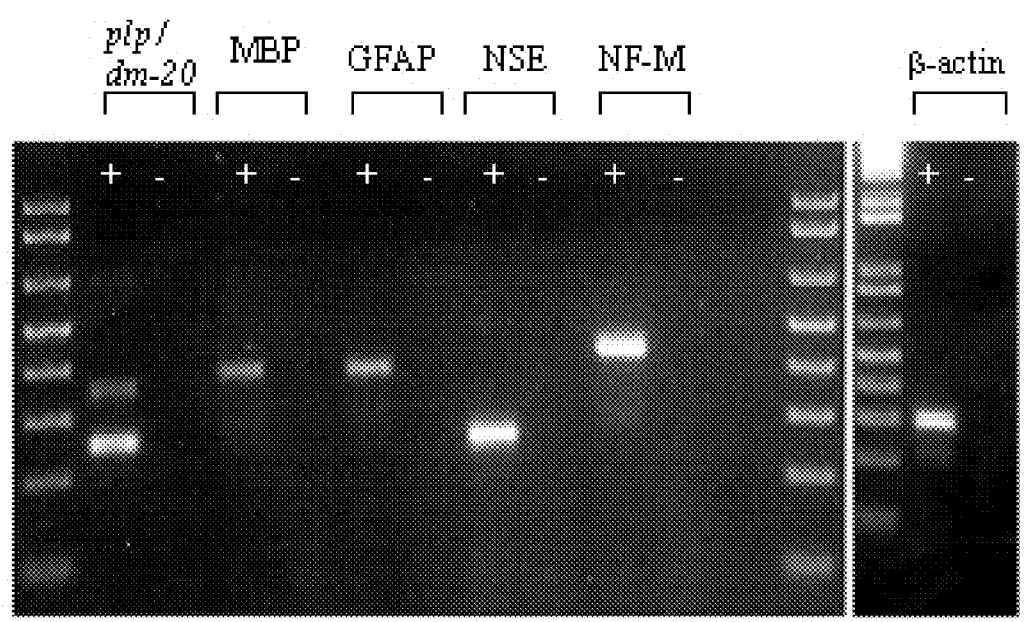

FIG. 34 shows RT-PCR analysis of the expression of neuronal and glial markers in differentiated cells originating from human ES derived neural spheres. All panels show 2% agarose gels stained with ethidium bromide. The symbols + and − indicate whether the PCR reaction was performed with or without the addition of reverse transcriptase. A 1 Kb plus DNA ladder was used in all panels. Plp and dm-20 bands are 354 bp and 249 bp respectively, MBP is 379 bp, GFAP is 383 bp, NSE is 254 bp and NF-M is 430 bp.

Figure 35:
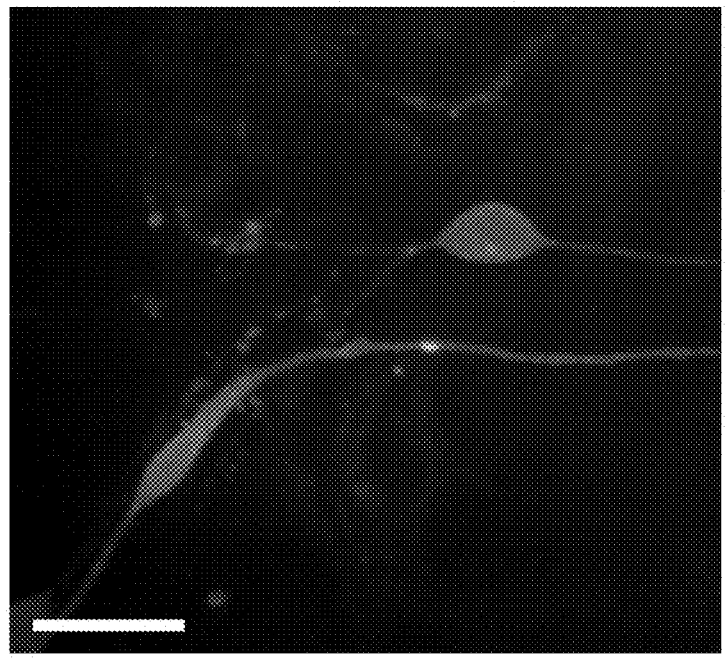
Figure 35:
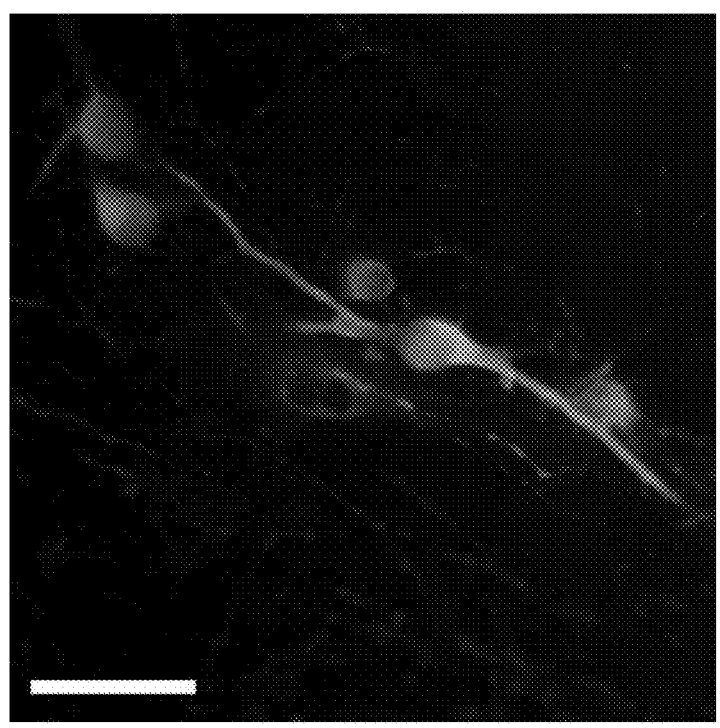

FIG. 35 shows indirect immunochemical analysis of the expression of serotonin (A) and GABA (B). Scale bars are 20 μm.

Figure 36:
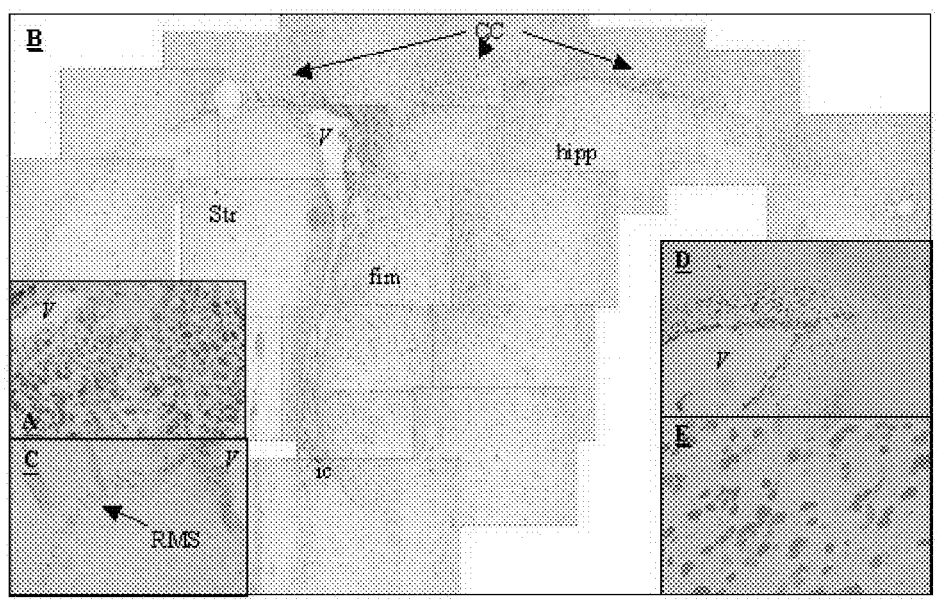

FIG. 36 shows dissemination of transplanted BrdU+ human ES-derived neural progenitor cells in the mouse host brain.
(A) At 2 days after transplantation most cells were found lining the ventricular wall. (B) After 4-6 weeks most cells had left the ventricles (V) and populated the corpus callosum (CC), fimbria (fim), internal capsule (i.c.). BrdU+ cells were not found in the striatum (str) or CA region of the hippocampus (hipp). (C) Chains of BrdU+ cells were found in the rostral migratory stream (RMS). (D) BrdU+ cells in the periventricular white matter. (E) Higher magnification of D, to show nuclear specific localization of BrdU.

Figure 37:
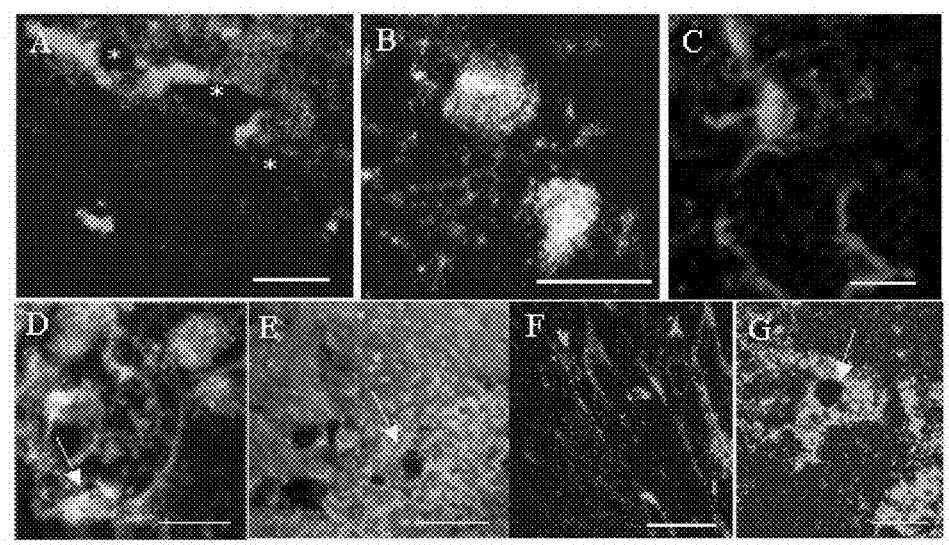

FIG. 37 shows identification of the transplanted cells in the brain by human and neural-lineage specific markers. (A) A typical chain of transplanted cells in the corpus callosum, stained with human specific anti-mitochondrial antibody. The mitochondrial staining (green fluorescence) on Nomarsky background (blue, cell nuclei indicated by asterisk) shows a typical perinuclear localization. (B) Double staining for BrdU (green fluorescence) and human specific anti ribonuclear protein (red fluorescence) shows nuclear co-localization, indicating that BrdU+ cells were indeed of human origin. (C) A GFAP+ astrocyte (red) from the periventricular region, co-labeled with BrdU (green), indicating its origin from the graft. (D) An NG2+ oligodendrocyte progenitor (red) in the periventricular region, co-labeled with BrdU (green). (E) A CNPase+ oligodendrocyte (red) in the corpus callosum, co-labeled with BrdU (immunohistochemistry, shown as dark nucleus in Nomarsky). (F) Neuronal processes in the fimbria, stained with a human specific anti-70 kDa neurofilament. (G) A βIII-tubulin+ neuron (green fluorescence) in the olfactory bulb, co-labeled with BrdU (as dark nucleus (arrow) in Nomarsky). Bars=10 μm.

DESCRIPTION OF THE INVENTION

In one aspect of the present invention there is provided an enriched preparation of human undifferentiated embryonic stem cells capable of proliferation in vitro and differentiation to neural progenitor cells, neuron cells and/or glial cells.

Throughout the description and claims of this specification, the word "comprise" and variations of the word, such as "comprising" and "comprises", is not intended to exclude other additives, components, integers or steps.

Established pluripotent ES cell lines from human blastocysts are shown in, PCT/AU99/00990 by the applicants. In contrast to data that has published previously, the human ES cell lines that have been derived by the applicants in the present application have been shown to differentiate in vitro into somatic lineages and give rise to neurons and muscle cells. Moreover, Applicants have demonstrated the derivation of neural progenitor cells from human ES cells in vitro. These ES derived human neural progenitors may give rise to mature neurons in vitro. The contents of PCT/AU99/00990 are hereby incorporated.

Proliferation in vitro may include cultivation of the cells for prolonged periods. The cells are substantially maintained in an undifferentiated state. Preferably the cells are maintained under conditions which do not induce cell death or extraembryonic differentiation.

Preferably, they are capable of maintaining an undifferentiated state when cultured on a fibroblast feeder layer preferably under non-differentiating conditions. Preferably the fibroblast feeder layer does not induce extraembryonic differentiation.

More preferably the cells have the potential to differentiate in vitro when subjected to differentiating conditions. Most preferably the cells have the capacity to differentiate in vitro into a wide array of somatic lineages.

The promotion of stem cells capable of being maintained in an undifferentiated state in vitro on one hand, and which are capable of differentiation in vitro into extraembryonic and somatic lineages on the other hand, allows for the study of the cellular and molecular biology of early human development, functional genomics, generation of differentiated cells from the stem cells for use in transplantation or drug screening and drug discovery in vitro.

Once the cells are maintained in the undifferentiated state, they may be differentiated to mature functional cells. The embryonic stem cells are derived from the embryo and are pluripotent and have the capability of developing into any organ or tissue type. Preferably the tissue type is selected from the group including endocrine cells, blood cells, neural cells or muscle cells. Most preferably they are neural cells.

In another aspect of the present invention there is provided an undifferentiated human embryonic stem cell wherein the cell is immunoreactive with markers for human pluripotent stem cells including SSEA-4, GCTM-2 antigen, and TRA 1-60 and wherein said cell can differentiate, under differentiating conditions to neural cells. Preferably, the cells express specific transcription factors such as Oct-4 as demonstrated by RT-PCR, or methods of analysis of differential gene expression, microarray analysis or related techniques. More preferably the cells maintain a diploid karyotype during prolonged cultivation in vitro. Preferably, the stem cell will constitute an enriched preparation of an undifferentiated stem cell line. More preferably, the stem cell line is a permanent cell line, distinguished by the characteristics identified above. They preferably have normal karyotype along with the characteristics identified above. This combination of defining properties will identify the cell lines of the invention regardless of the method used for their isolation.

Methods of identifying these characteristics may be by any method known to the skilled addressee. Methods such as (but not limited to) indirect immunoflourescence or immunocytochemical staining may be carried out on colonies of ES cells which are fixed by conventional fixation protocols then stained using antibodies against stem cell specific antibodies and visualised using secondary antibodies conjugated to fluorescent dyes or enzymes which can produce insoluble colored products. Alternatively, RNA may be isolated from the stem cells and RT-PCR or Northern blot analysis carried out to determine expression of stem cell specific genes such as Oct-4.

In a preferred embodiment the undifferentiated cells form tumours when injected in the testis of immunodeprived SCID mice. These tumours include differentiated cells representative of all three germ layers. The germ layers are preferably endoderm, mesoderm and ectoderm. Preferably, once the tumours are established, they may be disassociated and specific differentiated cell types may be identified or selected by any methods available to the skilled addressee. For instance, lineage specific markers may be used through the use of fluorescent activated cell sorting (FACS) or other sorting method or by direct micro dissection of tissues of interest. These differentiated cells may be used in any manner. They may be cultivated in vitro to produce large numbers of differentiated cells that could be used for transplantation or for use in drug screening for example.

In another aspect there is provided a differentiated committed progenitor cell line capable of differentiation and propagation into mature neurons and/or glial cells. The undifferentiated cells may differentiate in vitro to form neural progenitor cells, neuron cells and/or glial cells.

In another aspect, there is provided a neural progenitor cell, neuron cell and/or glial cell differentiated in vitro from an undifferentiated embryonic stem cell. There is also provided a committed neural progenitor cell capable of giving rise to mature neuron cells. The mature neuron cell may be characterized by an ability to express 160 kDa neuro-filament protein, MAP2ab, glutamate, synaptophysin, glutamic acid decarboxylase (GAD), tyrosine hydroxylase, GABA and serotonin.

In another aspect, there is provided a neural progenitor cell capable of differentiating into glial cells, including astrocytes and oligodendrocytes. The glial cells include microglial cells and radial glial cells.

In another aspect, there is provided a neural progenitor cell capable of transdifferentiation into other cell lineages, to generate stem cells and differentiated cells of non-neuronal phenotype, such as hemangioblast hematopoietic stem cells or endothelial stem cells, embryonic endoderm cells and ectoderm cells.

These cells may be obtained by somatic differentiation of human ES cells, identified by neural markers. These cells may be isolated in pure form from differentiating ES cells, in vitro, and propagated in vitro. They may be induced to under go differentiation to mature neurons and/or glial cells.

The cells may undergo differentiation in vitro to yield neural progenitor cells, neuron or glial cells as well as extraembryonic cells, such differentiation being characterised by novel gene expression characteristic of specific lineages as demonstrated by immunocytochemical or RNA analysis. Characterisation may be obtained by using expression of genes characteristic of pluripotent cells or particular lineages. Preferably, differential expression of Oct-4 may be used to identify stem cells from differentiated cells. Otherwise, the presence or absence of expression of other genes characteristic of pluripotent stem cells or other lineages may include Genesis, GDF-3 or Cripto. Analysis of these gene expressions may create a gene expression profile to define the molecular phenotype of an ES cell, a committed progenitor cell, or a mature differentiated cell of any type. Such analysis of specific gene expression in defined populations of cells from ES cultures is called cytomics. Methods of analysis of gene expression profiles include RT-PCR, methods of differential gene expression, microarray analysis or related techniques.

Differentiating cultures of the stem cells secrete human chorionic gonadotrophin (hCG) and α-fetoprotein (AFP) into culture medium, as determined by enzyme-linked immunosorbent assay carried out on culture supernatants. Hence this may also serve as a means of identifying the differentiated cells.

The differentiated cells forming neural progenitor cells, neuron cells and/or glial cells may also be characterised by expressed markers characteristic of differentiating cells. The in vitro differentiated cell culture may be identified by detecting molecules such as markers of the neuroectodermal lineage, markers of neural progenitor cells, neuro-filament proteins, monoclonal antibodies such as MAP2ab, glutamate, synaptophysin, glutamic acid decarboxylase, GABA, serotonin, tyrosine hydroxylase, β-tubulin, β-tubulin III, GABA Aα2 receptor, glial fibrillary acidic protein (GFAP), 2',3'-cyclic nucleotide 3'-phosphodiesterase (CNPase), plp, DM-20, O4, and NG-2 staining.

In another preferred aspect of the present invention there is provided a neural progenitor cell wherein the cell express markers for the neuroectodermal lineage as well as neural markers selected from the group including polysialyated N-CAM, N-CAM, A2B5, nestin, vimentin and the transcriptional factor Pax-6, and do not express Oct-4.

Preferably, the cells do not express the transcriptional factor OCT-4. This may be demonstrated by RT-PCR, or methods of analysis of differential gene expression, microarray analysis or related techniques. More preferably the cells will constitute an enriched preparation. They can proliferate in vitro for prolonged periods at an undifferentiated neural progenitor state to produce a large number of cells. The neural progenitor cells can differentiate, under differentiating conditions to mature neurons and glial cells.

In yet another aspect, the invention provides a neural progenitor cell which is capable of establishing a graft in a recipient brain. Preferably the neural progenitor cell is as described above.

Upon transplantation to the developing brain they incorporate extensively into the host brain, demonstrate wide spread distribution, migrate along established host brain migratory tracks, differentiate in a region specific manner into progeny of the three fundamental neural lineages, indicating their capability to respond to local cues and participate in the development and histogenesis of the living host. This combination of defining properties will identify the neural progenitor cell lines of the invention regardless of the method used for their isolation.

In yet another aspect of the present invention, there is provided a glial cell differentiated from a neural progenitor cell. Preferably, the glial cell is an astrocyte or an oligodendrocyte. Oligodendrocytes may be identified by O4 and NG-2 immunostaining or by RNA transcripts of myelin basic protein (MBP), plp and dm-20.

In a further aspect of the invention, there is provided a method of preparing undifferentiated human embryonic stem cells for differentiation into neural progenitor cells, said method including:
    obtaining an in vitro fertilised human embryo and growing the embryo to a blastocyst stage of development;
    removing inner cells mass (ICM) cells from the embryo;
    culturing ICM cells under conditions which do not induce extraembryonic differentiation and cell death, and promote proliferation of undifferentiated stem cells; and
    recovering the stem cells.

The stem cells will be undifferentiated cells and can be induced to differentiate when a differentiating signal is applied.

In a preferred embodiment of the present invention there is provided a method of preparing undifferentiated human embryonic stem cells for differentiation into neural progenitor cells, said method including:
    obtaining an in vitro fertilised human embryo;
    removing inner cells mass (ICM) cells from the embryo;
    culturing ICM cells on a fibroblast feeder layer to promote proliferation of embryonic stem cells; and
    recovering stem cells from the feeder layer.

Embryonic stem cells (ES) are derived from the embryo. These cells are undifferentiated and have the capability of differentiation to a variety of cell types. The "embryo" is defined as any stage after fertilization up to 8 weeks post conception. It develops from repeated division of cells and includes the stages of a blastocyst stage which comprises an outer trophectoderm and an inner cell mass (ICM).

The embryo required in the present method may be an in vitro fertilised embryo or it may be an embryo derived by transfer of a somatic cell or cell nucleus into an enucleated oocyte of human or non human origin which is then activated and allowed to develop to the blastocyst stage.

The embryo may be fertilised by any in vitro methods available. For instance, the embryo may be fertilised by using conventional insemination, or intracytoplasmic sperm injection.

An embryo that is recovered from cryopreservation is also suitable. An embryo that has been cryopreserved at any stage of development is suitable. Preferably embryos that were cryopreserved at the zygote or cleavage stage are used. Any method of cryopreservation of embryos may be used. It is preferred that a method producing high quality (good morphological grade) embryos is employed.

It is preferred that any embryo culture method is employed but it is most preferred that a method producing high quality (good morphological grade) blastocysts is employed. The high quality of the embryo can be assessed by morphological criteria. Most preferably the inner cell mass is well developed. These criteria can be assessed by the skilled addressee.

Following insemination, embryos may be cultured to the blastocyst stage. Embryo quality at this stage may be assessed to determine suitable embryos for deriving ICM cells. The embryos may be cultured in any medium that maintains their survival and enhances blastocyst development.

Preferably, the embryos are cultured in droplets under pre-equilibrated sterile mineral oil in IVF-50 or Scandinavian 1 (S1) or G1.2 medium (Scandinavian IVF). Preferably the incubation is for two days. If IVF-50 or S1 is used, on the third day, an appropriate medium such as a mixture of 1:1 of IVF-50 and Scandinavian-2 medium (Scandinavian IVF) may be used. From at least the fourth day, a suitable medium such as G2.2 or Scandinavian-2 (S2) medium may be used solely to grow the embryos to blastocyst stage (blastocysts). Preferably, only G2.2 medium is used from the fourth day onwards.

In a preferred embodiment, the blastocyst is subjected to enzymatic digestion to remove the zona pellucida or a portion thereof. Preferably the blastocyst is subjected to the digestion at an expanded blastocyst stage which may be approximately on day 6. Generally this is at approximately six days after insemination.

Any protein enzyme may be used to digest the zona pellucida or portion thereof from the blastocyst. Examples include pronase, acid Tyrodes solution, and mechanical methods such as laser dissection.

Preferably, Pronase is used. The pronase may be dissolved in PBS and G2 or S2 medium. Preferably the PBS and Scandinavian-2 medium is diluted 1:1. For digestion of zona pellucida from the blastocyst, approximately 10 units/ml of Pronase may be used for a period sufficient to remove the zona pellucida. Preferably approximately 1 to 2 mins, more preferably 1 to 1.5 mins is used.

The embryo (expanded blastocyst) may be washed in G2.2 or S2 medium, and further incubated to dissolve the zona pellucida. Preferably, further digestion steps may be used to completely dissolve the zona. More preferably the embryos are further incubated in pronase solution for 15 seconds. Removal of the zona pellucida thereby exposes the trophectoderm.

In a preferred embodiment of the invention the method further includes the following steps to obtain the inner cell mass cell, said steps including:
    treating the embryo to dislodge the trophectoderm of the embryo or a portion thereof;
    washing the embryo with a G2.2 or S2 medium to dislodge the trophectoderm or a portion thereof; and
    obtaining inner cell mass cells of the embryo.

Having had removed the zona pellucida, the ICM and trophectoderm become accessible. Preferably the trophectoderm is separated from the ICM. Any method may be employed to separate the trophectoderm from the ICM. Preferably the embryo (or blastocyst devoid of zona pellucida) is subjected to immuno-surgery. Preferably it is treated with an antibody or antiserum reactive with epitopes on the surface of the trophectoderm. More preferably, the treatment of the embryo, (preferably an embryo at the blastocyst stage devoid of zona pellucida) is combined with treatment with complement. The antibody and/or antiserum and complement treatment may be used separately or together. Preferred combinations of antibody and/or antiserum and complement include anti-placental alkaline phosphatase antibody and Baby Rabbit complement (Serotec) or anti-human serum antibody (Sigma) combined with Guinea Pig complement (Gibco).

Preferably the antibodies and complement are diluted in G2.2 or S2 medium. The antibodies and complement, excluding anti-placental alkaline phosphate (anti-AP) are diluted 1:5 whereas anti-AP antibody is diluted 1:20 with S-2 medium.

Preferably the embryo or blastocyst (preferably having the zona pellucida removed) is subjected to the antibody before it is subjected to the complement. Preferably the embryo or blastocyst is cultured in the antibody for a period of approximately 30 mins.

Following the antibody exposure, it is preferred that the embryo is washed. Preferably it is washed in G2.2 or S2 medium. The embryo or blastocyst preferably is then subjected to complement, preferably for a period of approximately 30 mins.

G2.2 or S2 (Scandinavian-2) medium is preferably used to wash the embryo or blastocyst to dislodge the trophectoderm or a portion thereof.

Dislodgment may be by mechanical means. Preferably the dislodgment is by pipetting the blastocyst through a small bore pipette.

The ICM cells may then be exposed and ready for removal and culturing. Culturing of the ICM cells may be conducted on a fibroblast feeder layer. In the absence of a fibroblast feeder layer, the cells will differentiate. Leukaemia inhibitory factor (LIF) has been shown to replace the feeder layer in some cases and maintain the cells in an undifferentiated state. However, this seems to only work for mouse cells. For human cells, high concentrations of LIF were unable to maintain the cells in an undifferentiated state in the absence of a fibroblast feeder layer.

The conditions which do not induce extraembryonic differentiation and cell death may include cultivating the embryonic stem cells on a fibroblast feeder layer which does not induce extraembryonic differentiation and cell death.

Mouse or human fibroblasts are preferably used. They may be used separately or in combination. Human fibroblasts provide support for stem cells, but they create a non-even and sometimes non-stable feeder layer. However, they may combine effectively with mouse fibroblasts to obtain an optimal stem cell growth and inhibition of differentiation.

The cell density of the fibroblast layer affects its stability and performance. A density of approximately 25,000 human and 70,000 mouse cells per $cm^2$ is most preferred. Mouse fibroblasts alone are used at 75,000-100,000/$cm^2$. The feeder layers are preferably established 6-48 hours prior to addition of ES or ICM cells.

Preferably the mouse or human fibroblast cells are low passage number cells. The quality of the fibroblast cells affects their ability to support the stem cells. Embryonic fibroblasts are preferred. For mouse cells, they may be obtained from 13.5 day old foetuses. Human fibroblasts may be derived from embryonic or foetal tissue from termination of pregnancy and may be cultivated using standard protocols of cell culture.

The guidelines for handling the mouse embryonic fibroblasts may include minimising the use of trypsin digestion and avoidance of overcrowding in the culture. Embryonic fibroblasts that are not handled accordingly will fail to support the growth of undifferentiated ES cells. Each batch of newly derived mouse embryonic fibroblasts is tested to confirm its suitability for support and maintenance of stem cells.

Fresh primary embryonic fibroblasts are preferred in supporting stem cell renewal and/or induction of somatic differentiation as compared to frozen-thawed fibroblasts. Nevertheless, some batches will retain their supportive potential after repeated freezing and thawing. Therefore each fresh batch that has proved efficient in supporting ES cells renewal and/or induction of somatic differentiation is retested after freezing and thawing. Batches that retain their potential after freezing and thawing are most preferably used. Batches are tested to determine suitability for the support of stem cell renewal, the induction of somatic differentiation or the induction of extraembryonic differentiation.

Some mouse strains yield embryonic fibroblasts which are more suitable for stem cell maintenance and induction of somatic differentiation than those of other strains. For example, fibroblasts derived from inbred 129/Sv or CBA mice or mice from a cross of 129/Sv with C57/B16 strains have proven highly suitable for stem cell maintenance.

Isolated ICM masses may be plated and grown in culture conditions suitable for human stem cells.

It is preferred that the feeder cells are treated to arrest their growth. Several methods are available. It is preferred that they are irradiated or are treated with chemicals such as mitomycin C that arrests their growth. Most preferably, the fibroblast feeder cells are treated with mitomycin C (Sigma).

The fibroblast feeder layer maybe generally plated on a gelatin treated dish. Preferably, the tissue culture dish is treated with 0.1% gelatin.

The fibroblast feeder layer may also contain modified fibroblasts. For instance, fibroblasts expressing recombinant membrane bound factors essential for stem cell renewal may be used. Such factors may include for example human multipotent stem cell factor.

Inner cell mass cells may be cultured on the fibroblast feeder layer and maintained in an ES medium. A suitable medium is DMEM (GIBCO, without sodium pyruvate, with glucose 4500 mg/L) supplemented with 20% FBS (Hyclone, Utah), (betamercaptoethanol—0.1 mM (GIBCO), non essential amino acids—NEAA 1% (GIBCO), glutamine 2 mM. (GIBCO), and penicillin 50 µ/ml, streptomycin 50 µg/ml (GIBCO). In the early stages of ES cell cultivation, the medium maybe supplemented with human recombinant leukemia inhibitory factor hLIF preferably at 2000 µ/ml. However, LIF generally is not necessary. Any medium may be used that can support the ES cells.

The ES medium may be further supplemented with soluble growth factors which promote stem cell growth or survival or inhibit stem cell differentiation. Examples of such factors include human multipotent stem cell factor, or embryonic stem cell renewal factor.

The isolated ICM may be cultured for at least six days. At this stage, a colony of cells develops. This colony is comprised principally of undifferentiated stem cells. They may exist on top of differentiated cells.

Isolation of the undifferentiated cells may be achieved by chemical or mechanical means or both. Preferably mechanical isolation and removal by a micropipette is used. Mechanical isolation may be combined with a chemical or enzymatic treatment to aid with dissociation of the cells, such as $Ca^{2+}/Mg^{2+}$ free PBS medium or dispase.

In a further preferred embodiment of the invention, the method further includes:
  replating the stem cells from the fibroblast feeder layer onto another fibroblast feeder layer; and
  culturing the stem cells for a period sufficient to obtain proliferation of morphologically undifferentiated stem cells.

A further replating of the undifferentiated stem cells is performed. The isolated clumps of cells from the first fibroblast feeder layer may be replated on fresh human/mouse fibroblast feeder layer in the same medium as described above.

Preferably, the cells are cultured for a period of 7-14 days. After this period, colonies of undifferentiated stem cells may be observed. The stem cells may be morphologically identified preferably by the high nuclear/cytoplasmic ratios, prominent nucleoli and compact colony formation. The cell borders are often distinct and the colonies are often flatter than mouse ES cells. The colonies resemble those formed by pluripotent human embryonal carcinoma cell lines such as GCT 27 X-1.

In another embodiment of the invention, the method further includes propagating the undifferentiated stem cells. The methods of propagation may initially involve removing clumps of undifferentiated stem cells from colonies of cells. The dispersion is preferably by chemical or mechanical means or both. More preferably, the cells are washed in a $Ca^{2+}/Mg^{2+}$ free PBS or they are mechanically severed from the colonies or a combination of these methods or any known methods available to the skilled addressee. In these methods, cells may be propagated as clumps of about 100 cells about every 7 days.

In the first method, $Ca^{2+}/Mg^{2+}$ free PBS medium may be used to reduce cell-cell attachments. Following about 15-20 minutes, cells gradually start to dissociate from the monolayer and from each other and desired size clumps can be isolated. When cell dissociation is partial, mechanical dissociation using the sharp edge of the pipette may assist with cutting and the isolation of the clumps.

An alternative chemical method may include the use of an enzyme. The enzyme may be used alone or in combination with a mechanical method. Preferably, the enzyme is dispase.

An alternative approach includes the combined use of mechanical cutting of the colonies followed by isolation of the subcolonies by dispase. Cutting of the colonies may be performed in PBS containing $Ca^{2+}$ and $Mg^{2+}$. The sharp edge of a micropipette may be used to cut the colonies to clumps of about 100 cells. The pipette may be used to scrape and remove areas of the colonies. The PBS is preferably changed to regular equilibrated human stem cell medium containing dispase (Gibco) 10 mg/ml and incubated for approximately 5 minutes at 37° C. in a humidified atmosphere containing 5% $CO_2$. As soon as the clumps detached they may be picked up by a wide bore micro-pipette, washed in PBS containing $Ca^{2+}$ and $Mg^{2+}$ and transferred to a fresh fibroblast feeder layer.

The fibroblast feeder layer may be as described above.

Undifferentiated embryonic stem cells have a characteristic morphology as described above. Other means of identifying the stem cells may be by cell markers or by measuring expression of genes characteristic of pluripotent cells.

Examples of genes characteristic of pluripotent cells or particular lineages may include (but are not limited to) Oct-4 and Pax-6, polysialyated N-CAM, N-CAM, A2B5, nestin and vimentin as markers of stem cells and neuronal precursors respectively. Other genes characteristic of stem cells may include Genesis, GDF-3 and Cripto. CD-34 is characteristic of hematopoietic stem cells and flk-1 is expressed by the hemangioblast. AC-133 may be characteristic of both hematopoietic and neural progenitors. Keratin is characteristic of epidermal cells while transferin, amylase and a1 antitrypsin are characteristic of embryonic endoderm. Such gene expression profiles may be attained by any method including RT-PCR, methods of differential gene expression, microarray analysis or related techniques.

Preferably the stem cells may be identified by being immunoreactive with markers for human pluripotent stem cells including SSEA-4, GCTM-2 antigen, TRA 1-60. Preferably the cells express the transcription factor Oct-4. The cells also maintain a diploid karyotype.

Preferably the neural progenitor cells are identified by expressed markers of primitive neuroectoderm and neural stem cells such as N-CAM, polysialyated N-CAM, A2B5, intermediate filament proteins such as nestin and vimentin and the transcription factor Pax-6. Neurons may be identified by structural markers such as β-tubulin, β-tubulin III, the 68 kDa and the 200 kDa neurofilament proteins. Mature neurons may also be identified by the 160 kDa neurofilament proteins, Map-2a, b and synaptophysin, glutamate, GABA, serotonin, tyrosine hydroxylase, GABA biosynthesis and receptor subunits characteristic of GABA minergic neurons (GABA Aα2). Astrocytes may be identified by the expression of glial fibrillary acidic protein (GFAP), and oligodendrocyte by 2',3'-cyclic nucleotide 3'-phosphodiesterase (CNPase), plp, DM-20, myelin basic protein (MBP), NG-2 staining and O4.

The stem cells may be further modified at any stage of isolation. They may be genetically modified through introduction of vectors expressing a selectable marker under the control of a stem cell specific promoter such as Oct-4. Some differentiated progeny of embryonic stem cells may produce products that are inhibitory to stem cell renewal or survival. Therefore selection against such differentiated cells, facilitated by the introduction of a construct such as that described above, may promote stem cell growth and prevent differentiation.

The stem cells may be genetically modified at any stage with markers so that the markers are carried through to any stage of cultivation. The markers may be used to purify the differentiated or undifferentiated stem cell population at any stage of cultivation.

Genetic construct may be inserted to undifferentiated or differentiated cells at any stage of cultivation. The genetically modified cells may be used after transplantation to carry and express genes in target organs in the course of gene therapy.

Progress of the stem cells and their maintenance in a differentiated or undifferentiated stage may be monitored in a quantitative fashion by the measurement of stem cell specific secreted products into the culture medium or in fixed preparations of the cells using ELISA or related techniques. Such stem cell specific products might include the soluble form of the CD30 antigen or the GCTM-2 antigen or they may be monitored as described above using cell markers or gene expression.

In another aspect of the invention there is provided a method of inducing somatic differentiation of stem cells in vitro into progenitor cells said method comprising:
  obtaining undifferentiated stem cells; and
  providing a differentiating signal under conditions which are non-permissive for stem cell renewal, do not kill cells and/or induces unidirectional differentiation toward extraembryonic lineages.

The undifferentiated cell lines of the present invention may be cultured indefinitely until a differentiating signal is given. Preferably, they are cultured under the conditions described above.

In the presence of a differentiation signal, undifferentiated ES cells in the right conditions will differentiate into derivatives of the embryonic germ layers (endoderm, mesoderm and ectoderm) such as neuron tissue, and/or extraembryonic tissues. This differentiation process can be controlled.

This method is useful for directing stem cells to differentiate toward a somatic lineage. Furthermore, the method allows the establishment of a pure preparation of progenitor cells from a desired lineage and the elimination of unwanted differentiated cells from other lineages. The method facilitates the establishment of a pure somatic progenitor cell line.

The method may be used to derive an enriched preparation of a variety of somatic progenitors such as but not limited to mesodermal progenitors (such as hemangioblast or hematopoietic stem cells) and neural progenitors. Preferably the method is used to derive neural progenitors.

Conditions for obtaining differentiated cultures of somatic cells from embryonic stem cells are those which are non-permissive for stem cell renewal, but do not kill stem cells or drive them to differentiate exclusively into extraembryonic lineages. A gradual withdrawal from optimal conditions for stem cell growth favours somatic differentiation. The stem cells are initially in an undifferentiated state and can be induced to differentiate.

In a preferred embodiment of the present invention, there is provided a method of inducing somatic differentiation of stem cells in vitro into progenitor cells, said method comprising:
  obtaining undifferentiated stem cells; and
  culturing said cells for prolonged periods and at high density on a fibroblast feeder cell layer to induce differentiation.

In another preferred embodiment of the present invention, there is provided a method of inducing somatic differentiation of stem cells in vitro into progenitor cells, said method comprising:
  obtaining undifferentiated stem cells; and
  transferring said cells into serum free media to induce differentiation.

The stem cells may be undifferentiated stem cells and derived from any source or process which provides viable undifferentiated stem cells. The methods described above for retrieving stem cells from embryos is most preferred.

In these preferred aspects, the conditions of culturing the cells at high density on a fibroblast feeder cell layer or transferring to a serum free medium are intended to be non-permissive for stem cell renewal or cause uni-directional differentiation toward extraembryonic lineages.

Generally the presence of a fibroblast feeder layer will maintain these cells in an undifferentiated state. This has been found to be the case with the cultivation of mouse and human ES cells. However, without being restricted by theory, it has now become evident that the type and handling of the fibroblast feeder layer is important for maintaining the cells in an undifferentiated state or inducing differentiation of the stem cells.

Suitable fibroblast feeder layers are discussed above.

Somatic differentiation in vitro of the ES cell lines is a function of the period of cultivation following subculture, the density of the culture, and the fibroblast feeder cell layer. It has been found that somatic differentiation may be detected as early as the first week after subculture and is morphologically apparent and demonstrable by immunochemistry approximately 14 days following routine subcultivation as described above in areas of the colony which are remote from direct contact with the feeder cell layer (in contrast to areas adjacent to the feeder cell layer where rapid stem cell growth is occurring such as the periphery of a colony at earlier time points after subcultivation), or in cultures which have reached confluence. Depending upon the method of preparation and handling of the mouse embryo fibroblasts, the mouse strain from which the fibroblasts are derived, and the quality of a particular batch, stem cell renewal, extraembryonic differentiation or somatic differentiation may be favoured.

Once a suitable fibroblast cell line is selected, it may be used as a differentiation inducing fibroblast feeder layer to induce the undifferentiated stem cells to differentiate into a somatic lineage or multiple somatic lineages. These may be identified using markers or gene expression as described above. Preferably the fibroblast feeder layer does not induce extraembryonic differentiation and cell death.

The modulation of stem cell growth by appropriate use of fibroblast feeder layer and manipulation of the culture conditions thus provides an example whereby somatic differentiation may be induced in vitro concomitant with the limitation of stem cell renewal without the induction of widespread cell death or extraembryonic differentiation.

Other manipulations of the culture conditions such as culturing in various compositions of serum free medium may be used to arrest stem cell renewal without causing stem cell death or unidirectional extraembryonic differentiation, thereby favouring differentiation of somatic cells.

Differentiation may also be induced by culturing to a high density in monolayer or on semi-permeable membranes so as to create structures mimicing the postimplantation phase of human development, or any modification of this approach. Cultivation in the presence of cell types representative of those known to modulate growth and differentiation in the vertebrate embryo (eg. endoderm cells or cells derived from normal embryonic or neoplastic tissue) or in adult tissues (eg. bone marrow stromal preparation) may also induce differentiation, modulate differentiation or induce maturation of cells within specific cell lineage so as to favour the establishment of particular cell lineages.

Chemical differentiation may also be used to induce differentiation. Propagation in the presence of soluble or membrane bound factors known to modulate differentiation of vertebrate embryonic cells, such as bone morphogenetic protein-2 or antagonists of such factors, may be used.

Applicants have found that Oct-4 is expressed in stem cells and down-regulated during differentiation and this strongly indicates that stem cell selection using drug resistance genes driven by the Oct-4 promoter will be a useful avenue for manipulating human ES cells. Directed differentiation using growth factors, or the complementary strategy of lineage selection coupled with growth factor enhancement could enable the selection of populations of pure committed progenitor cells from spontaneously differentiating cells generated as described here.

Genetic modification of the stem cells or further modification of those genetically modified stem cells described above may be employed to control the induction of differentiation. Genetic modification of the stem cells so as to introduce a construct containing a selectable marker under the control of a promoter expressed only in specific cell lineages, followed by treatment of the cells as described above and the subsequent selection for cells in which that promoter is active may be used.

Once the cells have been induced to differentiate, the various cell types, identified by means described above, may be separated and selectively cultivated. Preferably neural progenitor cells are selected. These progenitors are capable of differentiating into neuron cells and/or glial cells. More preferably, they will differentiate into neuron cells and/or glial cells in the absence of other differentiated cells such as those from the extra embryonic lineage.

Selective cultivation means isolation of specific lineages of progenitors or mature differentiated cells from mixed populations preferably appearing under conditions unfavourable for stem cell growth and subsequent propagation of these specific lineages. Selective cultivation may be used to isolate populations of mature cells or populations of lineage specific committed progenitor cells. Isolation may be achieved by various techniques in cell biology including the following alone or in combination: microdissection; immunological selection by labelling with antibodies against epitopes expressed by specific lineages of differentiated cells followed by direct isolation under fluorescence microscopy, panning, immunomagnetic selection, or selection by flow cytometry; selective conditions favouring the growth or adhesion of specific cell lineages such as exposure to particular growth or extracellular matrix factors or selective cell-cell adhesion; separation on the basis of biophysical properties of the cells such as density; disaggregation of mixed populations of cells followed by isolation and cultivation of small clumps of cells or single cells in separate culture vessels and selection on the basis of morphology, secretion of marker proteins, antigen expression, growth properties, or gene expression; lineage selection using lineage specific promoter constructs driving selectable markers or other reporters.

The derivation of neural progenitors from ES cells, and even further more, the establishment of a pure neural progenitor cell line is described below as proof of the above principles. The following description is illustrative of neural progenitor cells as somatic cells differentiated from stem cells and should not be taken as a restriction on the generality of the invention. It should be noted that the method may be used to derive an enriched preparation of a variety of somatic progenitors such as but not limited to mesodermal progenitors such as hemangioblast or hematopoietic stem cells or neural progenitors. Transdifferentiation to non-neuronal phenotypes from neural progenitors is within the scope of the present invention and may result in hematopoietic, endothelial, embryonic endoderm and ectodermal cells.

The establishment of neural progenitor cells from embryonic stem cells and more preferably a pure preparation of neural progenitor cells and even more preferably a neural progenitor cell line may be achieved by any one or combination of the following approaches.

In one preferred approach, somatic differentiation of ES cells is induced by prolonged culture of ES cells to high density on an appropriate fibroblast feeder layer that prevents unidirectional differentiation towards extraembryonic lineage and promotes somatic differentiation. Once the cells have been induced to differentiate toward somatic lineages, areas which are destined to give rise to clusters of mainly neural progenitor cells may be identified based on characteristic morphological features as described above. The size and demarcation of these areas may be enhanced by replacing the growth medium with serum free medium supplemented with EGF and bFGF. The areas are separated mechanically and replated in serum-free medium, whereupon they form spherical structures.

Any serum free medium may be used. Preferably NS-A (Euroclone) or DMEM/F12 (Gibco) is used. More preferably NS-A or DMEM/F12 supplemented with N2 or B27 (Gibco) is used. Most preferably DMEM/F12 supplemented with B27 is used.

In the presence of an appropriate supplement of growth factors such as but not limited to, EGF and basic FGF to the serum free medium, the neural progenitors may be cultivated and expanded to establish a cell line. The growth factors inhibit further differentiation of the progenitor cells and promote their proliferation.

The culture in the serum free medium and preferably growth factors is selective and therefore limits prolonged proliferation of other types of differentiated cells such as the progeny of the extraembryonic lineage that may coexist in the culture. Therefore the cultivation in these selective conditions may be used to establish an enriched cell line of neural progenitors.

The progenitors may be cultured as spheres or as a monolayer. Subculturing may be conducted mechanically. Scraping is preferred to propagate monolayer cultures. However, any mechanical method such as tituration or cutting may be used to subculture the spheres. Most preferably the spheres are sliced into smaller clumps. The progenitors may be expanded to produce a large number of cells.

In another preferred approach, the method involves the transfer of undifferentiated stem cells into culture conditions that on one hand direct differentiation toward a desired somatic lineage, which is the neural lineage in this case, while on the other hand are selective and therefore limit both the differentiation toward unwanted lineages (such as extraembryonic lineages) as well as the survival of differentiated cells from these lineages.

Such culture conditions include the transfer into serum free media (as described above) that may be supplemented with growth factors including but not limited to bFGF and EGF. The serum free media promotes differentiation towards the neuroectodermal lineage (and possibly other non-neural lineages such as mesoderm). The serum free media may limit the growth and survival of unwanted cells such as those from the extraembryonic lineages.

In a further preferred embodiment of the invention, the method allows the establishment of a pure progenitor cell line from the desired lineage.

Growth factors that are added to the medium may promote the proliferation and the cultivation of the desired somatic progenitors such as neural progenitors. The selective culture conditions further eliminate during cultivation, unwanted differentiated cells from other lineages such as extraembryonic lineages. The method may be used to derive a pure preparation and/or a pure cell line of a variety of somatic progenitors including, but not limited to, neural progenitor, mesodermal progenitors such as hemangioblast or hematopoietic stem cells and progenitors of the endodermal lineage.

Preferably, in the derivation of an enriched cell line of neural progenitors, clumps of undifferentiated stem cells may be transferred into plastic tissue culture dishes containing serum free medium. The serum free medium induces the differentiation of the ES cells initially towards ectoderm and then towards the neuroectodermal lineage.

Figure 9:
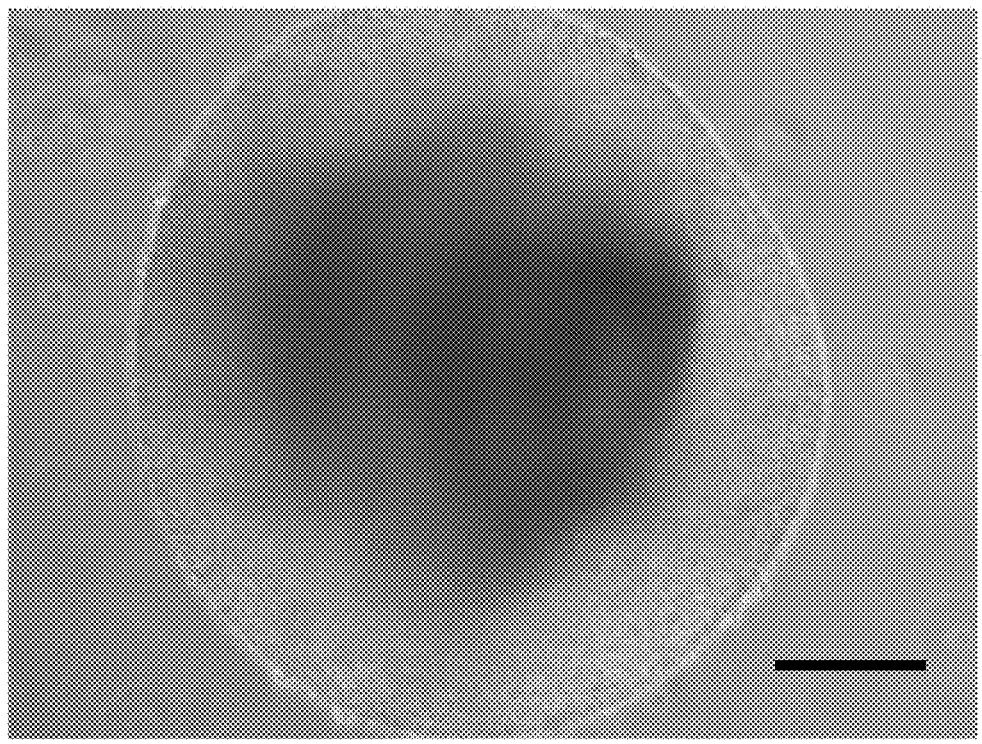
FIG. 9 shows phase contrast appearance of a sphere that is formed 72 hours after the transfer of a clump of undifferentiated ES cells into serum free medium (Scale bar 100 microns).

Any serum free medium may be used. Preferably NS-A medium (Euroclone) or DMEM/F12 is used. More preferably the serum free medium is supplemented with N2 or B27 (Gibco). Most preferably the medium is DMEM/F12 supplemented with B27. The clusters of undifferentiated stem cells turn into round spheres within approximately 24 hours after transfer (FIG. 9).

The serum free medium may be further supplemented with basic FGF and EGF to promote proliferation of neural progenitors in an undifferentiated state. The progenitors may be cultivated under these conditions for prolonged periods. The selective conditions that are induced by the serum free medium and growth factors result in a gradual purification and elimination of other differentiated cell types during cultivation.

The progenitors may be cultured as spheres or as a monolayer. Subculturing may be conducted mechanically. Scraping is preferred to propagate monolayer cultures. Any mechanical method known to the skilled addressee such as tituration or cutting may be used to subculture the spheres. Most preferably the spheres are sliced into smaller clumps. The progenitors may be expanded to produce a large number of cells.

The progenitors that are generated directly from undifferentiated stem cells have similar properties to the neural progenitors that are generated from differentiating stem cells colonies. They express the same markers of primitive neuroectoderm and neural progenitor cells, such as N-CAM, polysialyated N-CAM, the intermediate filament protein nestin, Vimentin and the transcription factor Pax-6. They do not express the transcriptional factor oct-4. They have a similar growth potential. They generate differentiated neural cells with similar morphology and marker expression after plating on appropriate substrate and withdrawal of growth factors.

In another aspect of the invention, there is provided a method of inducing somatic cells from embryonic stem cell derived somatic progenitors, said method comprising:
 obtaining a source of embryonic stem cell derived somatic progenitor cells;
 culturing the progenitor cells on an adhesive substrate; and
 inducing the cells to differentiate to somatic cells under conditions which favour somatic differentiation.

The source of embryonic stem cell derived progenitor cells may be from any source. However, they are preferably established by the methods described above. Preferably, the cells are grown in the presence of a serum-free media and growth factor.

The somatic cells may preferably be neurons, or glial cells including astrocytes or oligodendrocyte cells. Preferably, the somatic progenitors are neural progenitors.

Any adhesive substrate may be used. More preferably, poly-D-lysine and laminin or poly-D-lysine and fibronectin are used.

Induction of somatic cells is preferably achieved by withdrawing growth factors from the media. However, other acceptable methods of induction may be used. These may include:
 culturing the undifferentiated cells for prolonged periods and at high density to induce differentiation;
 culturing the cells in serum free media;
 culturing the cells on a differentiation inducing fibroblast feeder layer and wherein said fibroblast feeder layer does not induce extra embryonic differentiation and cell death;
 culturing to a high density in monolayer or on semi-permeable membrane so as to create structures mimicing the postimplantation phase of human development; or
 culturing in the presence of a chemical differentiation factor selected from the group including bone morphogenic protein-2 or antagonists thereof.

For inducing neurons, it is preferred to further use poly-D-lysine and laminin. Upon plating of neural progenitors on an appropriate substrate such as poly-D-lysine and laminin, and withdrawal of growth factors from the serum free medium, differentiated cells grow out of the spheres as a monolayer and acquire morphology of mature neurons and expression of markers such as the 160 kDa neurofilament protein, Map-2AB, synaptophysin, Glutamate, GABA, serotonin, tyrosine hydroxylase, GABA biosynthesis and receptor subunits characteristic of GABA minergic neurons (GABA A$\alpha$2) which are characteristic of mature neurons.

In a preferred embodiment, the method for inducing neurons further includes culturing the somatic progenitor cells, preferably undifferentiated neural progenitor cells, or differentiating neuronal progenitors in the presence of retinoic acid.

Retinoic acid has been found to further induce differentiation toward mature neurons.

Accordingly, there is provided a mature neuron cell prepared by the method described herein. The mature neuron cell may be characterized in that it expresses 160 kDa neurofilament protein, MAP2ab, glutamate, synaptophysin, glutamic acid decarboxylase (GAD), tyrosine hydroxylase, GABA and serotonin.

The establishment of oligodendrocyte and astrocyte cells indicates the potential of the neural precursors to differentiate towards the glial lineage.

For inducing of glial cells including astrocytes and oligodendrocyte progenitors, it is preferred to use poly-D-lysine and fibronectin. Fibronectin is significantly more potent than laminin for the induction of differentiation towards the glial lineage.

In a preferred embodiment, the method for inducing glial cells further includes culturing the somatic progenitor cells, preferably undifferentiated neural progenitor cells, in the presence of PDGF-AA and basic FGF.

In yet another preferred embodiment, the method for inducing glial cells further includes culturing the somatic progenitor cells, preferably undifferentiated neural progenitor cells, in the presence of T3. The cells may be then grown in the absence of growth factor.

The glial cells may be selected from astrocytes or oligodendrocytes. The oligodendrocytes derived from the methods of the present invention may be identified and characterized by RNA transcripts of MBP, plp and dm-20 or by immunostaining for O4 and NG2.

Culture in serum free medium supplemented with b-FGF and PDGF-AA may direct the neural progenitors to turn into glial progenitors and induce the expansion of glial progenitors. This is followed by plating the progenitors on poly-D-lysine and fibronectin and further culture in the presence of the growth factors and T3 followed by culture in the presence of T3 without growth factor supplementation. Without being limited by theory, it is postulated that the growth factors such as bFGF and PDGF-AA facilitate proliferation and spreading of the glial progenitors, fibronectin further induces differentiation towards the glial lineage and T3 induce the differentiation toward and along the oligodendrocyte lineage.

In another aspect, differentiation into glial cells including astrocyte and oligodendrocyte cells is induced by plating the neural progenitors on poly-D-lysine and fibronectin and culturing them in the serum free medium supplemented with EGF, b-FGF and PDGF-AA. The growth factors may then be removed and the cells further cultured in the presence of T3.

In yet another aspect, the invention provides differentiated somatic cells including neural, neural progenitor cells, neuronal and/or glial cells prepared by the methods of the present invention. The glial cells include astrocytes or oligodendrocytes. The oligodendrocytes derived by the methods of the present invention may be characterized by RNA transcripts of MBP, plp and dm-20 or by immunostaining for O4 and NG2.

The progenitor cells that are derived by the method that is described above may be used to generate differentiated cells from other lineages. The spheres of progenitors may include in addition to neural progenitors more primitive cells such as primitive ectodermal cells or progenitor cells of other lineages such as the hemangioblast endothelial or hematopoietic stem cells, embryonic endodermal cells and ectoderm. By manipulation of the culture conditions these primitive cells may generate all somatic cell types.

Expression of mesodermal markers such as flk-1, AC-133 and CD-34, embryonic endodermal markers such as transferin, amylase and α1 anti trypsin and the epidermal marker keratin has been demonstrated in the human ES derived progenitor cell preparation. This may indicate the presence of primitive cells from non-neural lineages such as the hemangioblast cell or hematopoietic stem cell within the neural progenitors preparation. Alternatively it may be that the primitive neural progenitors within the spheres express these markers. The expression of the markers may indicate the possible high plasticity of the neural progenitors to transdifferentiate into cells of other lineages.

The present invention provides a method that generates an in vitro and in vivo model of controlled differentiation of ES cells towards the neural lineage. The model, and the cells that are generated along the pathway of neural differentiation may be used for the study of the cellular and molecular biology of human neural development, for the discovery of genes, growth factors, and differentiation factors that play a role in neural differentiation and regeneration. The model, and the cells that are generated along the pathway of neural differentiation may be used for drug discovery and for the development of screening assays for teratogenic, toxic and neuroprotective effects.

In a further aspect of the invention, there is provided a method of producing large quantities of differentiated and undifferentiated cells. It is intended to mean that these cells can be propagated, expanded and grown in cell culture.

In yet another aspect, the present invention provides a method of producing an enriched preparation of human ES derived neural progenitor cells, said method comprising:
  obtaining an undifferentiated human embryonic stem cell as described herein;
  inducing somatic differentiation of the embryonic stem cell to a neural progenitor cell by a method described herein;
  identifying a neural progenitor cell by expressed markers of primitive neuroectoderm and neural stem cells such as N-CAM, polysialyated N-CAM, A2B5, intermediate filament proteins such as nestin and vimentin and the transcription factor Pax-6; and
  culturing the neural progenitor cells to promote proliferation and propagation.

The neural progenitor cells will grow as spheres or monolayers preferably in serum free media. A suitable media is DMEM/F12 supplemented with growth factors selected from the group including B27, EGF and bFGF.

Further enrichment of the preparation may be achieved by further cultivation in new media that includes transferring the clumps of cells into new media.

In a further aspect of the invention there is provided a method to dis-aggregate the spheres into single cell suspensions. Dis-aggregation by using digestion with trypsin or dispase may be ineffective. Dis-aggregation may be accomplished by digestion with papain combined with mechanical tituration.

In another aspect of the invention, there is provided a method of transplanting ES derived neural progenitor spheres, said method comprising:
  disaggregating the spheres; and
  injecting the disaggregated spheres into a living host.

Disaggregation of the spheres may be conducted in any way to separate the cells either to small clumps or single cells. Ideally, trypsin or dispase are not used. Mechanical disaggregation or tituration may be adopted to separate the cells prior to injection. Alternatively the spheres may be disaggregated by digestion with papain preferably combined with mechanical tituration.

Injection may be conducted in any manner so as to introduce the cells into the nervous system of the host. Preferably the cells are introduced into a specific site in the nervous system. Any method may be used to introduce the cells into a specific location. Preferably, the cells are injected using a micro-glass pipette (300 micron outer diameter) connected to a micro-injector (Narishige, Japan). The glass pipette may be covered by a plastic sleeve that will limit the depth of penetration into the host nervous system. The cells may be also injected by a hamilton syringe into predetermined depth using a stereotaxic device. Any stereotaxic injection method may be suitable.

The volume that is injected and the concentration of cells in the transplanted solution depend on the indication for transplantation, the location in the nervous system and the species of the host. Preferably 2 microliters with 25,000-50,000 cells per microliter are injected to the lateral cerebral ventricles of newborn rats or mice.

In another aspect of the invention there is provided a neural progenitor cell capable of transplantation into a host nervous system said cell characterised by establishing a stable graft and contributing in the histogenesis of a living host.

In another aspect of the present invention there is provided a method of inducing somatic cells in vivo from embryonic stem cell derived somatic progenitors, said method comprising:

obtaining a source of embryonic stem cell derived somatic progenitor cells, preferably prepared by the methods described herein; and transplanting the somatic progenitors into a host to induce differentiation to somatic cells.

The transplanting may be conducted by any of the methods described herein.

When engrafted into a developing nervous system, the progenitor cells of the present invention will participate in the processes of normal development and will respond to the host's developmental cues. The engrafted progenitor cells will migrate along established migratory pathways and will spread widely into disseminated areas of the nervous system. The transplanted cells will respond to host environmental signals, differentiate in a temporally and regionally appropriate manner into progeny from both the neuronal and glial lineages in accord to the region's stage of development and in concert with the host developmental program. The engrafted neural progenitor cell is capable of non-disruptive intermingling with the host neural progenitors as well as differentiated cells. The transplanted cells can replace specific deficient neuronal or glial cell populations, restore defective functions and can express foreign genes in a wide distribution.

In a further aspect of the invention the ES derived neural progenitor cells or their differentiated progeny may be transplanted into the developed nervous system. They can form a stable graft, migrate within the host nervous system, intermingle and interact with the host neural progenitors and differentiated cells. They can replace specific deficient neuronal or glial cell populations, restore deficient functions and activate regenerative and healing processes in the host's nervous system. In an even further aspect of the invention the transplanted cells can express foreign genes in the host's nervous system.

Preferably the stable graft is a graft established in the central nervous system or the peripheral nervous system. The stable graft may establish in the brain. The neural progenitor cells of the present invention have been shown by the applicants to differentiate to mature neurons characterized by their ability to express 160 kDa neuro-filament protein, MAP2ab, glutamate, synaptophysin, glutamic acid decarboxylase (GAD), tyrosine hydroxylase, GABA and serotonin. The neural progenitor cells of the present invention have been also shown by the applicants to differentiate to astrocyte and oligodendrocyte characterized by RNA transcripts of GFAP, MBP, plp and dm-20 or by immunostaining for GFAP, O4 and NG2.

The ability to differentiate to the various somatic cell types is particularly useful for modifying the nervous system for replacing deficient neuronal or glial cell populations, restoring deficient functions of the system, or activating regenerative and healing processes in the nervous system.

In a further aspect of the invention the progenitor cells are grafted into other organs such as but not limited to the hematopoietic system where they trans-differentiate and form a stable functional graft.

More preferably the spheres are ES derived human neural progenitor spheres which are transplanted into the living host.

In yet another aspect of the present invention, there is provided a method of treating a mental condition by replenishing a cell population in the brain, said method comprising:

obtaining a source of embryonic stem cell derived somatic progenitor cells, preferably prepared by the methods described herein; and transplanting the somatic progenitors into a host to promote their differentiation to somatic cells.

Preferably, they are differentiated from neural lineages selected from neurons, astrocytes and oligodendrocyte.

Preferably the mental condition is selected from the group including alzheimers disease, and other mental conditions causing dementia. It is shown that mature neurons of the present invention express glutamate, TH, GABA and serotonin. Serotoninergic neurons may have a role in the pathogenesis and treatment of mental conditions.

In a further aspect of the invention there is provided a neural progenitor cell, a neuronal cell and/or a glial cell that may be used for cell therapy in a variety of pathological conditions including but not limited to neurodegenerative disorders, vascular conditions, autoimmune disorders, congenital disorders, trauma and others.

In a further aspect of the invention there is provided a neural progenitor cell, a neuronal cell and/or a glial cell that may be used for gene therapy. Genetically manipulated neural progenitor cells or neuronal cell or glial cells may be used after transplantation as a vector to carry and express desired genes at target organs.

In another aspect of the present invention, there is provided a committed progenitor cell line. The progenitor cell line may be expanded to produce large quantities of progenitor cells, neural progenitor cells, neuronal cells, mature neuronal cells and glial cells.

In another aspect of the invention, there are provided committed neural progenitor cells capable of self renewal or differentiation into one or limited number of somatic cell lineages, as well as mature differentiated cell produced by the methods of the present invention.

Expansion of the committed progenitor cells may be useful when the number of progenitors that may be derived from ES cells is limited. In such a case, expansion of the progenitors may be useful for various applications such as the production of sufficient cells for transplantation therapy, for the production of sufficient RNA for gene discovery studies etc. For example, by using the techniques described above, expansion of progenitor cells from ten spheres for ten passages may generate $50 \times 10^6$ cells that would be sufficient for any application.

These observations on cells of the neural lineage establish the principle that by using the techniques described, committed progenitor cells may be isolated, from embryonic stem cell cultures propagated, expanded, enriched and further induced to produce fully differentiated cells.

In a further aspect of the invention, there is provided a method of producing large quantities of differentiated and undifferentiated cells.

In another aspect there is provided a differentiated committed progenitor cell line that may be cultivated for prolonged periods and give rise to large quantities of progenitor cells and fully differentiated cells.

The neural progenitor cells or other committed progenitor cells derived by the method described above may be used to generate differentiated cells from other lineages by transdifferentiation.

In another aspect there is provided a differentiated committed progenitor cell line capable of differentiation into mature neurons and/or glial cells. Preferably the progenitor cell is a neural progenitor cell.

In another aspect there is provided an undifferentiated cell line capable of differentiation into neural progenitor cells produced by the method of the present invention.

Specific cell lines HES-1 and HES-2 were isolated by the procedures described above and have the properties described above.

In another aspect of the invention there is provided a cell composition including a human differentiated or undifferentiated cell capable of differentiation into neural progenitor cells preferably produced by the method of the present invention, and a carrier.

The carrier may be any physiologically acceptable carrier that maintains the cells. It may be PBS or ES medium.

The differentiated or undifferentiated cells may be preserved or maintained by any methods suitable for storage of biological material. Vitrification of the biological material is the preferred method over the traditional slow-rate freezing methods.

Effective preservation of ES cells is highly important as it allows for continued storage of the cells for multiple future usage. Although traditional slow freezing methods, commonly utilised for the cryo-preservation of cell lines, may be used to cryo-preserve undifferentiated or differentiated cells, the efficiency of recovery of viable human undifferentiated ES cells with such methods is extremely low. ES cell lines differ from other cell lines since the pluripotent cells are derived from the blastocyst and retain their embryonic properties in culture. Therefore, cryo-preservation using a method which is efficient for embryos is most appropriate. Any method which is efficient for cryo-preservation of embryos may be used. Preferably, vitrification method is used. More preferably the Open Pulled Straw (OPS) vitrification method previously described by Vajta, G. et al (1998) Molecular Reproduction and Development, 51, 53-58, is used for cryo-preserving the undifferentiated cells. More preferably, the method described by Vajta, G. et al (1998) Cryo-Letters, 19, 389-392 is employed. Generally, this method has only been used for cryopreserving embryos.

The committed progenitor cell line is efficiently recovered from cryopreservation using the traditional slow rate cooling method.

The differentiated or undifferentiated cells may be used as a source for isolation or identification of novel gene products including but not limited to growth factors, differentiation factors or factors controlling tissue regeneration, or they may be used for the generation of antibodies against novel epitopes. The cell lines may also be used for the development of means to diagnose, prevent or treat congenital diseases.

Much attention recently has been devoted to the potential applications of stem cells in biology and medicine. The properties of pluripotentiality and immortality are unique to ES cells and enable investigators to approach many issues in human biology and medicine for the first time. ES cells potentially can address the shortage of donor tissue for use in transplantation procedures, particularly where no alternative culture system can support growth of the required committed stem cell. ES cells have many other far reaching applications in human medicine, in areas such as embryological research, functional genomics, identification of novel growth factors, and drug discovery, and toxicology.

While the potential applications of neural stem cells derived from adult or embryonic CNS are considerable, there may be real advantages to neural progenitor cells derived from ES cell cultures.

ES cell lines derived from a patients' own tissue via somatic cell nuclear transfer would produce neuronal precursors which are a precise match to the recipients own tissue and might therefore be more suitable for grafting.

Moreover the use of nuclear transfer to yield ES cells from individuals with specific genetic predispostions to certain diseases of the CNS could provide a powerful tool for the generation of in vitro models for disease pathogenesis.

It is quite likely that neural precursors generated from ES cell cultures may demonstrate a greater growth or developmental potential than committed progenitors from fetal or adult CNS.

There is a huge range of cell types within the adult CNS, and while it is clear that ES cells can give rise to any of these in the mouse, it is not clear that neural stem cells can do so.

ES derived neural progenitors may allow the study of early stages of the process of neurogenesis, and thereby provide important clues for discovery of novel factors enhancing tissue regeneration, or novel stem cell intermediates which might be more facile at replacing damaged tissue.

It may be that the frequency of homologous recombination in ES cells is much higher than that in neural stem cells, and therefore that the only practical route for introducing targetted genetic modifications into human neural tissue-either for generation of disease models in vitro or for types of gene therapy-lies in the reproducible generation and isolation of neural progenitors from genetically modified embryonic stem cells.

The present invention will now be more fully described with reference to the following examples. It should be understood, however, that the description following is illustrative only and should not be taken in any way as a restriction on the generality of the invention described above.

REFERENCES

1. Evans, M. J. and Kaufman, M. Establishment in culture of pluripotential stem cells from mouse embryos. Nature 292, 151-156 (1981).
2. Martin, G. R. Isolation of a pluripotent cell line from early mouse embryos cultured in medium conditioned by teratocarcinoma stem cells. Proc. Natl. Acad. Sci U.S.A. 78, 7634-7638 (1981).
3. Andrews, P. W. et al. Pluripotent embryonal carcinoma clones derived from the human teratocarcinoma cell line Tera-2. Lab. Invest. 50, 147-162 (1984).
4. Pera, M. F., Cooper, S., Mills, J., & Parrington, J. M. Isolation and characterization of a multipotent clone of human embryonal carcinoma-cells. Differentiation 42, 10-23 (1989).
5. Thomson, J. A. et al. Isolation of a primate embryonic stem cell line. Proc. Natl. Acad. Sci. U.S.A. 92, 7844-7844 (1995).
6. Thomson, J. A. et al. Pluripotent cell lines derived from common marmoset (*Callithrix jacchus*) blastocysts. Biol. Reprod. 55, 254-259. (1996).
7. Bongso A., Fong C. Y., Ng S. C., and Ratnam, S. Isolation and culture of inner cell mass cells from human blastocysts. Hum. Reprod. 9, 2110-2117 (1994).
8. Thomson, J. A. et al. Embryonic stem cell lines derived from human blastocysts. Science 282, 1145-1147 (1998).

9. Andrews, P. W. et al. Comparative-analysis of cell-surface antigens expressed by cell-lines derived from human germ-cell tumors. Int. J. Cancer 66, 806-816 (1996).
10. Cooper, S., Pera, M. F., Bennett, W., & Finch, J. T. A novel keratan sulfate proteoglycan from a human embryonal carcinoma cell-line. Biochem. J. 286, 959-966 (1992).
11. Pera, M. F. et al. Analysis of cell-differentiation lineage in human teratomas using new monoclonal-antibodies to cytostructural antigens of embryonal carcinoma-cells. Differentiation 39, 139-149 (1988).
12. Fong C. Y., and Bongso A. Comparison of human blastulation rates and total cell number in sequential culture media with and without co-culture. Hum. Reprod. 14, 774-781 (1999).
13. Fong C. Y. et al. Ongoing pregnancy after transfer of zona-free blastocysts: implications for embryo transfer in the human. Hum. Reprod. 12, 557-560 (1997).
14. Solter D., and Knowles, B. Immunosurgery of mouse blastocyst. Proc. Natl. Acad. Sci. U.S.A. 72, 5099-5102 (1975).
15. Vajta G, Holm P, Kuwayama M, Both P J, Jacobsen H, Greve T, Callesen H. Open pulled straw (OPS) vitrification: A new way to reduce cryoinjuries of bovine ova and embryos. Molecular Reproduction and Development 1998, 51: 53-58.
16. Vajta G, Lewis I M, Kuwayama M, Greve T, Callesen H. Sterile application of the opened pulled straw (OPS) vitrification method. Cryo-Letters 1998, 19: 389-392.
17. Beddington, R. S. P. & Robertson, E. J. Axis development and early asymmetry in mammals. Cell 96, 195-209 (1999).
18. Li, M., Pevny, L., Lovell-Badge, R., and Smith, A. Generation of purified neural precursors from embryonic stem cells by lineage selection. Curr. Biol. 8, 971-974 (1998).
19. Svensden, C N and Smith A G New prospects for human stem-cell therapy in the nervous system. Trends in Neurosci 22: 357, 1999.
20. Kleinsmith L J and Pierce G B. Multipotentiality of single embryonal carcinoma cells. Cancer Res. 1964; 24: 797-842.
21. Stevens (1983)
22. Martin G R. Teratocarcinomas and mammalian embryogenesis. Science 1980; 209: 768.
23. Matsui Y, Zsebo K, Hogan B L M. Derivation of pluripotent embryonic stem cells from murine primordial germ cells in culture. Cell 1992; 70: 841-847.
24. Andrews P W. Human teratocarcinoma. Biochim. Biophys. Acta 1988; 948: 17-36.
25. Thompson S, Stern P L, Webb M, et al., Cloned human teratoma cells differentiate into neuron-like cells and other cell types in retinoic acid. J Cell Sci. 1984; 72: 37-64.
26. van Eijk M J T, van Rooijen M A, Modina S, Scesi L, Folkers G, van Tol H T A, Bevers M M, Fisher S R, Lewin H A, Shehu D, Galli C, de Vaureix C, Trounson A O, Mummery C L, and Gandolfi F. Molecular cloning, genetic mapping and developmental expression of bovine POU5F1. Biology of Reproduction 1999; 60: 1093-1103.
27. Kukekov V G, Laywell E D, Suslov O et al. Multipotent stem/progenitor cells with similar properties arise from two neurogenic regions of adult human brain. Experimental Neurology 1999, 156: 333-344
28. Uchida N, Buck D W, He D, Reitsma M J, Masek M, Phan T V, Tsukamoto A S, Gage F H, Weissman I L. Direct isolation of human central nervous system stem cells. *Proc Natl Acad Sci USA* 2000, 97:14720-5.
29. Clarke D L, Johansson C B, Wilbertz J, Veress B, Nilsson E, Karlstrom H, Lendahl U, Frisen J. Generalized potential of adult neural stem cells. *Science* 2000, 288: 1660-3.
30. Bjornson C R, Rietze R L, Reynolds B A, Magli M C, Vescovi A L. Turning brain into blood: a hematopoietic fate adopted by adult neural stem cells in vivo. *Science* 1999, 283: 534-7.
31. Vescovi, A. L. et al. Isolation and cloning of multipotential stem cells from the embryonic human CNS and establishment of transplantable human neural stem cell lines by epigenetic stimulation. *Exp. Neurol.* 156, 71-83 (1999).
32. Neelands, T. R. et al. $GABA_A$ receptor pharmacology and subtype expression in human neuronal NT2-N cells. *J. Neurosci.* 18, 4993-5007 (1998).
33. Reubinoff B E, Pera M F, Fong C Y, Trounson A and Bongso A. Embryonic stem cells. PCT/AU99/00990, U.S. application Ser. No. 09/436,164.
34. Neelands, T. R et al $GABA_A$ receptor pharmacology and subtype expression in human neuronal NT2 N cells. *J Neurosol* 18, 4993-5007 (1998).
35. Reubinoff B E, Pera M F, Fong C Y, Trounson A and Bongso A. Embryonic stem cells. PCT/AU99/00990, U.S. application Ser. No. 09/436,164.

EXPERIMENTAL PROTOCOLS

1. Derivation and Propagation of ES Cells.

Fertilised oocytes were cultured to the blastocyst stage (day 6 after insemination), in sequential media, according to a standard co-culture free protocol (Fong C. Y., and Bongso A. Comparison of human blastulation rates and total cell number in sequential culture media with and without co-culture. Hum. Reprod. 14, 774-781(1999)). After zona pellucida digestion by pronase (Sigma, St. Louis, Mo.) (Fong C. Y. et al. Ongoing pregnancy after transfer of zona-free blastocysts: implications for embryo transfer in the human. Hum. Reprod. 12, 557-560 (1997)), ICM were isolated by immunosurgery (Solter D., and Knowles, B. Immunosurgery of mouse blastocyst. Proc. Natl. Acad. Sci. U.S.A. 72, 5099-5102 (1975)) using anti-human serum antibody (Sigma) followed by exposure to guinea pig complement (Life Technologies, Gaithersburg, Md.). ICM were then cultured on mitomycin C mitotically inactivated mouse embryonic fibroblast feeder layer (75,000 cells/cm2) in gelatine coated tissue culture dishes. The culture medium consisted of DMEM (Gibco, without sodium pyruvate, glucose 4500 mg/L) supplemented with 20% fetal bovine serum (Hyclone, Logan, Utah), 0.1 mM beta-mercaptoethanol, 1% non essential amino acids, 2 mM glutamine, 50 u/ml penicillin and 50 (g/ml streptomycin (Life Technologies). During the isolation and early stages of ES cell cultivation, the medium was supplemented with human recombinant leukemia inhibitory factor hLIF at 2000 u/ml (Amrad, Melbourne, Australia). 6-8 days after initial plating, ICM like clumps were removed mechanically by a micropipette from differentiated cell outgrowths and replated on fresh feeder layer. The resulting colonies were further propagated in clumps of about 100 stem cell like cells, on mouse feeder layer, about every 7 days. The clumps were either dissociated mechanically, or with a combined approach of mechanical slicing followed by exposure to dispase (10 mg/ml, Life Technologies).

(a) Embryo Culture

Following insemination, embryos were cultured in droplets under pre-equilibrated sterile mineral oil in IVF-50 medium (Scandinavian 2 medium) for 2 days.

A mixture 1:1 of IVF-50 and Scandinavian 2 medium (Scandinavian 2 medium) was used in the third day.

From the forth day of culture, only Scandinavian 2 medium was used to grow the cleavage stage embryos to blastocysts.

(b) Zona Pellucida Digestion.

Zona pellucida digestion was performed at the expanded blastocyst stage on day 6.

The digestion solution included Pronase (Sigma, TC tested) 10 u in PBS and Scandinavian 2 medium (1:1).

The embryos were incubated in pronase solution for 1-1.5 min, washed in Scandinavian 2 medium and incubated for 30 minutes. If the zona was not completely dissolved, the embryos were further incubated in pronase solution for 15 seconds.

(c) Human Stem Cell Culture.

Human stem cells were grown on MMC treated fibroblasts' feeder layer. Fibroblasts were plated on gelatine treated dishes. A combination of human and mouse derived fibroblasts were used at a density of approximately 25,000 and 70,000 cells per $cm^2$ respectively. The fibroblasts were plated up to 48 hours before culture of the stem cells. Mouse fibroblasts only could also support the growth of the stem cells. However, while human fibroblasts could also support stem cells, they created an uneven and unstable feeder layer. Therefore, the human fibroblasts were combined with the mouse fibroblasts to augment and achieve better support of growth and prevention of differentiation.

The medium that was used for the growth of human stem was DMEM (GIBCO, without sodium pyruvate, with glucose 4500 mg/L) supplemented with 20% FBS (Hyclone, Utah) (-mercaptoethanol—0.1 mM (GIBCO), Non Essential Amino Acids—NEAA 1% (GIBCO), glutamine 2 mM. (GIBCO), penicillin 50 u/ml, and streptomycin 50 (g/ml (GIBCO). At the initial isolation of the stem cells the medium was supplemented by hLIF 2000 u/ml. It was later shown that LIF was not necessary.

(d) Human Stem Cell Propagation

Following plating, the isolated ICM attached and was cultured for 6 days. At that stage, a colony which included a clump of stem cells on top of differentiated cells developed. The ICM clump was isolated and removed mechanically by a micro-pipette with the aid of using Ca/Mg free PBS medium to reduce cell to cell attachments.

The isolated clump was replated on fresh human/mouse fibroblast feeder layer. Following 2 weeks of culture, a colony with typical morphology of primate pluripotent stem cells developed. The stem cells were further propagated in one of two methods. In both methods cells which appeared nondifferentiated were propagated in clumps of about 100 cells every 5-7 days.

In the first method, $Ca^{2+}/Mg^{2+}$ free PBS medium was used to reduce cell to cell attachments. Following about 15-20 minutes, cells gradually start to dissociate and the desired size clumps can be isolated. When cell dissociation is partial, mechanical dissociation using the sharp edge of the pipette assisted with cutting and the isolation of the clumps.

An alternative approach was performed by the combined use of mechanical cutting of the colonies followed by isolation of the subcolonies by dispase. Cutting of the colonies was performed in PBS containing Ca and Mg. The sharp edge of micropipette was used to cut the colonies to clumps of about 100 cells. The pipette was also used to scrape and remove differentiated areas of the colonies. The PBS was then changed to regular prequilibrated human stem cells medium containing dispase (Gibco) 10 mg/ml and incubated for 5-10 minutes (at 37 (C, 5% CO2). As soon as the clumps were detached they were picked up by wide bore micro-pipette, washed in PBS containing Ca and Mg and transferred to a fresh feeder layer.

e) Human Stem Cell Cryopreservation.

Early passage cells were cryo-preserved in clumps of about 100 cells by using the open pulled straw (OPS) vitrification method (Vajta et al 1998) with some modifications. French mini-straws (250 (I, IMV, L'Aigle, France) were heat-softened over a hot plate, and pulled manually until the inner diameter was reduced to about half of the original diameter. The straws were allowed to cool to room temperature and were than cut at the narrowest point with a razor blade. The straws were sterilised by gamma irradiation (15-25 K Gy). Two vitrification solutions (VS) were used. Both were based on a holding medium (HM) which included DMEM containing HEPES buffer (Gibco, without sodium pyruvate, glucose 4500 mg/L) supplemented with 20% fetal bovine serum (Hyclone, Logan, Utah). The first VS (VS1) included 10% dimethyl sulfoxide (DMSO, Sigma) and 10% ethylene glycol (EG, Sigma). The second vitrification solution (VS2) included 20% DMSO, 20% EG and 0.5M sucrose. All procedures were performed on a heating stage at 37 (C. 4-6 clumps of ES cells were first incubated in VS1 for 1 minute followed by incubation in VS2 for 25 seconds. They were then washed in a 20 (l droplet of VS2 and placed within a droplet of 1-2 (l of VS2. The clumps were loaded into the narrow end of the straw from the droplet by capillary action. The narrow end was immediately submerged into liquid nitrogen. Straws were stored in liquid nitrogen. Thawing was also performed on a heating stage at 37° C. as previously described with slight modifications (Vajta et al 1998). Three seconds after removal from liquid nitrogen, the narrow end of the straw was submerged into HM supplemented with 0.2M sucrose. After 1 minute incubation the clumps were further incubated 5 minutes in HM with 0.1 M sucrose and an additional 5 minutes in HM.

2. Stem Cell Characterisation.

Colonies were fixed in the culture dishes by 100% ethanol for immuno-fluorescence demonstration of the stem cell surface markers GCTM-2, TRA 1-60 and SSEA-1, while 90% acetone fixation was used for SSEA-4. The sources of the monoclonal antibodies used for the detection of the markers were as follows: GCTM-2, this laboratory; TRA 1-60, a gift of Peter Andrews, University of Sheffield; SSEA-1 (MC-480) and SSEA-4 (MC-813-70), Developmental Studies Hybridoma Bank, Iowa, Iowa. Antibody localisation was performed by using rabbit anti-mouse immunoglobulins conjugated to fluorescein isothiocyanate (Dako, Carpinteria, Calif.).

Alkaline phosphatase activity was demonstrated as previously described (Buehr M. and Mclaren A. Isolation and culture of primordial germ cells. Methods Enzymol. 225, 58-76, (1993)). Standard G-banding techniques were used for karyotyping.

3. Oct-4 Expression Studies.

To monitor expression of Oct-4, RT-PCR was carried out on colonies consisting predominantly of stem cells, or colonies which had undergone spontaneous differentiation as described below. mRNA was isolated on magnetic beads (Dynal A S, Oslo) following cell lysis according to the manufacturer's instructions, and solid-phase first strand cDNA synthesis was performed using Superscript II reverse transcriptase (Life Technologies). The PCR reaction was carried out according to van Eijk et al. (1999), using the solid phase cDNA as template and Taq polymerase (Pharmacia Biotech, Hong Kong). OCT-4 transcripts were assayed using the following primers: 5'-CGTTCTCTTTGGAAAGGTGTTC (forward) and 3'-ACACTCGGACCACGTCTTTC (reverse). As a control for mRNA quality, beta-actin transcripts were assayed using the same RT-PCR and the following primers:

5'-CGCACCACTGGCATTGTCAT-3' (forward), 5'-TTCTCCTTGATGTCACGCAC-3' (reverse). Products were analysed on a 1.5% agarose gel and visualised by ethidium bromide staining.

4. In-Vitro Differentiation.

Colonies were cultured on mitotically inactivated mouse embryonic fibroblasts to confluency (about 3 weeks) and further on up to 7 weeks after passage. The medium was replaced every day. Alphafetoprotein and beta human chorionic gonadotropin levels were measured in medium conditioned by HES-1 and HES-2 at passage level 17 and 6 respectively. After 4-5 weeks of culture, conditioned medium was harvested 36 hours after last medium change, and the protein levels were determined by a specific immunoenzymometric assays (Eurogenetics, Tessenderllo, Belgium) and a fluorometric enzyme immunoassay (Dade, Miami, Fla.) respectively. These compounds were not detected in control medium conditioned only by feeder layer.

Differentiated cultures were fixed 6-7 weeks after passage (26—HES-1 and 9—HES-2) for immunofluorescence detection of lineage specific markers. After fixation with 100% ethanol, specific monoclonal antibodies were used to detect the 68 kDa neurofilament protein (Amersham, Amersham U.K), and neural cell adhesion molecule (Dako). Muscle specific actin and desmin were also detected by monoclonal antibodies (Dako) after fixation with methanol/acetone (1:1). Antibody localisation was performed as described above.

5. Teratoma Formation in Severe Combined Immunodeficient (SCID) Mice.

At the time of routine passage, clumps of about 200 cells with an undifferentiated morphology were harvested as described above, and injected into the testis of 4-8 week old SCID mice (CB17 strain from the Walter and Eliza Hall Institute, Melbourne, Australia, 10-15 clumps/testis). 6-7 weeks later, the resulting tumours were fixed in neutral buffered formalin 10%, embedded in paraffin and examined histologically after hematoxylin and eosin staining.

6. Derivation and Culture of Neural Progenitors.

Two approaches were developed for the derivation of neural precursors from human ES cells:

(a) Derivation of Neural Precursors from Differentiating ES Cells:

Colonies of undifferentiated ES cells were continuously cultured on mouse embryonic fibroblasts for 2-3 weeks. The medium was changed every day. Starting from the second week of culture and more commonly at the third week, areas of tight small differentiated ES cells could be identified in the colonies both by phase contrast microscopy as well as stereo microscopy. These areas tended to become well demarcated in the third week of culture and had a typical uniform white gray opaque appearance under dark field stereo-microscopy (FIG. 26). The size and demarcation of these areas could be enhanced if after the first week of culture, the serum containing medium was replaced with serum free medium that was supplemented with epidermal growth factor 20 ng/ml (EGF, Gibco), and basic fibroblast growth factor 20 ng/ml (bFGF, Gibco) and consisted of DMEM/F12 (Gibco, Gaithersburg, Md.), B27 supplementation (1:50, Gibco), glutamine 2 mM (Gibco), penicillin 50 u/ml and streptomycin 50 µg/ml (Gibco). Clumps of about 150 small tightly packed cells were dissected mechanically by a micropipette from these areas and were transferred to plastic tissue culture dishes containing fresh serum free medium (as detailed above), supplemented with EGF (20 ng/ml), and basic FGF (20 ng/ml). The medium was supplemented with heparin 5 µg/ml (Sigma St. Louis, Mo.) in some of the experiments. The clusters of cells turned into round spheres that were comprised of small tight cells within 24 hours after transfer. The spheres were sub-cultured about every 7-21 days. The timing of subculture was determined according to the size of the spheres. The diameter of spheres at the time of sub-culture was usually above 0.5 mm. Each sphere was dissected according to its size to 4 parts by two surgical blades (size 20, Swann-Morton, Sheffield, UK) to produce clumps with a maximal diameter between 0.3-0.5 mm. 50% of the medium was changed about every 3 days.

(b) Derivation of Neural Precursors from Undifferentiated ES Cells:

Colonies of undifferentiated ES cells were propagated on mouse embryonic fibroblasts as described above. Undifferentiated ES cells were passaged in clumps of about 150-200 cells every 7 days. At the time of routine passage, clumps of about 200 ES cells were transferred to plastic tissue culture dishes containing the same serum free medium that was described in item 1 above. The clusters of cells turned into round spheres within 24 hours after transfer. The spheres were sub-cultured about every 7-21 days as described above. 50% of the medium was changed about every 3 days.

(c) Characterization of the Growth and the Number of Cells in the Spheres.

Growth of the progenitors was roughly evaluated by the increase in the number of spheres at each passage. The growth was also monitored by serial measurements of the volume of 24 spheres. Individual spheres were plated in twenty four well dishes (a sphere per well) and their diameter was evaluated every 7 days starting from the first passage (one week after derivation). The volume was calculated by using the volume equation of a ball. The spheres were passaged every 7-21 days when the diameter of at least six spheres exceeded 0.5 mm. At each passage, six spheres (diameter>0.5 mm) were sectioned into quarters that were plated individually in a 24 well tissue culture dish. When the measurements occurred 7 days after passage, the sum of volumes of the daughter spheres was compared to the sum of volumes of the mother spheres.

The number of cells per sphere and its correlation with the diameter of the spheres was evaluated in a sample of spheres with various sizes. Each sphere was mechanically disaggregated into single cells or by enzymatic (papain, Wortinington Biochemical Co, NJ) digestion that was followed by tituration. The cells were than spun down re-suspended in serum free medium and counted. The cells were also stained with trypan blue to determine the rate of viable cells.

(d) Cryopreservation of Spheres.

Spheres of precursors were transferred into a 1.2 ml cryo-vial (Nalge Nunc Napervville, Ill.) containing 0.5-1 ml of pre-cooled (4° C.) freezing medium (90% serum free medium (as above) and 10% DMSO (Sigma)). The vials were slowly cooled (~1° C./min) in a freezing container (Nalgene, Nalge Nunc Napervville, Ill.) to −80° C. and then plunged into and stored in liquid nitrogen. The vials were rapidly thawed in a water bath at 37° C. The freezing medium was gradually diluted with 10 ml serum free culture medium and the spheres were transferred to fresh serum free medium.

7. Characterization of the Progenitor Cells in the Spheres.

(a) Immunohistochemistry Studies

In general, for the immunophenotyping of spheres, disaggregated progenitor cells and differentiated cells, fixation with 4% paraformaldehyde for 20 minutes at room temperature was used unless otherwise specified. It was followed by blocking and permeabilization with 0.2% Triton X (Sigma) and 5% heat inactivated goat serum (Dako) in PBS for one hour. Samples were incubated with the primary antibodies at room temperature for 30 minutes, washed, incubated with the secondary antibodies for the same time, counter-stained and mounted with Vectashield mounting solution with DAPI (Vector Laboratories, Burlingame, Calif.). Primary antibodies localisation was performed by using swine anti-rabbit and goat anti-mouse immunoglobulins conjugated to fluorescein isothiocyanate (Dako; 1:20), and goat anti mouse IgM conjugated to Texas Red (Jackson Lab. West Grove, Pa.: 1:50). Proper controls for primary and secondary antibodies revealed neither non-specific staining nor antibody cross reactivity.

The spheres were plated on coverslips coated with poly-D-lysine (30-70 kDa, Sigma) and laminin (Sigma), fixed after 4 hours and examined by indirect immunofluorescence analysis for the expression of N-CAM (acetone fixation without permeabilization, mouse monoclonal antibody UJ13a from Dako, Carpinteria, Calif.; 1:10 and anti polysialylated N-CAM, clone MenB, kind gift of G. Rougon; 1:50)), A2B5 (4% paraformaldehyde fixation, mouse monoclonal antibody clone 105 from ATCC, 1:20), nestin (4% paraformaldehyde fixation, rabbit antiserum a kind gift of Dr. Ron McKay; 1:25) and vimentin (methanol fixation without permeabilization, mouse monoclonal antibody Vim3B4 from Roche Diagnostics Australia, Castle Hill, NSW; 1:20).

To evaluate the proportion of cells that expressed N-CAM, A2B5, nestin and vimentin, spheres that were cultivated 6-18 weeks were dissaggregated into single cells either by mechanical tituration in PBS without calcium and magnesium or by enzymatic (papain, Wortinington Biochemical Co, NJ) digestion that was followed by tituration. The cells were than plated on coverslips coated with poly-D-lysine and laminin fixed after 24 hours and examined by indirect immunofluorescence analysis for expression of N-CAM A2B5, nestin and vimentin. DAPI counterstain of the cell nuclei assisted in identifying individual cells. Two hundred cells were scored within random fields (at ×400) for the expression of each marker and the scoring was repeated at least 3 times for each marker. Three progenitor cell lines derived from differentiating colonies and two lines that were derived directly from undifferentiated cells were evaluated.

To examine the expression of endodermal markers, spheres were plated on coverslips coated with poly-D-lysine and fibronectin (Sigma, 5 mcg/mk), cultured 4 weeks in the absence of growth factors and examined by indirect immunofluorescence analysis for the expression of low molecular weight (LMW) cytokeratin (4% paraformaldehyde fixation, mouse monoclonal antibody from Beckton Dickinson, San Jose, Calif.) and laminin (4% paraformaldehyde fixation, mouse monoclonal antibody, 1:500 dilution, from Sigma).

(b) RT-PCR

Rt PCR was used to study the expression of nestin, the transcription factor PAX-6, oct4, CD-34, FLK-1, AC-133, ultra high sulfur keratin, amylase, α1 anti trypsin, transferrin HNF-3α, and alfafetoprotein (AFP), in the spheres.

Expression of the endodermal markers HNF-3α, AFP and transferin was also studied in differentiated spheres that were plated on poly-D-lysine (30-70 kDa) and Fibronectin (Sigma, 5 mcg/mk) or laminin (Sigma), cultured in the same serum free medium supplemented with growth factors for two weeks and then further cultured two weeks without growth factors supplementation.

The mRNA was isolated on magnetic beads (Dynal A S, Oslo) following cell lysis according to the manufacturer's instructions, and solid-phase first strand cDNA synthesis was performed using Superscript II reverse transcriptase (Gibco, Gaithersburg, Md.).

Alternatively, total RNA was isolated by using the RNA STAT-60™ kit (Tel-Test Inc, Friendswood, Tex.) and first strand cDNA synthesis was performed using Superscript II reverse transcriptase or SuperScript First Strand Synthesis System (Gibco, Gaithersburg, Md.) according to the manufacturers' instructions.

The PCR reaction was carried out according to van Eijk et al. (1999), using the solid phase cDNA as template and Taq polymerase (Pharmacia Biotech, Hong Kong). Alternatively, the PCR reaction mixture contained 1×PCR buffer, each primer at 0.2 µM, 0.2 µM dNTPs, 1 u Taq DNA Polymerase (Gibco) or 1 u Tfl DNA Polymerase (Promega, Madison, Wis.) and 1.5 µM Mg$^{+2}$ in a final volume of 25 µl. As a control for mRNA quality, beta-actin transcripts were assayed using the same RT-PCR. PCR primers were synthesized by Besatec or Pacific Oligos (Adelaide, Australia). The following primers were used:

| Gene | Primers | Product size |
|---|---|---|
| PAX-6 | Forward: 5'AACAGACACAGCCCTCACAAACA3' (SEQ ID NO: 1)<br>Reverse: 5'CGGGAACTTGAACTGGAACTGAC3' (SEQ ID NO: 2) | 274 bp |
| Nestin | Forward: 5'CAGCTGGCGCACCTCAAGATG3' (SEQ ID NO: 3)<br>Reverse: 5'AGGGAAGTTGGGCTCAGGACTGG3' (SEQ ID NO: 4) | 208 bp |
| Oct-4 | Forward: 5'-CGTTCTCTTTGGAAAGGTGTTC (SEQ ID NO: 5)<br>Reverse: 3'-ACACTCGGACCACGTCTTTC (SEQ ID NO: 6) | 320 bp |
| beta-actin | Forward: 5'-CGCACCACTGGCATTGTCAT-3' (SEQ ID NO: 7)<br>Reverse: 5'-TTCTCCTTGATGTCACGCAC-3' (SEQ ID NO: 8) | 200 bp |
| beta-actin | Forward: 5'-TCACCACCACGGCCGAGCG-3' (SEQ ID NO: 9)<br>Reverse: 5'-TCTCCTTCTGCATCCTGTCG-3' (SEQ ID NO: 10) | 291 bp |
| CD-34 | Forward: 5'-TGAAGCCTAGCCTGTCACCT-3' (SEQ ID NO: 11)<br>Reverse: 5'-CGCACAGCTGGAGGTCTTAT-3' (SEQ ID NO: 12) | 200 bp |
| FLK-1 | Forward: 5'-GGTATTGGCAGTTGGAGGAA-3' (SEQ ID NO: 13)<br>Reverse: 5'-ACATTTGCCGCTTGGATAAC-3' (SEQ ID NO: 14) | 199 bp |
| AC-133 | Forward: 5'-CAGTCTGACCAGCGTGAAAA-3' (SEQ ID NO: 15)<br>Reverse: 5'-GGCCATCCAAATCTGTCCTA-3' (SEQ ID NO: 16) | 200 bp |

-continued

| Gene | Primers | Product size |
|---|---|---|
| Hnf-3α | Forward: 5'-GAGTTTACAGGCTTGTGGCA-3' (SEQ ID NO: 17)<br>Reverse: 5'-GAGGGCAATTCCTGAGGATT-3' (S EQ ID NO: 18) | 390 bp |
| AFP | Forward: 5'-CCATGTACATGAGCACTGTTG-3' (SEQ ID NO: 19)<br>Reverse: 5'-CTCCAATAACTCCTGCTATCC-3' (SEQ ID NO: 20) | 340 bp |
| transferin | Forward: 5'-CTGACCTCACCTGGGACAAT-3' (SEQ ID NO: 21)<br>Reverse: 5'-CCATCAAGGCACAGCAACTC-3' (SEQ ID NO: 22) | 367 bp |
| Amylase | Forward: 5'-GCTGGGCTCAGTATTCCCCAAATAC-3' (SEQ ID NO: 23)<br>Reverse: 5'-GACGACAATCTCTGACCTGAGTAGC-3' (SEQ ID NO: 24) | 490 bp |
| α1 anti trypsin | Forward: 5'-AGACCCTTTGAAGTCAAGGACACCG-3' (SEQ ID NO: 25)<br>Reverse: 5'-CCATTGCTGAAGACCTTAGTGATGC-3' (SEQ ID NO: 26) | 360 bp |
| Keratin | Forward: 5'-AGGAAATCATCTCAGGAGGAAGGGC-3' (SEQ ID NO: 27)<br>Reverse: 5'-AAAGCACAGATCTTCGGGAGCTACC-3' (SEQ ID NO: 28) | 780 bp |

Amplification conditions were as follows: 94° C. for 4 min followed by 40 cycles of 94° C. for 15 sec, 55° C. for 30 sec, 72° C. for 45 sec and extension at 72° C. for 7 min.

Products were analysed on a 1.5% or a 2% agarose gel and visualised by ethidium bromide staining.

(c) Neuronal Differentiation Studies

In general, differentiation was induced by plating the spheres on an appropriate substrate (poly-D-lysine, 30-70 kDa, and laminin, Sigma) combined with the removal of growth factors.

Two protocols were most commonly used: In the first one, differentiation was induced by plating the spheres on coverslips coated with poly-D-lysine and laminin in the same serum free medium detailed above without growth factors supplementation. The cells in the spheres were allowed to spread and differentiate for 2-3 weeks and the medium was changed every 3-5 days. In some of the experiments, starting from the sixth day after plating, the medium was supplemented with all trans retinoic acid (Sigma, 10-6M).

In the second protocol, the spheres were plated on coverslips coated with poly-D-lysine and laminin in serum free growth medium supplemented with growth factors. After 5-6 days the supplementation of growth factors was withdrawn and all trans retinoic acid (Sigma, 10-6M) was added to the medium. The cells were further cultured for 1-2 weeks. The medium was changed every 5 days.

(d) Characterization of Differentiated Neuronal Cells

Differentiated cells growing out from the spheres were analysed 2-3 weeks after plating by indirect immunofluorescence for the expression of the following markers: 200 kDa neurofilament protein (4% paraformaldehyde fixation, mouse monoclonal antibody RT97 from Novocastra, Newcastle, UK), 160 kDa neurofilament protein (methanol fixation without permeabilization, mouse monoclonal NN18 from Chemicon, Temecula, Calif.; 1:50) 68 kDa neurofilament protein (100% ethanol, Amersham, Amersham U.K), 70 kDa neurofilament protein (Chemicon; 1:100), MAP2 a,b (4% paraformaldehyde fixation, mouse monoclonal AP20 from Neomarkers, Union City Calif.; 1:100), glutamate (1% paraformaldehyde and 1% glutaraldehyde, rabbit antiserum from Sigma; 1:1000), synaptophysin (4% paraformaldehyde, mouse monoclonal SY38 from Dako; 1:50), tyrosine hydroxylase (4% paraformaldehyde, mouse monoclonal, Sigma), serotonin (Sigma; 1:1000), glutamic acid decarboxylase (GAD, 1% paraformaldehyde, 1% glutaraldehyde, rabbit antiserum from Chemicon, Temecula, Calif.; 1:200), GABA (4% paraformaldehyde, Sigma; 1:1000), β-tubulin (4% paraformaldehyde, mouse monoclonal TUB 2.1 from Sigma) and β-tubulin III (4% paraformaldehyde mouse monoclonal SDL.3D10 from Sigma; 1:150).

Differentiated cells were also analysed 2-3 weeks after plating by RT-PCR for the expression of β-actin, glutamic acid decarboxylase (primers, Vescovi et al., 1999) $GABA_A$ receptor subunit α2 (primers, Neelands et al., 1998), neuron-specific enolase, neurofilament medium size chain (NF-M) (primers, Kukekov et al 1999). mRNA preparation and the RT-PCR reaction were carried out as described above.

(e) Glial Differentiation Studies.

At the time of routine passage spheres were subcultured into serum free medium (as detailed above) supplemented with platelet derived growth factor (recombinant human PDGF-AA, Peprotech Inc 20 ng/ml) and bFGF (Gibco, 20 ng/ml). Fifty percent of the medium was replaced by fresh medium every 3 days. After culture for 6 days the spheres were plated on coverslips coated with poly-D-lysine and laminin in the same serum free medium without growth factors supplementation. The cells in the spheres were allowed to spread and differentiate for 10-12 days and the medium was changed every 3-5 days. An alternative protocol was used in some of the experiments. In these experiments the spheres were cultured in serum free medium (as detailed above) supplemented with PDGF-AA, (20 ng/ml) and bFGF (20 ng/ml) for three weeks. The spheres were then plated on coverslips coated with poly-D-lysine and Fibronectin (Sigma, 5 mcg/mk). They were cultured for a week in the serum free medium supplemented with PDGF-AA, (20 ng/ml), bFGF (20 ng/ml) and T3 (30 nM). The growth factors were then removed from the medium and the cells were further cultured for another 1-2 weeks in the presence of T3 only. Fifty percent of the medium was replaced by fresh medium every 3 days. In an alternative approach, spheres that were propagated in the presence of EGF and bFGF were plated on coverslips coated with poly-D-lysine and Fibronectin (Sigma, 5 mcg/mk). EGF was removed from the medium and the spheres were cultured in the presence of T3 (30 nM) and bFGF (20 ng/ml) for a week. The cells were then further cultured for another 3-4 weeks in the presence of T3 and PDGF-AA (20 ng/ml).

Oligodendrocyte were identified by indirect immunofluorescence for the expression of the marker O4. The cells were first incubated with the primary (Anti oligodendrocyte marker O4, mouse monoclonal IgM from Chemicon Int. Inc.

Temecula, Calif.; 1:10) and secondary FITC or rhodamine conjugated antibodies and were then fixed with 4% paraformaldehyde.

To demonstrate differentiation into astrocyte, spheres that have been propagated in the presence of b-FGF and EGF were plated on cover slips coated with poly-D-lysine and fibronectin or laminin and further cultured for 6 days in serum free medium without growth factors supplementation.

Alternatively, spheres were propagated in the presence of PDGF-AA and bFGF for 6 weeks and were then plated on cover slips coated with poly-D-lysine and fibronectin. They were allowed to spread into a monolayer in the presence of the above growth factors for a week. The cells were then further cultured for another week in the presence of either T3 or the combination of T3 and PDGF-AA.

Following this protocols, differentiation into astrocytes was demonstrated by Indirect immunofluorescence for the expression of glial fibrillary acidic protein (GFAP) (4% paraformaldehyde fixation, rabbit anti cow from Dako; 1:50)

Differentiation into astrocyte and oligodendrocyte cells was also confirmed at the mRNA level. To induce differentiation to these lineages, spheres were plated on poly-D-lysine and fibronectin and cultured for 2 weeks in the serum free medium supplemented with EGF, bFGF and PDGF-AA. The differentiating spheres were then further cultured two weeks without growth factors and in the presence of T3. RT-PCR was used as above to demonstrate the expression of GFAP and the plp gene. GFAP transcripts were assayed using the following primers: 5'-TCATCGCTCAGGAGGTCCTT-3' (SEQ ID NO:29) (forward) and 5'-CTGTTGCCA-GAGATGGAGGTT-3' (SEQ ID NO:30) (reverse), band size 383 bp. The primers for the analysis of plp gene expression were 5'-CCATGCCTTCCAGTATGTCATC-3' (SEQ ID NO:31) (forward) and 5'-GTGGTCCAGGTGTTGAAG-TAAATGT-3' (SEQ ID NO:32) (reverse). The plp gene encodes the proteolipid protein and its alternatively spliced product DM-20 which are major proteins of brain myelin. The expected band size for plp is 354 bp and for DM-20 is 249 bp (Kukekov et al., 1999). As a control for mRNA quality, beta-actin transcripts were assayed using the same primers as above. Products were analysed on a 2% agarose gel and visualised by ethidium bromide staining.

(f) Transplantation Studies.

Spheres pre-labeled by the addition of 50 µM BrdU (Sigma) to the culture medium for 10 days, were dis aggregated into small clumps either mechanically or by enzymatic (papain, Wortinington Biochemical Co, NJ) digestion that was followed by tituration. Approximately 50,000 cells (in 2 µl PBS) were injected into the lateral ventricles of newborn (first day after birth) mice (Sabra mice, Harlan, Jerusalem) and rats (Sabra) by using a micro-glass pipette (300 micron outer diameter) connected to a micro-injector (Narishige, Japan). The glass pipette was covered by a plastic sleeve that limited the depth of penetration into the host nervous system. At 4-6 weeks of age, recipients were anesthetized and perfused with 4% paraformaldehyde in PBS.

Detection and Characterization of Donor Human Neural Progenitors In Vivo.

Serial 7-micrometer frozen sections were examined by immunostaining after post fixation with acetone or with 4% paraformaldehyde and histologically after hematoxylin and eosin staining. The transplanted cells were detected by immunostaining with antibodies for BrdU (Dako, 1:20, following specific instructions by the manufacturer), anti human specific ribonuclear protein antibody (Chemicon; 1:20) and anti human specific mitochondrial antibody (Chemicon; 1:20).

BrdU antibody was detected by using the peroxidase-conjugated Vectastain kit (Vector Burlingame, Calif.), developed with Diaminobenzadine (DAB) or by using goat anti mouse IgG conjugated to Alexa 488 (Jackson; 1:100). Anti ribonuclear protein and mitochondrial antibodies were detected with goat anti mouse IgM conjugated to Cy5 and goat anti mouse IgG conjugated to Alexa488, respectively (Jackson; 1:100). Glial cell type identity of transplanted cells was established by double staining for BrdU and GFAP (Dako; 1:100) for astrocytes, CNPase (Sigma; 1:100) and NG2 (Chemicon; 1:100) for the oligodendrocyte lineage. Neurons were detected by immunostaining with human specific anti neurofilament light chain (Chemicon; 1:100) and anti βIII-tubulin (antibody as detailed above; 1:100). Goat anti rabbit conjugated to Cy5 (Jackson; 1:100) and goat anti mouse IgG conjugated to Alexa488 (Jackson; 1:100) were used for detection of primary antibodies. In cases where the lineage specific antibody was a mouse monoclonal IgG, double labeling with BrdU was performed sequentially, by first completing immunohistochemistry for BrdU and then performing immunofluorescent staining for the lineage marker (i.e. CNPase or βIII-tubulin). Images were taken by a confocal microscope (Zeiss), using channels for Alexa488 fluorescence, Cy5 fluorescence and Nomarsky optics.

EXAMPLES

Example 1

Derivation of Cell Lines HES-1 and HES-2

The outer trophectoderm layer was removed from four blastocysts by immunosurgery to isolate inner cell masses (ICM), which were then plated onto a feeder layer of mouse embryo fibroblasts (FIG. 1A). Within several days, groups of small, tightly packed cells had begun to proliferate from two of the four ICM. The small cells were mechanically dissociated from outgrowths of differentiated cells, and following replating they gave rise to flat colonies of cells with the morphological appearance of human EC or primate ES cells (FIG. 1B, C stem cell colonies). These colonies were further propagated by mechanically disaggregation to clumps which were replated onto fresh feeder cell layers. Growth from small clumps of cells (<10 cells) was not possible under the conditions of these cultures. Spontaneous differentiation, often yielding cells with the morphological appearance of early endoderm, was frequently observed during routine passage of the cells (FIG. 1D). Differentiation occurred rapidly if the cells were deprived of a feeder layer, even in the presence of LIF (FIG. 1E). While LIF was used during the early phases of the establishment of the cell lines, it was subsequently found to have no effect on the growth or differentiation of established cultures (not shown). Cell line HES-1 has been grown for 60 passages in vitro and HES-2 for 40 passages, corresponding to a minimum of approximately 360 and 90240 population doublings respectively, based on the average increase in colony size during routine passage, and both cell lines still consist mainly of cells with the morphology of ES cells. Both cell lines have been successfully recovered from cryopreservation.

Example 2

Marker Expression and Karyotype of the Human ES Cells

Marker and karyotype analysis were performed on HES-1 at passage levels 5-7, 14-18, 24-26 and 44-46, and on HES-2 at passage levels 6-8. ES cells contained alkaline phosphatase activity (FIG. 2A). Immunophenotyping of the ES cells was carried out using a series of antibodies which detect cell surface carbohydrates and associated proteins found on human EC cells.

The ES cells reacted positively in indirect immunofluorescence assays with antibodies against the SSEA-4 and TRA 1-60 carbohydrate epitopes, and the staining patterns were similar to those observed in human EC cells (FIG. 2B, C). ES cells also reacted with monoclonal antibody GCTM-2, which detects an epitope on the protein core of a keratan sulphate/chondroitin sulphate pericellular matrix proteoglycan found in human EC cells (FIG. 2D). Like human EC cells, human ES cells did not express SSEA-1, a marker for mouse ES cells. Both cell lines were karyotypically normal and both were derived from female blastocysts.

Oct-4 is a POU domain transcription factor whose expression is limited in the mouse to pluripotent cells, and recent results show directly that zygotic expression of Oct-4 is essential for establishment of the pluripotent stem cell population of the inner cell mass. Oct-4 is also expressed in human EC cells and its expression is down regulated when these cells differentiate. Using RT-PCR to carry out mRNA analysis on isolated colonies consisting mainly of stem cells, we showed that human ES cells also express Oct-4 (FIG. 3, lanes 2-4). The PCR product was cloned and sequenced and shown to be identical to human Oct-4 (not shown).

Example 3

Differentiation of Human ES Cells In Vitro

Both cell lines underwent spontaneous differentiation under standard culture conditions, but the process of spontaneous differentiation could be accelerated by suboptimal culture conditions. Cultivation to high density for extended periods (4-7 weeks) without replacement of a feeder layer promoted differentiation of human ES cells. In high density cultures, expression of the stem cell marker Oct-4 was either undetectable or strongly down regulated relative to the levels of the housekeeping gene beta actin (FIG. 3, lanes 5-7). Alphafetoprotein and human chorionic gonadotrophin were readily detected by immunoassay in the supernatants of cultures grown to high density. Alphafetoprotein is a characteristic product of endoderm cells and may reflect either extraembryonic or embryonic endodermal differentiation; the levels observed (1210-5806 ng/ml) are indicative of extensive endoderm present. Human chorionic gonadotrophin secretion is characteristic of trophoblastic differentiation; the levels observed (6.4-54.6 IU/Liter) are consistent with a modest amount of differentiation along this lineage.

After prolonged cultivation at high density, multicellular aggregates or vesicular structures formed above the plane of the monolayer, and among these structures clusters of cells or single cells with elongated processes which extended out from their cell bodies, forming networks as they contacted other cells (FIG. 1F) were observed. The cells and the processes stained positively with antibodies against neurofilament proteins and the neural cell adhesion molecule (FIGS. 2E and F). Contracting muscle was seen infrequently in the cultures. While contracting muscle was a rare finding, bundles of cells which were stained positively with antibodies directed against muscle specific forms of actin, and less commonly cells containing desmin intermediate filaments (FIGS. 2G and H) were often observed. In these high density cultures, there was no consistent pattern of structural organisation suggestive of the formation of embryoid bodies similar to those formed in mouse ES cell aggregates or arising sporadically in marmoset ES cell cultures.

Example 4

Differentiation of Human ES Cells in Xenografts

When HES-1 or HES-2 colonies of either early passage level (6; HES 1 and 2) or late passage level (HES-1, 14 and 27) were inoculated beneath the testis capsule of SCID mice, testicular lesions developed and were palpable from about 5 weeks after inoculation. All mice developed tumours, and in most cases both testis were affected. Upon autopsy lesions consisting of cystic masses filled with pale fluid and areas of solid tissue were observed. There was no gross evidence of metastatic spread to other sites within the peritoneal cavity. Histological examination revealed that the lesion had displaced the normal testis and contained solid areas of teratoma. Embryonal carcinoma was not observed in any lesion. All teratomas contained tissue representative of all three germ layers. Differentiated tissues seen included cartilage, squamous epithelium, primitive neuroectoderm, ganglionic structures, muscle, bone, and glandular epithelium (FIG. 4). Embryoid bodies were not observed in the xenografts.

Example 5

Development, Propagation and Characterisation of Human ES Cells Derived Neural Progenitor Cells a) Derivation of Neural Progenitor Cells from Human ES Cells.

Figure 5A:
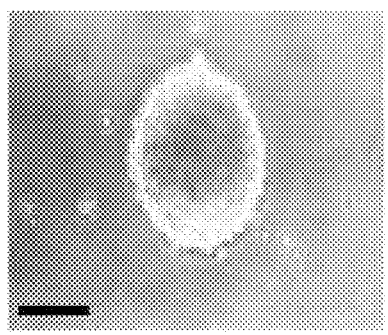

Colonies of undifferentiated ES cells from the cell lines HES-1 and HES-2 were continuously cultured on mouse embryonic fibroblasts feeder layer for 2-3 weeks. At one week after passage, some spontaneous differentiation was usually identified by changes in cell morphology in the center of the colonies. The process of differentiation included at this early stage the neuroectodermal lineage as evident by the expression of early neural markers such as nestin and PAX-6 (FIG. 19). During the next two weeks of culture, the process of differentiation was markedly accelerated mainly in the center of the colonies and cells with short processes that expressed the early neuroectodermal marker N-CAM could be demonstrated. It appeared that the N-CAM positive cells were growing out from adjacent distinct areas that were comprised of small piled, tightly packed cells that did not express GCTM-2, a marker of undifferentiated ES cells or the early neuroectodermal marker N-CAM (data not shown). These distinct areas had a typical uniform white gray opaque appearance under dark field stereo-microscopy (FIG. 26). These areas could be identified in the colonies of both cell lines from the second week after passage, and they became more defined from neighboring areas of the colony during the third week of culture (FIG. 26). The size and demarcation of these areas was enhanced if the serum containing ES cell culture medium was replaced after a week or preferably after two weeks from passage with serum free medium supplemented with EGF (20 ng/ml) and FGF (20 ng/ml). The areas were large and well demarcated sufficiently to allow mechanical removal of clumps of cells by a micropipette in 54% of the colonies cultured in serum containing medium (67/124, HES-1). Clumps were removed from differentiating colonies of HES-1 and HES-2 and were transferred to serum free medium supplemented with basic fibroblast growth factor (bFGF) and epidermal growth factor (EGF). At the time of isolation, the clumps were comprised mostly of a layer of the small tightly packed cells (about 100-300 cells/clump), on top of some loosely attached larger cells, It was possible to remove these larger cells mechanically or by enzymatic digestion. Within an hour the clumps started to change their shape toward spheres and after 24 hours all the clumps turned into round spheres (FIG. 5a).

During the initial two weeks in culture, some cell death was observed. After 7-10 days in culture, gradual increase in the size of the majority of the spheres was evident and most of the spheres were still floating or loosely attached to the dish while a minority attached and started to spread. A detailed analysis of marker expression and the growth and differentiation potential of the cells within the spheres was conducted in three preparations of spheres that were separately derived with this approach.

In an alternative approach, somatic differentiation of ES cells into spheres of progenitor cells was induced by transferring clumps of undifferentiated ES cells into serum free medium supplemented with basic fibroblast growth factor (bFGF) and epidermal growth factor (EGF). Within 24 hours the clumps have turned into spheres. Some of these spheres were round and some had an irregular shape. After 72 hours in serum free medium 42% (10/24) of the spheres had a round symmetrical appearance (FIG. 9) and after 12 days 62.5% (15/24). Significant growth was observed in the majority of the spheres during this early culture. It was possible to measure and calculate the average volume of the round floating spheres and it increased by 64% (mean growth of 15 spheres) between days 5 and 12. Two preparations of spheres that were separately derived with this approach were further propagated and characterized.

b) In Vitro Propagation of Spheres of Progenitor Cells

After 7-10 days in culture, floating or loosely attached spheres with a diameter of >0.5 mm were sub-cultured by mechanical dissection into 4 pieces, which were re-plated in fresh pre-equilibrated medium. The spheres were cultivated in this manner during a five to six month period (15 passages). Although some of the spheres had an irregular shape at the initial phase of culture, the rate of round symmetrical spheres increased along propagation. In addition, while at early passage levels the appearance (under a stereo-microscope) of the inner part of the spheres was irregular, it gradually turned to be uniform at more advanced passage levels. By passage level five (five-six weeks after derivation) all spheres had a round symmetrical shape and a uniform appearance.

Proliferation of the cells was evaluated by determining the increase in the number of spheres with each passage as well as measuring the increase in the volume of the spheres along time. In general, the growth rate of spheres that were generated either from undifferentiated or from differentiating ES cells had a similar pattern characterized by a more excessive growth during the first 5-6 passages. The number of spheres increased by 126%+54% (Mean+SD, sum of results from 3 cell lines) at each passage (performed every 7 days) during the first 5 passages. The growth of the number of spheres with each passage was then reduced to 10-50% per week. This growth rate was maintained for prolonged periods (4 months) (mean data from 3 cell lines). The mean volume of spheres generated either from differentiating ES cells or directly from undifferentiated cells also increased by similar rates (FIGS. 16 and 17). A relatively rapid growth rate was observed during the first 5-6 weeks after derivation with a population doubling time of approximately 4.7 days. It was followed by a 10-16 week period of slow and stable cell growth with a population doubling time of approximately two and a half weeks. At this point the spheres ceased to grow and their volume was stable or declined (FIG. 31).

Figure 10:
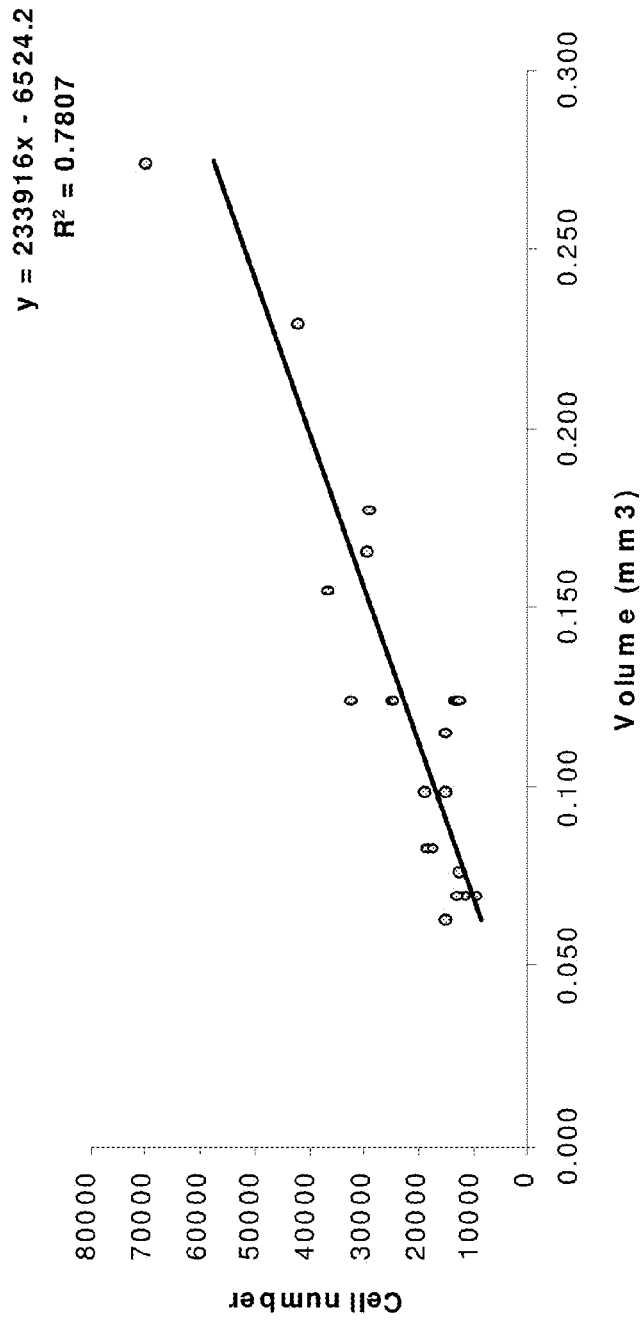
FIG. 10 shows linear correlation between the volume of spheres and the number of progenitor cells within a sphere. Spheres of various diameters that were generated from differentiating ES colonies and were propagated for 14-15 weeks were dissaggregated into single cell suspension and the number of cells per sphere was counted.

Dis-aggregation of the spheres by using trypsin digestion could be ineffective in particular when the spheres were cultivated for prolonged periods, however it was possible to dis-aggregate them into a single cell suspension mechanically following enzymatic digestion with papain. A linear correlation was found between the volume of spheres and the number of cells within the spheres at various passage levels (5-15 weeks after derivation) indicating the validity of monitoring the increment of sphere volume as an indirect indicator of cell proliferation. The coefficients that define the regression line of this correlation were similar in spheres that were derived from differentiating or undifferentiated ES cells. Most of the cells (>90%) were viable following the dissagregation procedure (FIG. 10, FIG. 18).

Given the growth rate of the spheres with each passage and the number of cells (20,000, FIG. 10, 18) per averaged size sphere (0.1 mm$^3$ based on the mean diameter±S.D. of 24 spheres 7 days after passage 5, 0.59±0.14 mm), it was calculated that 10 clumps of ES cells may generate within 10 passages 2500 spheres containing 50×10$^6$ cells. A cumulative growth curve is presented in FIG. 31 to illustrate this potential for significant expansion.

Figure 7:
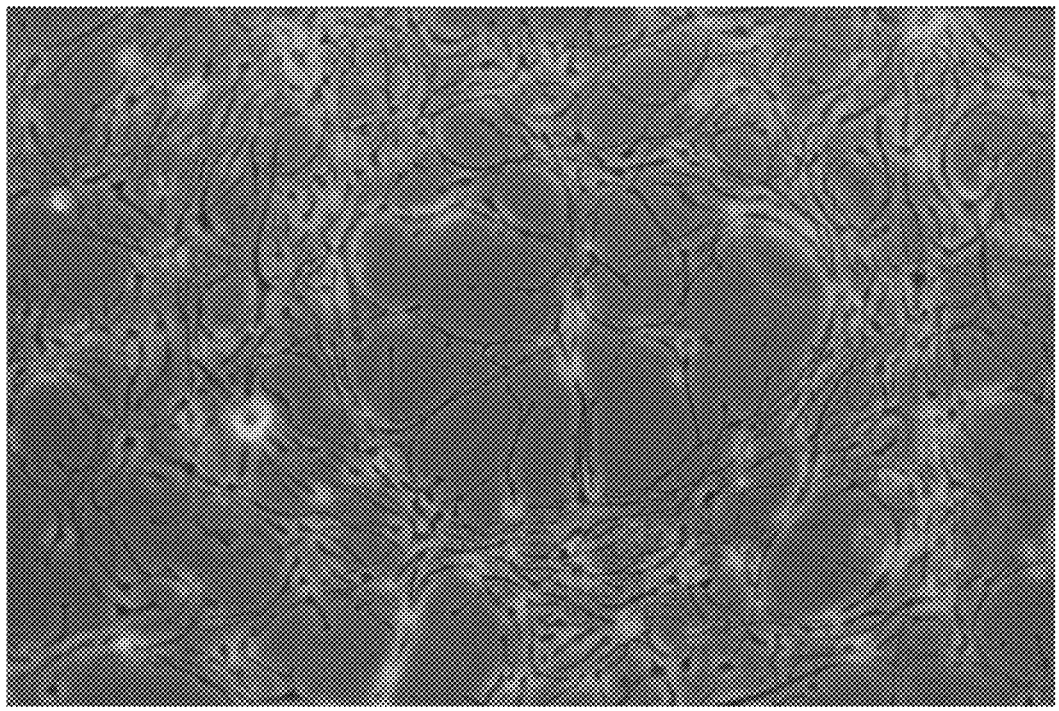
FIG. 7 shows neural precursors proliferating as a monolayer on a plastic tissue culture dish in the presence of EGF and bFGF. These monolayer cultures of proliferating cells were obtained after prolonged cultivation (2-3 weeks) of the spheres in the presence of growth factors without sub-culturing.

Spheres that were cultured in the serum free growth medium (supplemented with growth factors) for prolonged periods (3 weeks) without passage, tended to attach to the tissue culture plastic and gradually spread as a monolayer of cells. The cells in the monolayer had a uniform appearance of neural progenitors and a high mitotic activity was evident (FIG. 7).

It was possible to recover the spheres from cryopreservation.

c) Characterization of the Progenitor Cells within the Spheres.

Figure 5B:
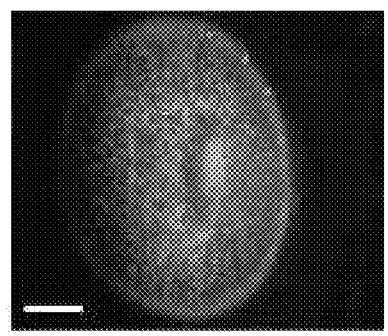
Figure 5C:
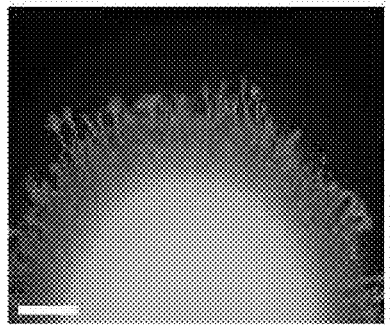
Figure 5D:
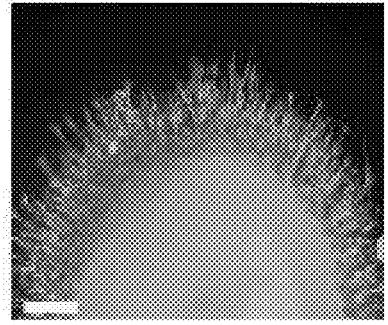
Figure 11:
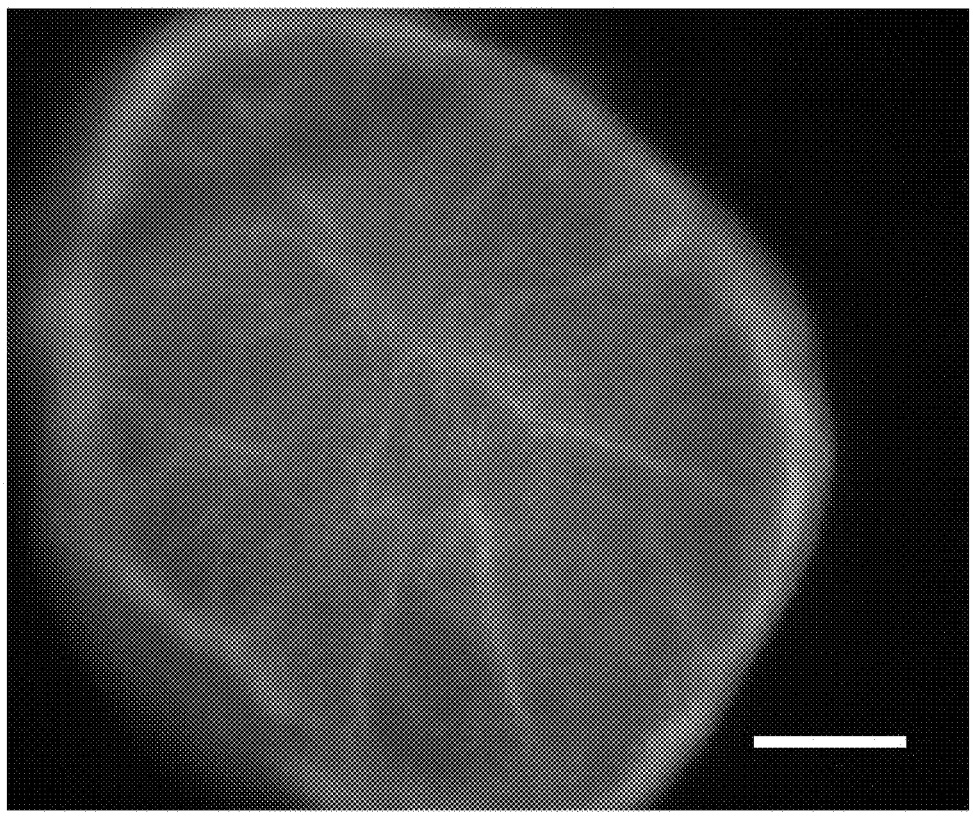
FIG. 11 shows indirect immunofluorescence staining of a sphere, 4 hours after plating on adhesive substrate, for N-CAM. The sphere was generated by direct transfer of undifferentiated ES cells into serum free medium and propagation of the resulting spheres for 5 passages. (Scale bar 100 microns).

Cells in the spheres that were produced either from differentiating ES cell colonies or directly from undifferentiated ES cells expressed markers of primitive neuroectoderm and neural progenitor cells, such as polysialylated N-CAM (FIG. 5b, 11, 12), A2B5, the intermediate filament proteins nestin (immunostaining, FIGS. 5c and 13; RT-PCR, FIG. 3b and FIG. 19) and vimentin (FIGS. 5d and 15), and the transcription factor Pax-6 (FIG. 3b and FIG. 19). The expression of these markers was maintained along prolonged cultivation (18 weeks). The transcriptional factor oct4 was not expressed by the cells in the spheres indicating that undifferentiated human ES cells were not present within the spheres (FIG. 19).

To evaluate the proportion of cells in the spheres that expressed N-CAM, A2B5, nestin and vimentin, spheres that were cultivated at least 6 weeks (and up to 18 weeks) were disaggregated to single cell suspension. The resulting single cells were plated on substrate in growth medium. Twenty four hours after plating, an average of 99±1.6% (n=11 experiments) and 95.5% (95.7%-96.7%, n=6) of the cells from spheres generated form differentiating (three progenitor cell lines) and undifferentiated ES cells (two progenitor cell lines) respectively were decorated with the antibody against N-CAM. The average proportion of cells that were positively stained for nestin, A2B5, and vimentin was 97±2.3% (n=10 experiments) 89.5% (n=2 experiments) and 67±16.8% (n=9 experiments) respectively in spheres that were established from differentiating colonies. Nestin and vimentin were expressed by 66.8% (48.5%-100%, n=5) and 58% (41.6%-76.5%, n=5) of the cells that originated from spheres that were generated from undifferentiated cells. These proportions were stable during prolonged cultivation (18 weeks).

The high proportion of cells that expressed N-CAM indicate that the spheres from both sources were comprised of a highly enriched preparation of neural progenitor cells. An extremely high proportion of cells from spheres that were derived from differentiating ES colonies also expressed the neural progenitor markers nestin and A2B5. The proportion of cells expressing nestin was less extensive in spheres that originated from undifferentiated ES cells. The high proportion of cells that expressed these markers was stable along prolonged cultivation.

To determine whether cells from other lineages were present within the spheres, the expression of markers of endoderm, epidermis and mesoderm was examined by RT-PCR and immunohistochemistry.

There was no evidence for the expression of markers of the extraembryonic endodermal lineage (HNF-3α, AFP, RT-PCR, FIG. 24,) by cells of spheres that were derived by either methods. Moreover, the expression of markers of the endodermal lineage was also not detected in spheres that were derived from differentiating colonies and that were induced to differentiate by plating on an appropriate substrate and culturing in the absence of growth factors for 4 weeks (HNF-3α, AFP, were evaluated by RT-PCR; LMW cytokeratin and laminin were evaluated by immunohistochemistry). ES cell colonies that were induced to differentiate by prolonged culture (3-4 weeks) expressed all of the above markers and served as positive controls.

However, expression of markers of mesodermal precursors (FLK-1 and CD-34) was demonstrated in the spheres that were produced by either method (FIG. 24). In addition, transcripts of markers of embryonic endoderm (α1 anti trypsin, transferrin and amylase), epidermis (keratin) and the hematopoietic lineage (Ac-133) were demonstrated in spheres that were derived from differentiating ES colonies (FIG. 32).

It may be concluded that the spheres were comprised of a highly enriched population of neural progenitors (>95%) and probably no cells from the extraembryonic endodermal lineage. The expression of transcripts of non-neural markers may indicate the presence of a minute population of cells from other lineages within the spheres. Alternatively it may be that the primitive neural precursors within the spheres express these markers. The expression of the hematopoietic marker AC-133 (Uchida et al., 2000) that was recently demonstrated in neural stem cells derived from human fetal brains support this possibility. In addition, expression of non-neural markers by the neural progenitors may be in line with the recently reported broad potential of neural stem cells to transdifferentiate into a variety of tissues (Bjornson et al., 1999; Clarke et al., 2000).

(d) In Vitro Neuronal Differentiation

When plated on poly-D-lysine and laminin, spheres that were produced either from differentiating ES cell colonies or from undifferentiated ES cells attached, and differentiated cells grew out onto the monolayer from them.

Figure 6:
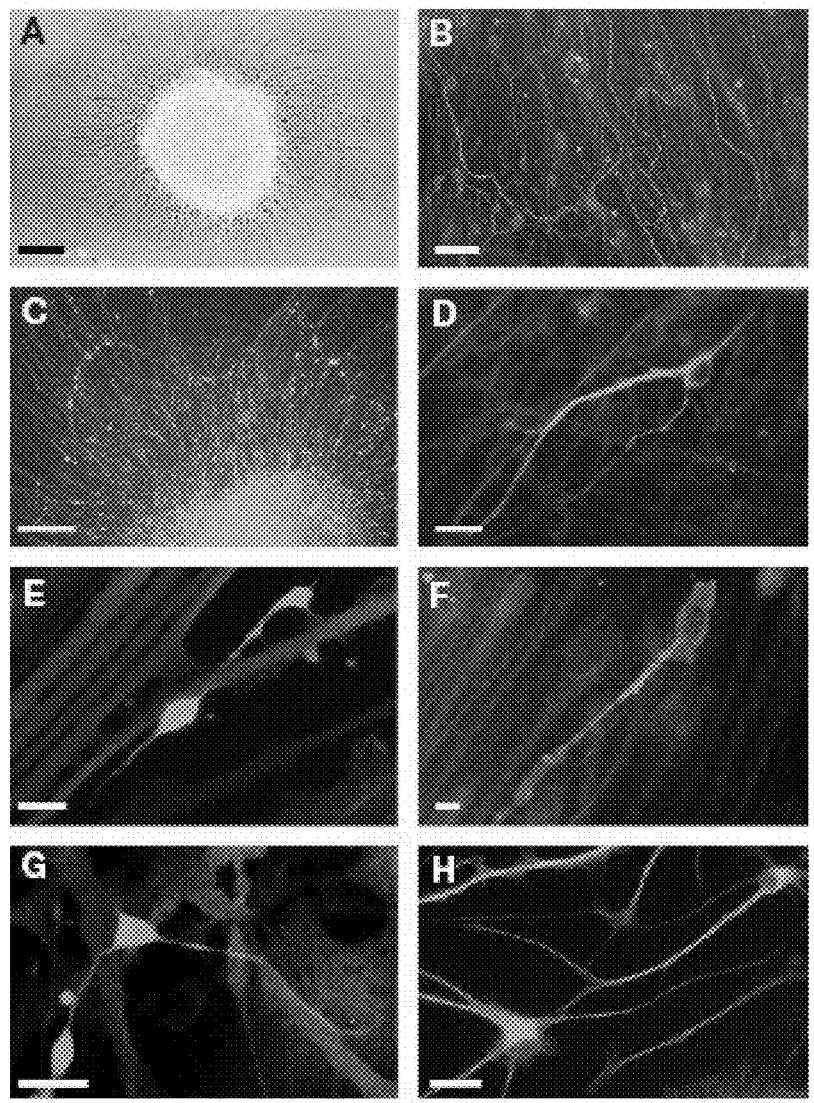
Figure 8:
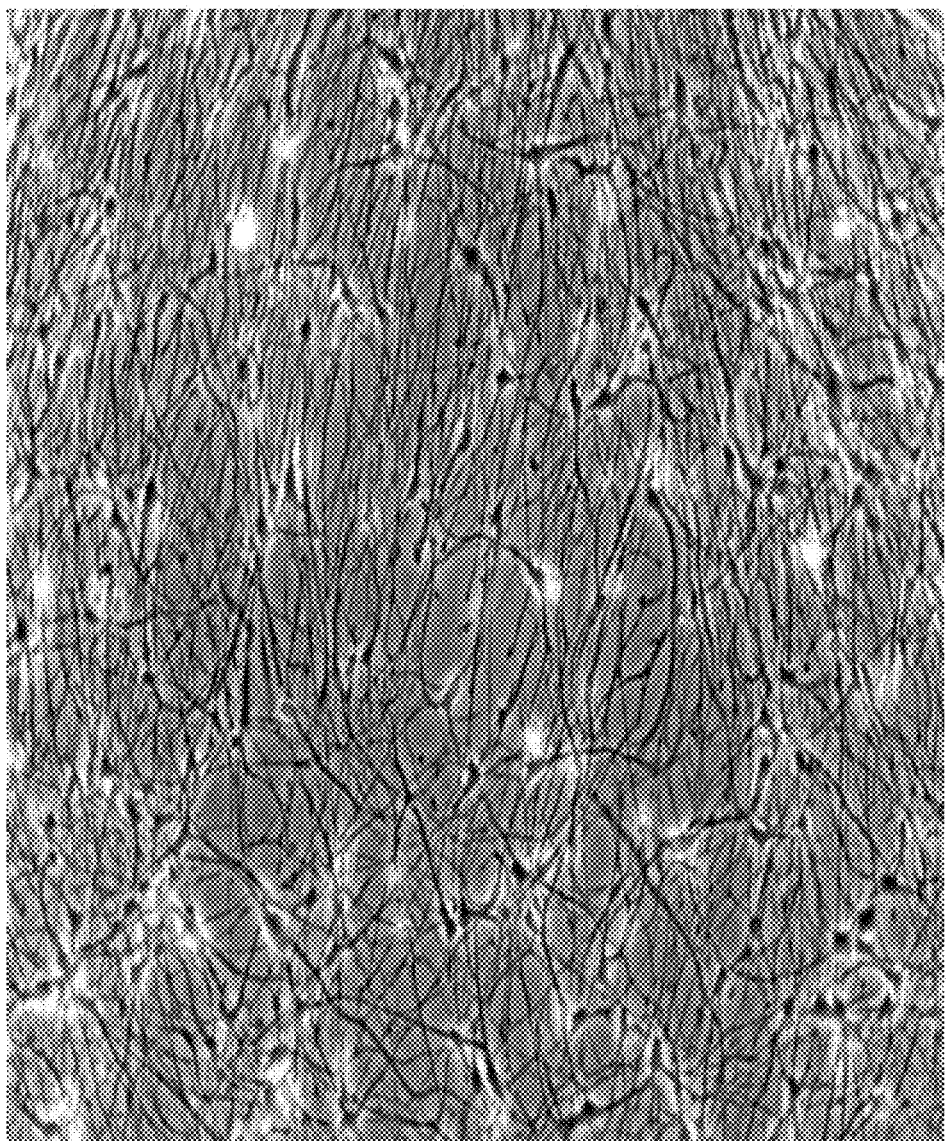
FIG. 8 shows phase contrast appearance of a culture consisting of differentiated neural cells.

When the bFGF and EGF were removed at the time of plating, differentiating cells gradually spread from them in a radial fashion (FIG. 6a, FIG. 33) If the growth factors were removed only after 1-2 weeks, a more extensive spreading of cells with processes, which formed a monolayer was evident (FIG. 8). Two to three weeks after plating, the differentiated cells originating from spheres derived by either methods displayed morphology and expression of structural markers characteristic of neurons, such as β-tubulin (FIG. 6h), β-tubulin III (FIG. 27c, the 200 kDa neurofilament (FIG. 6b) and 68 kDA neurofilament proteins and neuron specific enolase (NSE, FIG. 34). Moreover, differentiated cells originating from spheres derived by either methods expressed markers of mature neurons such as the 160 kDa neurofilament protein (FIG. 6c, FIG. 27a, FIG. 34), Map-2a,b (FIG. 6d, FIG. 27b) and synaptophysin (FIG. 6F), Furthermore, the cultures contained cells which synthesised glutamate (FIG. 6e), serotonin (FIG. 35a), GABA (FIG. 35b), expressed the rate limiting enzyme in GABA biosynthesis (glutamic acid decarboxylase, FIGS. 3c and 6g), expressed the enzyme tyrosine hydroxylase (FIG. 28) and receptor subunits characteristic of GABA minergic neurons (GABAα2, FIG. 3d).

e) In Vitro Glial Differentiation

Differentiation into both astrocyte cells and oligodendrocyte cells was observed with spheres that were produced either from differentiating ES cells or from undifferentiated cells.

While differentiation at a low scale toward glial cells was observed upon withdrawal of growth factors and plating on poly-D-lysine and laminin, various protocols were developed to enhance the differentiation toward this lineage. These protocols were all based on plating the neural progenitor cells on poly-D-lysin and fibronectin, which significantly enhanced the differentiation toward glial cells, and supplementation of the medium with PDGF-AA that promotes glial progenitor cell proliferation and T3 that induces maturation of oligodendrocytes precursors.

Differentiation into the astrocyte glial lineage was demonstrated by indirect immunofluorescent staining for GFAP. Few positive cells were occasionally demonstrated when differentiation was induced by withdrawal of growth factors and plating on poly-D-lysin and laminin. However, differentiation into astrocytes was significantly enhanced when the spheres were allowed to differentiate on poly-D-lysin and fibronectin. Moreover, differentiation into astrocytes was highly abundant after the following protocol. The spheres were first propagated six weeks in the presence of PDGF-AA and bFGF and were then plated on poly-D-lysine and fibronectin. They were allowed to spread for a week into a monolayer in the presence of the above growth factors. The differentiating cells were then further cultured for another week in the presence of T3 and PDGF-AA followed by another 1-2 weeks of culture either with T3 or the combination of T3 and PDGF-AA (FIG. 20).

To promote differentiation towards oligodendrocyte, spheres were initially cultured for 6 days in serum free medium supplemented with PDGF-AA (20 ng/ml) and bFGF (20 ng/ml) and were then plated on coverslips coated with poly-D-lysine and laminin in the same medium without growth factors supplementation. The cells in the spheres were allowed to spread and differentiate for 10-12 days. Small cells decorated with the antibody O4 could be demonstrated at that time indicating differentiation into oligodendrocyte progenitors.

It was also possible to promote the differentiation into oligodendrocyte progenitors by incubation of the spheres in the presence of PDGF and basic FGF for 3 weeks followed by plating on poly lysine and fibronectin and culture for a week in the presence of the growth factors and T3 followed by 1-2 weeks culture in the presence of T3 without growth factors supplementation (FIG. 14). Alternatively, spheres that were propagated in the presence of bFGF and EGF were plated on poly lysine and fibronectin and cultured for a week in the presence of bFGF and T3. The cells were then further cultured in the presence of PDGF and T3 for 3-4 weeks.

Differentiation into astrocyte and oligodendrocyte cells was further confirmed at the mRNA level. Spheres were plated on poly-D-lysine and fibronectin and cultured for 2 weeks in the serum free medium supplemented with EGF, bFGF and PDGF-AA. The differentiating spheres were then further cultured two weeks without growth factors in the presence of T3. The expression of GFAP was demonstrated by RT-PCR indicating and confirming the presence of astrocyte cells (FIG. 25, FIG. 34). The expression of myelin basic protein (MBP) and the plp gene was used as markers of differentiation into oligodendrocyte cells. The plp gene encodes the proteolipid protein and its alternatively spliced product DM-20, which are major proteins of brain myelin.

RT-PCR analysis of the differentiated spheres demonstrated MBP and bothdm-20 and plp transcripts indicating that differentiation into oligodendrocyte has occurred (FIG. 25, FIG. 34).

f) Transplantation of Neural Spheres.

To explore the developmental potential of the human ES-derived neural progenitors in vivo, and to reveal whether the human precursors can respond to positional cues, migrate along established host brain tracts, differentiate into neural cell types according to a given region's stage of development and participate in the development and histogenesis of a living host, dis-aggregated spheres were implanted into the lateral cerebral ventricles of newborn mice. Transplantation was performed 9-15 weeks after derivation of the neural spheres. Prior to transplantation, the neural progenitors were labeled with BrdU to facilitate their identification in the host brain. Histological and immunochemical evaluation of serial brain sections was performed mainly 4-6 weeks after transplantation. The transplanted cells were identified by their immunoreactivity with anti BrdU antibodies (FIGS. 21 and 36E). Numerous BrdU+ cells were found in 9 out of 14 transplanted animals and successful engraftment was documented with donor cells from the three neural progenitor clones. The human identity of cells that were decorated with anti BrdU was confirmed by double labeling demonstrating immunoreactivity with both anti BrdU and anti human specific ribonucleoprotein antibodies (FIG. 37B). The identity of the transplanted human cells was also confirmed by immunofluorescent staining with a human-specific anti-mitochondrial antibody (FIG. 37A).

Transplanted newborns that were examined during the first postnatal week exhibited clusters of donor cells lining the ventricular wall (FIG. 36A). At 4-6 weeks following implantation, human cells had left the ventricles and migrated in large numbers mainly as individual cells into the host brain parenchyma. The human cells demonstrated a widespread distribution in various regions of the host brain including periventricular areas (FIG. 22), the entire length of the corpus callosum, fimbria, internal capsule, as well as into diencephalic tissue around the 3rd ventricle (FIG. 36B, D). Transplanted human cells also migrated anteriorily from the subventricular zone along the rostral migratory stream (FIG. 23, FIG. 36C) and populated the olfactory bulb, indicating their potential to respond to local cues and migrate along established host brain tracts. In addition, BrdU+ cells were found in the dentate gyrus (not shown), where post-natal neuronogenesis is known to occur as well.

Differentiation in vivo into the three fundamental neural lineages was demonstrated by immunochemical studies using anti human cell type specific antibodies or double labeling experiments with both anti BrdU and anti neural cell type specific antibodies. Glial differentiation of the transplanted cells was abundant in the periventricular areas that consist of white matter tracks where glial differentiation in the post natal period is predominant. Double labeling immunochemical studies for BrdU and GFAP demonstrated cells that were decorated by both antibodies indicating in-vivo differentiation into astrocytes (FIG. 29, FIG. 37C). Transplanted cells that have differentiated into the oligodendroglial lineage and were reactive with anti BrdU and anti NG-2 (a marker of oligodendrocyte progenitors) or anti 2',3'-cyclic nucleotide 3'-phosphodiesterase (CNPase), were also demonstrated in these areas (FIG. 30 and FIGS. 37D and E).

Neuronal differentiation of the human transplanted cells was specifically demonstrated in the olfactory bulb, a region where neuronogenesis occurs after birth. Neuronal processes of transplanted cells were also detected by a human specific anti light chain neurofilament antibody in the fimbria (FIGS. 37F and G).

There was no histological evidence of tumor formation in any of the recipient animals.

Our data demonstrated that neural progenitors that were derived from human ES cells in vitro could respond appropriately to normal developmental cues in vivo. Following transplantation to the cerebral ventricles of newborn mice, the donor cells migrated in large numbers into the host brain parenchyma and demonstrated widespread distribution. Migration was not random and the transplanted human progenitors followed established brain pathways as demonstrated by their migration along the RMS, suggesting their responsiveness to host's signals. The human ES derived neural progenitors differentiated in vivo into neurons, astrocyte and oligodendrocyte cells. Differentiation into neurons was demonstrated only in the olfactory bulb where host differentiation into this lineage occurs in the postnatal period, whereas differentiation into astroglia and oligodendroglia was demonstrated in subcortical areas where gliogenesis predominates and neurogenesis has ended. These data demonstrate that cell fate was determined in a region specific manner and according to a given region's stage of development. It should be noted that the ability to integrate and participate in host brain histogenesis was maintained after prolonged proliferation of the ES derived neural progenitors in vitro.

Example 6

Cryo-Preservation of Human ES Cells

Attempts to cryo-preserve human ES cells by using conventional slow freezing protocols were associated with a very poor outcome after thawing. Since ES cells are derived from the blastocyst and retain their embryonic properties in culture, we have postulated that cryopreservation by using a method which is efficient for embryos may be beneficial. Early passage clumps of human ES cells were frozen by using the open pulled straw (OPS) vitrification method which was recently shown to be highly efficient for the cryopreservation of bovine blastocysts (Vatja et al. 1998). Both cell lines were successfully thawed and further propagated for prolonged periods. The outcome of the vitrification procedure was further studied on cell line HES-1, and recovery of viable cells with this procedure was found to be highly efficient. All clumps (n=25) survived the procedure and attached and grew after thawing. Vitrification was associated with some cell death as evidenced by the reduced size of colonies originating from vitrified clumps two days after thawing in comparison to colonies from non-vitrified control clumps. However, two days in culture were sufficient to overcome this cell deficit, and 9 days after plating the size of colonies from frozen-thawed clumps exceeded that of control colonies at 7 days. Vitrification did not induce differentiation after thawing. Thawed cells retained a normal karyotype and the expression of primate stem cell markers, and formed teratomas in SCID mice.

Finally it is to be understood that various other modifications and/or alterations may be made without departing from the spirit of the present invention as outlined herein.

The invention claimed is:

1. A method of inducing neural differentiation of embryonic stem (ES) cells comprising:
   (a) culturing isolated, undifferentiated, human ES cells in the presence of serum free medium supplemented with growth factors which include epidermal growth factor (EGF) and basic fibroblast growth factor (bFGF) to produce neurospheres containing neural progenitor cells, wherein said neurospheres do not express alphafetoprotein; and
   (b) culturing said neurospheres under conditions that induce neural differentiation, thereby inducing neural differentiation of the ES cells.

2. The method claim 1, wherein the inducing neural differentiation results in generation of neurons.

3. The method of claim 2, further comprising:
   (c) culturing the neural progenitor cells on an adhesive substrate comprising poly-D-lysine in the presence of a serum free media and growth factors; and
   (d) inducing the neural progenitor cells to differentiate into neurons by withdrawal of the growth factors, thereby generating neurons.

4. The method of claim 1, wherein the inducing neural differentiation results in generation of oligodendrocytes and/or astrocytes.

5. The method of claim 4 further comprising:
   (c) culturing the neural progenitor cells in serum free medium in the presence of PDGF-AA and bFGF; and
   (d) plating the neural progenitor cells on an adhesive substrate which comprises poly-D-lysine and fibronectin, in serum free medium without PDGF-AA or bFGF, thereby inducing differentiation of the neural progenitor cells into oligodendrocytes or astrocytes.

6. The method of claim 4 further comprising:
   (c) culturing the neural progenitor cells in serum free medium in the presence of PDGF-AA and bFGF;
   (d) plating the neural progenitor cells on an adhesive substrate which comprises poly-D-lysine and fibronectin;
   (e) culturing the neural progenitor cells in serum free medium in the presence of PDGF-AA, bFGF and T3; and
   (f) inducing differentiation of the neural progenitor cells by withdrawing PDGF-AA and bFGF in the medium.

7. The method of claim 1, wherein said ES cells are prepared according to a method comprising: obtaining an in vitro fertilised human embryo and growing the embryo to a blastocyst stage of development; removing inner cells mass (ICM) cells from the embryo; culturing ICM cells under conditions which do not induce extraembryonic differentiation and cell death, and promote proliferation of undifferentiated stem cells; and recovering stem cells.

8. The method of claim 7, wherein the method for preparing ES cells is further characterized by: culturing the ICM cells on a fibroblast feeder layer to promote proliferation of embryonic stem cells prior to recovering the stem cells from the feeder layer, wherein the fibroblast feeder cells are arrested in their growth; replating the stem cells from the fibroblast feeder layer onto another fibroblast feeder layer; and culturing the stem cells for a period sufficient to promote proliferation of morphologically undifferentiated stem cells.

9. The method of claim 3, further comprising determining an expression of a neuronal cell marker following step (d).

10. The method of claim 3, wherein said adhesive substrate further comprises laminin.

11. The method of claim 10, further comprising culturing said cells in the presence of retinoic acid following step (c).

12. The method of claim 1, wherein said culturing ES cells does not generate embryoid bodies.

13. The method of claim 1, wherein said culturing said ES cells is effected as monolayers or spheres.

14. The method of claim 9, wherein said neuronal cell marker is selected from the group consisting of 200 kDa neurofilament protein, 160 kDa neurofilament protein, MAP2a+b, glutamate, synaptophysin, glutamic acid decarboxylase and .beta.-tubulin.

15. The method of claim 2, wherein said neurons are mature neurons.

* * * * *